(12) United States Patent
Lim et al.

(10) Patent No.: US 12,187,729 B2
(45) Date of Patent: Jan. 7, 2025

(54) COMPOUNDS HAVING PDE9A INHIBITORY ACTIVITY, AND PHARMACEUTICAL USES THEREOF

(71) Applicant: KOREA RESEARCH INSTITUTE OF CHEMICAL TECHNOLOGY, Daejeon (KR)

(72) Inventors: Chae Jo Lim, Daejeon (KR); Kwang-Seok Oh, Daejeon (KR); Jeong Hyun Lee, Daejeon (KR); Kyu Yang Yi, Daejeon (KR); Nack Jeong Kim, Daejeon (KR); Byung Ho Lee, Daejeon (KR); Ho Won Seo, Daejeon (KR); Soo Hee Kim, Daejeon (KR); Junyoung Choi, Daejeon (KR); Mi Young Lee, Daejeon (KR); Ju Hee Lee, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 809 days.

(21) Appl. No.: 17/311,293

(22) PCT Filed: Dec. 5, 2019

(86) PCT No.: PCT/KR2019/017128
§ 371 (c)(1),
(2) Date: Jun. 4, 2021

(87) PCT Pub. No.: WO2020/116972
PCT Pub. Date: Jun. 11, 2020

(65) Prior Publication Data
US 2022/0017528 A1 Jan. 20, 2022

(30) Foreign Application Priority Data
Dec. 6, 2018 (KR) .................. 10-2018-0156038

(51) Int. Cl.
*A61K 31/519* (2006.01)
*C07D 487/04* (2006.01)

(52) U.S. Cl.
CPC ................. *C07D 487/04* (2013.01)

(58) Field of Classification Search
CPC .................................................. A61K 31/519
See application file for complete search history.

(56) References Cited

U.S. PATENT DOCUMENTS

| 6,413,975 B1 | 7/2002 | Chasin et al. |
| 2016/0185785 A1 | 6/2016 | Ioannidis et al. |

FOREIGN PATENT DOCUMENTS

| EP | 3181566 A1 | 6/2017 |
| KR | 10-2002-0065341 A | 8/2002 |
| WO | 96/18400 A1 | 6/1996 |
| WO | 2007008548 A2 | 1/2007 |
| WO | 2012/020022 A1 | 2/2012 |
| WO | 2012/040230 A1 | 3/2012 |
| WO | 2017/000276 A1 | 1/2017 |
| WO | 2017003895 A1 | 1/2017 |
| WO | 2017/070293 A1 | 4/2017 |

OTHER PUBLICATIONS

Zheng et al., An overview of phosphodiesterase 9 inhibitors: insights from skeletal structure, pharmacophores, and therapeutic potential, 2023, European Journal of Medicinal Chemistry, vol. 259, p. 1-15. (Year: 2023).*
Al-Chalabi, Preventing neurodegenerative disease, 2021, Brain, vol. 144, p. 1279-1280. (Year: 2021).*
RN 850912-08-02 (Chemical Abstract compound. STN express) May 23, 2005.
International Search Report issued Mar. 20, 2020, corresponding to International Application No. PCT/KR2019/017128 citing the above reference(s).
CAS registry No. 922692-57-7, "2-[[4,5-dihydro-1-(2-methylphenyl)-4-oxo-1H-pyrazolo[3,4-d]pyrimidin-6-yl]thio]-N-[15-(ethylthio)-1,3,4-thiadiazol-2-yl]- acetamide".
CAS registry No. 922622-05-7, "2-[[4,5-dihydro-1-(3-methylphenyl)-4-oxo-1H-pyrazolo[3,4-d]pyrimidin-6-yl]thio]-N-(5-methyl-1,3,4-thiadiazol-2-yl)-acetamide".
CAS registry No. 922568-42-1, "2-[[4,5-dihydro-1-(3-methylphenyl)-4-oxo-1H-pyrazolo[3,4-d]pyrimidin-6-yl]thio]-N-[5-(ethylthio)-1,3,4-thiadiazol-2-yl]-acetamide".
CAS registry No. 922567-43-9, "2-[[4,5-dihydro-1-(2-methylphenyl)-4-oxo-1H-pyrazolo[3,4-d]pyrimidin-6-yl]thio]-N-(5-methyl-1,3,4-thiadiazol-2-yl)-acetamide".
CAS registry No. 922556-09-0, "2-[[1-(3-chlorophenyl)-4,5-dihydro-4-oxo-1H-pyrazolo[3,4-d]pyrimidin-6-yl]thio]-N-(5-methyl-1,3,4-thiadiazol-2-yl)-acetamide".
CAS registry No. 922106-39-6, "2-[[1-(2,3-dimethylphenyl)-4,5-dihydro-4-oxo-1H-pyrazolo[3,4-d]pyrimidin-6-yl]thio]-N-[5-(ethylthio)-1,3,4-thiadiazol-2-yl]-acetamide".
CAS registry No. 922082-29-9, "2-[[1-(1, 1-dimethylethyl)-4,5-dihydro-4-oxo-1H-pyrazolo[3,4-d]pyrimidin-6-yl]thio]-N-[5-(ethylthio)-1,3,4-thiadiazol-2-yl]-acetamide".
CAS registry No. 922023-36-7, "2-[[1-(3-chlorophenyl)-4,5-dihydro-4-oxo-1H-pyrazolo[3,4-d]pyrimidin-6-yl]thio]-N-[5-(ethylthio)-1,3,4-thiadiazol-2-yl]-acetamide".

(Continued)

*Primary Examiner* — Joseph K McKane
*Assistant Examiner* — Karen Cheng
(74) *Attorney, Agent, or Firm* — Hauptman Ham, LLP

(57) ABSTRACT

The present invention provides a compound having a specific chemical structure and having PDE9A inhibitory activity, or a pharmaceutically acceptable salt thereof. The present invention provides a composition containing the compound or a pharmaceutically acceptable salt thereof. The present invention provides a pharmaceutical use, for treating or preventing PDE9A-related diseases, of the compound according to the present invention, a salt thereof, and a composition containing the compound or salt. The present invention also provides a method for treating or preventing PDE9A-related diseases, the method comprising administering an effective amount of the compound according to the present invention, a salt thereof, or a composition containing the compound or salt to a subject in need of treatment.

8 Claims, No Drawings

(56) References Cited

OTHER PUBLICATIONS

CAS registry No. 921909-79-7, "2-[[1-(2,3-dimethylphenyl)-4,5-dihydro-4-oxo-1H-pyrazolo[3,4-d]pyrimidin-6-yl]thio]-N-(5-methyl-1,3,4-thiadiazol-2-yl)-acetamide".

CAS registry No. 921889-75-0, "2-[[1-(1,1-dimethylethyl)-4,5-dihydro-4-oxo-1H-pyrazolo[3,4-d]pyrimidin-6-yl]thio]-N-(5-methyl-1,3,4-thiadiazol-2-yl)-acetamide".

CAS registry No. 851125-81-0, "2-[[1-(3,4-dimethylphenyl)-4,5-dihydro-4-oxo-1H-pyrazolo[3,4-d]pyrimidin-6-yl]thio]-N-(5-methyl-1,3,4-thiadiazol-2-yl)-acetamide".

CAS registry No. 851125-80-9, "2-[1-(3,4-dimethylphenyl)-4,5-dihydro-4-oxo-1H-pyrazolo[3,4-d]pyrimidin-6-yl]thiol-N-[5-{ethylthio)-1,3,4-thiadiazol-2-yl]-acetamide".

CAS registry No. 851124-69-1, "2-[[4,5-dihydro-1-(4-methylphenyl)-4-oxo-1H-pyrazolo[3,4-d]pyrimidin-6-yl]thio]-N-(5-methyl-1,3,4-thiadiazol-2-yl)-acetamide".

CAS registry No. 851124-67-9, 2-[[4,5-dihydro-1-(4-methylphenyl)-4-oxo-1H-pyrazolo[3,4-d]pyrimidin-6-yl]thio]-N- [5-(ethylthio)-1,3,4-thiadiazol-2-yl]-acetamide.

CAS registry No. 851123-14-3, "2-[[1-(4-chlorophenyl)-4,5-dihydro-4-oxo-1H-pyrazolo[3,4-d]pyrimidin-6-yl]thio]-N-[5-(ethylthio)-1,3,4-thiadiazol-2-yl]-acetamide".

CAS registry No. 534593-32-3, "2-[[1-(4-fluorophenyl)-4,5-dihydro-4-oxo-1H-pyrazolo[3,4-d]pyrimidin-6-yl]thio]-N-(5-methyl-1,3,4-thiadiazol-2-yl)-acetamide".

CAS registry NO. 850912-07-1, "2-[{4,5-dihydro-4-oxo-1-phenyl-1H-pyrazolo[3,4-d]pyrimidin-6-yl)thio]-N-[5- (ethylthio)-1,3,4-thiadiazol-2-yl]-acetamide".

CAS registry No. 534593-30-1, "N-[5-(ethylthio)-1,3,4-thiadiazol-2-yl]-2-[[1-(4-fluorophenyl)-4,5-dihydro-4-oxo-1H-pyrazolo[3,4-d]pyrimidin-6-yl]thio]-acetamide".

Australian Office Action dated Mar. 15, 2022 for corresponding Australian Patent Application No. 2019394593.

Hearing Notice in Reference of Application No. 202127029608 issued on Jan. 4, 2024, with its English translation, 2 pages.

\* cited by examiner

COMPOUNDS HAVING PDE9A INHIBITORY ACTIVITY, AND PHARMACEUTICAL USES THEREOF

CROSS-REFERENCE TO RELATED APPLICATION

This present application is a national stage filing under 35 U.S.C § 371 of PCT application number PCT/KR2019/017128 filed on Dec. 5, 2019 which is based upon and claims the benefit of priority to Korean Patent Application No. 10-2018-0156038 filed Dec. 6, 2018 in the Korean Intellectual Property Office. The disclosures of the above-listed applications are hereby incorporated by reference herein in their entireties.

TECHNICAL FIELD

The present invention relates to a group of compounds having a specific structure and excellent PDE9A inhibitory activity. The invention also relates to pharmaceutical compositions comprising such compounds. The present invention relates to a useful method for treating diseases related to PDE9A using these compounds. That is, the present invention relates to a medical use of the compounds according to the present invention for treating or preventing PDE9A-related diseases.

BACKGROUND ART

Phosphodiesterase 9A (PDE9A) is mainly expressed in the brain, particularly in the neocortex of the cerebellum and hippocampus, and is known to be associated with the regulation of cGMP concentration, i.e. glutamate-related signals through memory and learning. Therefore, inhibition of phosphodiesterase 9A is known to be useful in the treatment of Alzheimer's disease, CNS disorders, or cognitive disorders caused by various neurodegenerative processes. Therefore, it is recognized as a useful pharmacological target for the treatment or alleviation of cognitive disorders such as dementia with frontal lobe degeneration including Lewy body dementia, Pick's syndrome, Parkinson's disease and Alzheimer's disease with learning and memory problems.

Furthermore, in addition to cranial nerve diseases, overexpression of phosphodiesterase 9A has recently been found in patients with heart disease, especially in patients with cardiac output-preserving heart failure, and overexpression of phosphodiesterase 9A has been observed in animal models that induce pathological conditions of the heart. In addition, the effects of improving cardiac function and relieving myocardial hypertrophy through the inhibition of phosphodiesterase 9A have been reported, and thus, it is attracting attention recently as a useful pharmacological target for patients with cardiovascular disease, especially those with cardiac output-preserving heart failure.

DISCLOSURE

Technical Problem

Accordingly, a problem to be solved by the present invention is to provide a compound having PDE9A inhibitory activity, a pharmaceutical composition comprising the compound as an active ingredient, and a medical use for the treatment or prevention of PDE9A-related diseases thereof.

Another problem to be solved by the present invention is to provide a method for treating or alleviating PDE9A-related diseases, characterized in that it inhibits PDE9A activity, and it comprises administering the compound according to the present invention to a patient in need of treatment, improvement or prevention of PDE9A-related diseases.

Technical Solution

In order to solve the above problem, one embodiment of the present invention provides a compound represented by the following Chemical Formula 1 or a pharmaceutically acceptable salt thereof.

[Chemical Formula 1]

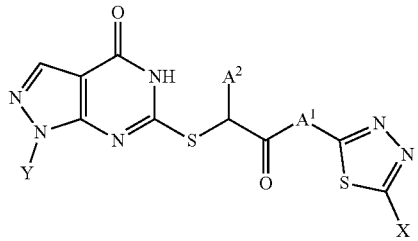

In the Chemical Formula 1,
$A^1$ is NH or N—$C_{1-2}$alkyl,
$A^2$ is H, linear or branched $C_{1-5}$alkyl, or phenyl,
X is a substituent selected from the group consisting of —H, halogen, —$NO_2$, —CN, —$SR^1$, linear or branched $C_{1-10}$alkyl unsubstituted or substituted with one or more halogens, linear or branched $C_{1-10}$alkoxy unsubstituted or substituted with one or more halogens, $C_{6-10}$aryl unsubstituted or substituted with one or more halogen or $C_{1-10}$ linear or branched alkyl, and $C_{6-10}$aryloxy unsubstituted or substituted with one or more halogen or $C_{1-10}$ linear or branched alkyl,
Y is a substituent selected from the group consisting of $C_{1-10}$ linear or branched alkyl unsubstituted or substituted with one or more halogens, $C_{3-10}$cycloalkyl unsubstituted or substituted with one or more halogens, 6-10 membered heterocycloalkyl comprising O or S heteroatom unsubstituted or substituted with one or more halogens, $C_{1-10}$ linear or branched alkoxy unsubstituted or substituted with one or more halogens, $C_{6-10}$aryl unsubstituted or substituted with one or more halogen or $C_{1-10}$ linear or branched alkyl, and $C_{6-10}$aryloxy unsubstituted or substituted with one or more halogen or $C_{1-10}$ linear or branched alkyl,
$R_1$ is a substituent selected from the group consisting of $C_{1-10}$ linear or branched alkyl unsubstituted or substituted with one or more halogens, $C_{1-10}$ linear or branched alkoxy unsubstituted or substituted with one or more halogens, $C_{6-10}$aryl unsubstituted or substituted with one or more halogen or $C_{1-10}$ linear or branched alkyl, $C_{1-2}$alkyl-$C_{6-10}$aryl unsubstituted or substituted with one or more halogen or $C_{1-10}$ linear or branched alkyl, and $C_{6-10}$aryloxy unsubstituted or substituted with one or more halogen or $C_{1-10}$ linear or branched alkyl.

As used herein, the terms "halogen" and "halo" mean fluorine, chlorine, bromine or iodine.

As used herein, the term "$C_{6-10}$aryl" means a carbocyclic aromatic group containing 6 to ring atoms. Representative examples include, but are not limited to, phenyl, tolyl, xylyl, naphthyl, tetrahydronaphthyl, anthracenyl, fluorenyl, indenyl, and azulenyl. The carbocyclic aromatic group may be optionally substituted.

As used herein, the term "aryloxy" is RO—, and R is aryl as defined above.

As used herein, the term "pharmaceutically acceptable salt(s)" refers to a salt prepared from active compounds according to the present disclosure with relatively non-toxic acids or bases, depending on the particular substituents of those compounds. When the compounds have a relatively acidic group, base-added salts can be obtained by contacting the neutral compounds with a sufficient amount of the desired base and a pure or inert solvent. Suitable pharmaceutically acceptable base addition salts include, but are not limited to sodium, potassium, calcium, aluminum, organic amino, magnesium salts and the like. When the compounds have a relatively basic group, acid-added salts can be obtained by contacting the neutral compounds with a sufficient amount of the desired acid and pure or inert solvent. Suitable pharmaceutically acceptable acid addition salts include salts derived from non-toxic organic acids including, but are not limited to, acetic acid, propionic acid, isobutyl acid, oxalic acid, maleic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, and the like, and non-toxic inorganic acids including, but are not limited to, hydrochloric acid, hydrobromic acid, nitric acid, carbonic acid, monohydrogencarbonic acid, phosphoric acid, monohydrogenphosphric acid, dihydrogenphosphoric acid, sulfuric acid, monohydrogensulfuric acid, hydrogen iodide, phosphorous acid and the like. Also it includes a salt of amino acid such as arginate or its analogues, and it also includes analogues of organic acid such as glucuronic or galacturonic acid. Some specific compounds of this disclosure have both basic and acidic functionality for the conversion of compounds with a basic or acidic portion (addition) salts.

As used herein, the phrase "compound(s) of this/the invention" includes any compound(s) of Chemical Formula 1, as well as clathrates, hydrates, solvates, or polymorphs thereof. And, even if the term "compound(s) of the invention" does not mention its pharmaceutically acceptable sat, the term includes salts thereof. In one embodiment, the compounds of this disclosure include stereo-chemically pure compounds, e.g., those substantially free (e.g., greater than 85% ee, greater than 90% ee, greater than 95% ee, greater than 97% ee, or greater than 99% ee) of other stereoisomers. That is, if the compounds of Chemical Formula 1 according to the present disclosure or salts thereof are tautomeric isomers and/or stereoisomers (e.g., geometrical isomers and conformational isomers), such isolated isomers and their mixtures also are included in the scope of this disclosure. If the compounds of the present disclosure or salts thereof have an asymmetric carbon in their structures, their active optical isomers and their racemic mixtures also are included in the scope of this disclosure.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

In one embodiment according to the present invention, preferably, among the substituents of Chemical Formula 1
$A^1$ is NH or N—$C_{1-2}$alkyl,
$A^2$ is H, linear or branched $C_{1-5}$alkyl, or phenyl,
X is a substituent selected from the group consisting of —H, halogen, —$NO_2$, —CN, —$SR^1$, linear or branched $C_{1-5}$alkyl unsubstituted or substituted with one or more halogens, linear or branched $C_{1-5}$alkoxy unsubstituted or substituted with one or more halogens, and phenyl unsubstituted or substituted with one or more halogen or $C_{1-10}$ linear or branched alkyl,
Y is a substituent selected from the group consisting of $C_{1-6}$ linear or branched alkyl unsubstituted or substituted with one or more halogens, $C_{3-6}$cycloalkyl unsubstituted or substituted with one or more halogens, 6-8 membered heterocycloalkyl comprising O or S heteroatom unsubstituted or substituted with one or more halogens, $C_{1-6}$ linear or branched alkoxy unsubstituted or substituted with one or more halogens, $C_{6-10}$aryl unsubstituted or substituted with one or more halogen or $C_{1-10}$ linear or branched alkyl, and $C_{6-10}$aryloxy unsubstituted or substituted with one or more halogen or $C_{1-10}$ linear or branched alkyl, and
$R_1$ is a substituent selected from the group consisting of $C_{1-6}$ linear or branched alkyl unsubstituted or substituted with one or more halogens, $C_{1-6}$ linear or branched alkoxy unsubstituted or substituted with one or more halogens, $C_{6-10}$aryl unsubstituted or substituted with one or more halogen or $C_{1-10}$ linear or branched alkyl, and $C_{6-10}$aryloxy unsubstituted or substituted with one or more halogen or $C_{1-10}$ linear or branched alkyl.

In one embodiment according to the present invention, more preferably, among the substituents of Chemical Formula 1
$A^1$ is NH or $NCH_3$,
$A^2$ is H, $CH_3$, or phenyl,
X is a substituent selected from the group consisting of —H, —Cl, —Br, —$SR^1$, methyl, ethyl, t-butyl, trifluoromethyl, methoxy, ethoxy, isopropoxy, phenyl, 4-fluorophenyl, and 4-methylphenyl, Y is phenyl, 4-fluorophenyl, 4,4-difluorocyclohexyl, pyran, thiopyran, isopropyl or cyclopropyl, and R$^1$ is methyl, ethyl, isopropyl, propyl, benzyl, 4-methylbenzyl or 4-chlorobenzyl.

In order to achieve the above-mentioned object, the present inventors performed various evaluation experiments after synthesizing various compounds in order to secure compounds having high PDE9A inhibitory activity and high selectivity for them and their use, and finally the present invention was completed by confirming that the compounds of the present invention were suitable for the purposes of the present invention.

Non-limiting examples of preferred compounds according to the present invention include the compounds of Table 1 below and pharmaceutically acceptable salts thereof.

In addition, the present invention provides, as shown in Scheme 1 below, a method for preparing a compound represented by Chemical Formula 1, comprising the step of obtaining a compound represented by Chemical Formula 1 by reacting a compound represented by Chemical Formula 2 with a compound represented by Chemical Formula 3.

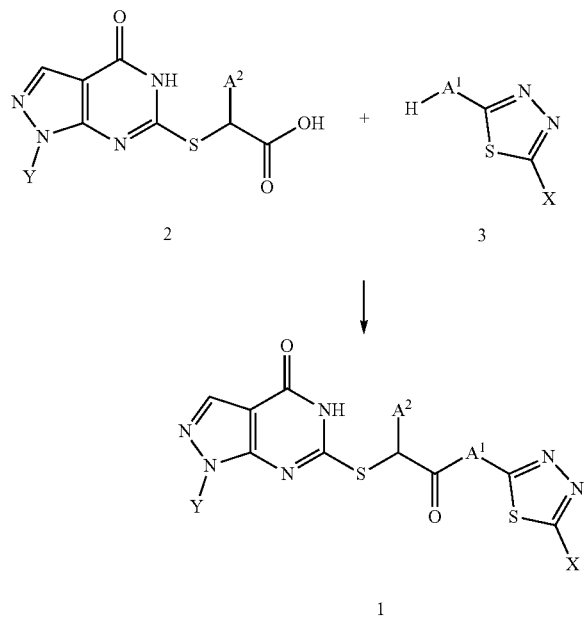

[Scheme 1]

In Scheme 1, A$^1$, A$^2$, X and Y are as defined in Chemical Formula 1.

Hereinafter, the manufacturing method represented by Scheme 1 according to the present invention will be described in detail.

The compound represented by Chemical Formula 1 according to the present invention is can be prepared through a condensation reaction using a carboxylic acid compound represented by Chemical Formula 2 and an amine compound represented by Chemical Formula 3 as starting materials, as shown in Scheme 1 above.

In the method for preparing a compound represented by Chemical Formula 1 according to the present invention, Step 1 is a step of obtaining a compound represented by Chemical Formula 1 by reacting a compound represented by Chemical Formula 2 with a compound represented by Chemical Formula 3. Specifically, a compound represented by Chemical Formula 1 can be prepared by condensing a compound represented by Chemical Formula 2 and a compound represented by Chemical Formula 3 in the presence of a condensing agent. More specifically, a compound represented by Chemical Formula 1 having an amide bond can be prepared by condensing a carboxylic acid compound represented by Chemical Formula 2 and an amine compound represented by Chemical Formula 3 in the presence of a condensing agent and a base.

At this time, the condensation reaction can be carried out through two conventional methods, and specific examples are as follows.

Manufacturing Method 1-A

It can be prepared by using a condensing agent with the compound represented by Chemical Formula 2 and the compound represented by Chemical Formula 3 in Scheme 1 in the presence of a base.

At this time, the usable condensing agent include organic phosphorus-based reagents such as bis(2-oxo-3-oxazolidinyl)phosphinic chloride (BOP-Cl), benzotriazol-1-yloxytris(dimethylamino)phosphonium hexafluorophosphate (BOP), and diphenylphosphorylazide (DPPA); carbodiimide-based reagents such as dicyclohexylcarbodiimide (DCC), diisopropylcarbodiimide (DIC), and 1-ethyl-3-(3-dimethylaminopropyl)carbodiimide (EDC); N,N-carbonyldiimidazole; O-benzotriazole-N,N,N',N'-tetramethyl-uroninium-hexafluorophosphate (HBTU); 1-[bis(dimethylamino)methylene]-1H-1,2,3-triazolo[4,5-b]pyridinium 3-oxide hexafluorophosphate (HATU); 2-chloro-1-methylpyridinium iodide (CMPI); 2-fluoro-4,6-dimethoxy-1,3,5-triazine (CDMT).

In addition, the base is used to accelerate the reaction and increase the yield, and the available base includes organic bases such as N,N-dimethylaminopyridine (DMAP), pyridine, triethylamine, N,N-diisopropylethylamine, and 1,8-diazabicyclo[5.4.0]-7-undecene (DBU) or inorganic bases such as sodium bicarbonate, sodium hydroxide, and potassium hydroxide. These may be used alone or in combination, in an equivalent amount or in excess.

Further, the reaction solvent include ether solvents such as tetrahydrofuran, dioxane, dichloromethane, and 1,2-dimethoxyethane; aromatic hydrocarbon solvents such as benzene, toluene, and xylene; dimethylformamide (DMF); dimethylsulfoxide; acetonitrile; and the like. These can be used alone or in combination. The reaction temperature is from 0° C. to the boiling point of the solvent.

Manufacturing Method 1-B

In addition, the carboxylic acid compound represented by Chemical Formula 2 of Scheme 1 is converted to be an acyl halide, a carboxylic anhydride, or an active ester (e.g., p-nitrophenyl ester, N-hydroxylsuccinimide ester, pentafluorophenyl ester, etc.) by a known method, and then it is reacted in the presence of a base with an amine compound represented by Chemical Formula 3 to give a compound represented by Chemical Formula 1.

At this time, the base includes a tertiary amine organic base such as triethylamine and diisopropylethylamine, and an inorganic base such as sodium carbonate, potassium carbonate, potassium hydroxide, sodium hydroxide, cesium carbonate, barium hydroxide, etc. These may be used alone or in combination, in an equivalent amount or in excess.

In addition, a solvent that can be used in the reaction includes ether solvents such as dioxane, tetrahydrofuran, and 1,2-dimethoxyethane; halogen-containing solvents such as 1,2-dichloromethane, or 1,2-dichloroethane; aromatic hydrocarbon solvents such as benzene and toluene, and the like. These may be used alone or in combination. The reaction may happen without a solvent. The reaction temperature is from 0° C. to the boiling point of the solvent.

Preparation of the Starting Material (Compound Represented by Chemical Formula 2)

The compound of Chemical Formula 2, which is the starting material of Scheme 1, can be prepared by a method comprising a step of obtaining a compound represented by Chemical Formula 6 by reacting a compound represented by Chemical Formula 4 with a compound represented by Chemical Formula 5 (Step 1); a step of obtaining a compound represented by Chemical Formula 7 by reacting the compound represented by Chemical Formula 6 obtained in Step 1 (Step 2); a step of obtaining a compound represented by Chemical Formula 9 by reacting the compound represented by Chemical Formula 7 obtained in Step 2 with a compound represented by Chemical Formula 8 (Step 3); and a step of obtaining a compound represented by Chemical Formula 2 by reacting the compound represented by Chemical Formula 9 obtained in Step 3 (Step 4), as shown in Scheme 2 below.

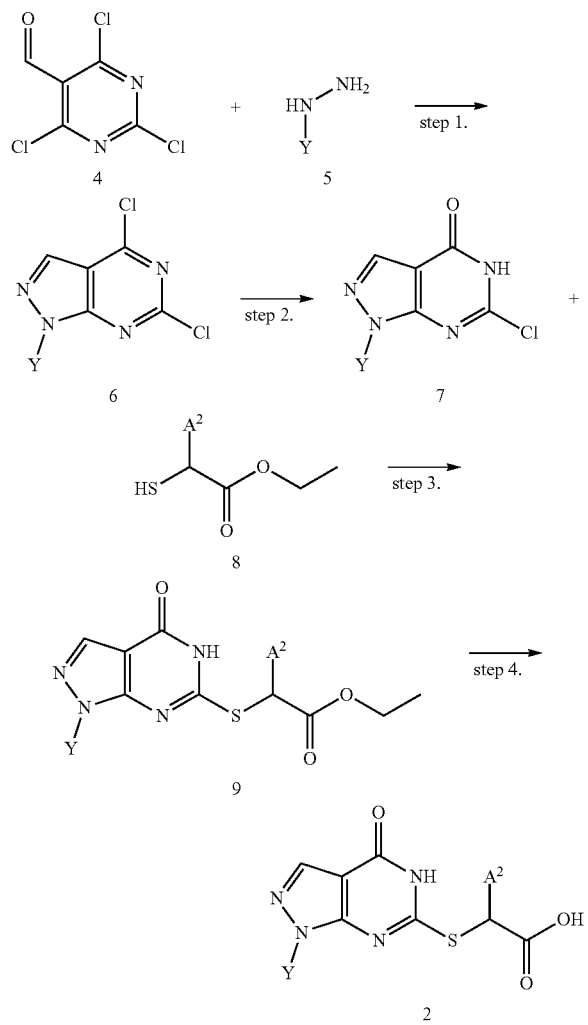

[Scheme 2]

In Scheme 2, Y and $A^2$ are as defined in Chemical Formula 1.

Hereinafter, the manufacturing method represented by Scheme 2 will be described in detail.

In the manufacturing method represented by Scheme 2, Step 1 is a step of reacting a compound represented by Chemical Formula 4 with a compound represented by Chemical Formula 5 to give a compound represented by Chemical Formula 6. Specifically, this is a step to obtain a compound represented by Chemical Formula 6 through a cyclization reaction with an aldehyde represented by Chemical Formula 4 and Compound 5 called hydrazine under basic conditions.

In the above reaction, the compound represented by Chemical Formula 5 may be a commercially available compound, and the chemical represented by Chemical Formula 6 may be a commercially available compound or prepared by a known method from the corresponding ketone compound.

In addition, piperidine is a representative base that can be used in the reaction. In addition, organic bases such as pyrrolidine, pyridine, triethylamine, N,N-diisopropylethylamine, and DBU or inorganic bases such as NaOH, $Na_2CO_3$, $K_2CO_3$, and $Cs_2CO_3$ may be used in an equivalent amount or in excess.

In addition, the reaction solvent is an ether solvent such as tetrahydrofuran, dioxane, and 1,2-dimethoxyethane, an aromatic hydrocarbon solvent such as benzene, toluene, and xylene, a lower alcohol such as methanol, ethanol, propanol, and butanol, dimethylformamide (DMF), dimethyl sulfoxide (DMSO), acetonitrile, water, etc. can be used alone or in combination, and the reaction temperature is from 0° C. to the boiling point of the solvent.

In the manufacturing method represented by Scheme 2, Step 2 is a step of obtaining a compound represented by Chemical Formula 7 by reacting the compound represented by Chemical Formula 6 obtained in Step 1. Specifically, this is a step of preparing a carboxylic acid compound represented by Chemical Formula 7 by hydrolyzing an ester compound represented by Chemical Formula 6 under basic or acid conditions.

At this time, the base includes an inorganic base such as sodium carbonate, potassium carbonate, potassium hydroxide, sodium hydroxide, cesium carbonate, and barium hydroxide. These may be used alone or in combination, in an equivalent amount or in excess. The acid includes hydrochloric acid, sulfuric acid, methanesulfonic acid or the like, and the acids may be used alone or in combination, in an equivalent amount or in excess.

In addition, solvents that can be used in the reaction include ether solvents such as tetrahydrofuran, dioxane, dichloromethane, and 1,2-dimethoxyethane, aromatic hydrocarbon solvents such as benzene, toluene, and xylene, alcohol-based solvents such as methanol and ethanol, dimethylformamide (DMF), dimethyl sulfoxide (DMSO), acetonitrile, water, and the like. These may be used alone or in combination. The reaction temperature is from 0° C. to the boiling point of the solvent.

In the manufacturing method represented by Scheme 2, Step 3 is a step of obtaining a compound represented by Chemical Formula 9 by reacting the compound represented by Chemical Formula 7 obtained in Step 2 with a thiol represented by Chemical Formula 8. Specifically, this is a step of preparing an ester compound represented by Chemical Formula 9 by substituting a pyrazolopyrimidinone compound substituted with chlorine represented by Chemical Formula 7 obtained in Step 2 and a thiol represented by Chemical Formula 8 under basic conditions.

In this case, the base includes an inorganic base such as sodium carbonate, potassium carbonate, potassium hydroxide, sodium hydroxide, cesium carbonate, and barium hydroxide. These may be used alone or in combination, in an equivalent amount or in excess.

In addition, solvents that can be used in the reaction include ether solvents such as tetrahydrofuran, dioxane, dichloromethane, and 1,2-dimethoxyethane, aromatic hydrocarbon solvents such as benzene, toluene, and xylene, alcohol-based solvents such as methanol and ethanol, dimethylformamide (DMF), dimethyl sulfoxide (DMSO), acetonitrile, water, and the like. These may be used alone or in combination. The reaction temperature is from 0° C. to the boiling point of the solvent.

In the manufacturing method represented by Scheme 2, Step 4 is a step of obtaining a compound represented by Chemical Formula 2 by reacting the compound represented by Chemical Formula 9 obtained in Step 3. Specifically, this is a step of preparing a carboxylic acid compound represented by Chemical Formula 2 by hydrolyzing the ester compound represented by Chemical Formula 9 under basic or acid conditions.

At this time, the base includes an inorganic base such as sodium carbonate, potassium carbonate, potassium hydroxide, sodium hydroxide, cesium carbonate, and barium hydroxide. These may be used alone or in combination, in an equivalent amount or in excess. The acid includes hydrochloric acid, sulfuric acid, methanesulfonic acid or the like, and the acids may be used alone or in combination, in an equivalent amount or in excess.

In addition, solvents that can be used in the reaction include ether solvents such as tetrahydrofuran, dioxane, dichloromethane, and 1,2-dimethoxyethane, aromatic hydrocarbon solvents such as benzene, toluene, and xylene, alcohol-based solvents such as methanol and ethanol, dimethylformamide (DMF), dimethyl sulfoxide (DMSO), acetonitrile, water, and the like. These may be used alone or in combination. The reaction temperature is from 0° C. to the boiling point of the solvent.

Preparation of the Starting Material (Compound Represented by Chemical Formula 5)

The compound of Chemical Formula 5, which is the starting material of Scheme 2, can be prepared by the manufacturing method shown in Scheme 3 below according to the type of Y.

[Scheme 3]

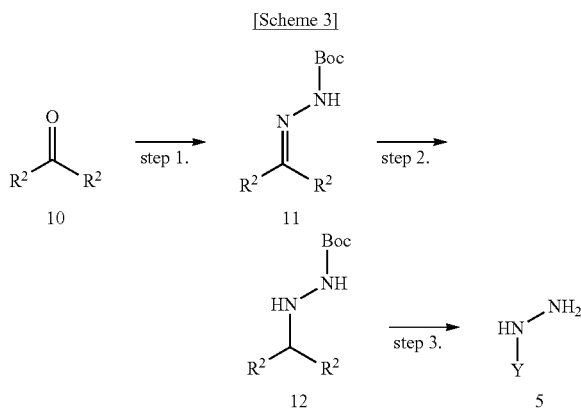

In Scheme 3, Y is as defined in Chemical Formula 1; $R^2$ is a substituent selected from the group consisting of halogen, $C_{1-10}$ linear or branched alkyl unsubstituted or substituted with one or more halogens, $C_{1-10}$ linear or branched alkoxy unsubstituted or substituted with one or more halogens, unsubstituted or substituted $C_{6-10}$ aryl, and unsubstituted or substituted $C_{6-10}$aryloxy, wherein $R_3$ is independently $C_{1-10}$ linear or branched alkyl.

Hereinafter, the manufacturing method represented by Scheme 3 will be described in detail.

In the manufacturing method represented by Reaction Scheme 3, Step 1 is a step of obtaining a compound represented by Chemical Formula 11 by reacting a compound represented by Chemical Formula 10. Specifically, this is a step of preparing an imine compound represented by Chemical Formula 11 by condensation reaction of a ketone compound represented by Chemical Formula 10 and a tert-butyl carbazate.

In addition, solvents that can be used in the reaction include ether solvents such as tetrahydrofuran, dioxane, dichloromethane, and 1,2-dimethoxyethane, aromatic hydrocarbon solvents such as benzene, toluene, and xylene, alcohol-based solvents such as methanol and ethanol, dimethylformamide (DMF), dimethyl sulfoxide (DMSO), acetonitrile, water, and the like. These may be used alone or in combination. The reaction temperature is from 0° C. to the boiling point of the solvent.

In the manufacturing method represented by Scheme 3, Step 2 is a step of obtaining a compound represented by Chemical Formula 12 by reacting the compound represented by Chemical Formula 11 obtained in Step 1. Specifically, this is a step of preparing a hydrazine compound represented by Chemical Formula 12 by reducing reaction of an imine compound represented by Chemical Formula 11 and a metal reducing agent.

The metal reducing agent usable in the above reaction may be sodium borohydride ($NaBH_4$), sodium triacetoxy borohydride ($NaBH(OAc)_3$), or sodium cyanoborohydride ($NaBH_3CN$).

In addition, solvents that can be used in the reaction include ether solvents such as tetrahydrofuran, dioxane, dichloromethane, and 1,2-dimethoxyethane, aromatic hydrocarbon solvents such as benzene, toluene, and xylene, alcohol-based solvents such as methanol and ethanol, dimethylformamide (DMF), dimethyl sulfoxide (DMSO), acetonitrile, water, and the like. These may be used alone or in combination. The reaction temperature is from 0° C. to the boiling point of the solvent.

In the manufacturing method represented by Scheme 3, Step 3 is a step of obtaining a compound represented by Chemical Formula 5 by reacting the compound represented by Chemical Formula 12 obtained in Step 2. Specifically, this step is to prepare the final compound represented by Chemical Formula 5 by removing the amine protecting group of the hydrazine compound represented by Chemical Formula 12 through deprotection reaction.

In the present invention, acid conditions were used, and hydrochloric acid, sulfuric acid, methanesulfonic acid, trifluoroacetic acid, and the like may be used as the acid. In addition, solvents that can be used in the reaction include ether solvents such as tetrahydrofuran, dioxane, dichloromethane, and 1,2-dimethoxyethane, aromatic hydrocarbon solvents such as benzene, toluene, and xylene, alcohol-based solvents such as methanol and ethanol, dimethylformamide (DMF), dimethyl sulfoxide (DMSO), acetonitrile, water, and the like. These may be used alone or in combination. The reaction temperature is from 0° C. to the boiling point of the solvent.

Preparation 1 of the Starting Material (Compound Represented by Chemical Formula 3)

The compound of Chemical Formula 3, which is the starting material of Scheme 1, can be prepared by the manufacturing method shown in Scheme 4 below according to the type of X.

[Scheme 4]

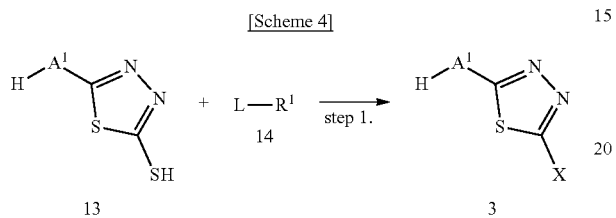

In Scheme 4, $A^1$ is as defined in Chemical Formula 1; X is $SR^1$; L is chloro, bromo or iodine; $R^1$ is as defined in Chemical Formula 1.

Hereinafter, the manufacturing method represented by Scheme 4 will be described in detail.

In the manufacturing method represented by Scheme 3, Step 1 is a step of obtaining a compound represented by Chemical Formula 3 by reacting a compound represented by Chemical Formula 13 with a compound represented by Chemical Formula 14. Specifically, this is a step of preparing a thiadiazole amine compound represented by Chemical Formula 3 by performing a substitution reaction with a thiadiazole thiol compound represented by Chemical Formula 13 and an alkyl halide represented by Chemical Formula 14 under basic conditions.

At this time, the base may be an inorganic base such as sodium carbonate, potassium carbonate, potassium hydroxide, sodium hydroxide, cesium carbonate, barium hydroxide, etc., or an organic base such as piperidine, pyrrolidine, pyridine, triethylamine, N,N-diisopropylethylamine or DBU. These may be used alone or in combination, in an equivalent amount or in excess.

In addition, solvents that can be used in the reaction include ether solvents such as tetrahydrofuran, dioxane, dichloromethane, and 1,2-dimethoxyethane, aromatic hydrocarbon solvents such as benzene, toluene, and xylene, alcohol-based solvents such as methanol and ethanol, dimethylformamide (DMF), dimethyl sulfoxide (DMSO), acetonitrile, water, and the like. These may be used alone or in combination. The reaction temperature is from 0° C. to the boiling point of the solvent.

Preparation 2 of the Starting Material (Compound Represented by Chemical Formula 3)

The compound of Chemical Formula 3, which is the starting material of Scheme 1, can be prepared by the manufacturing method shown in Scheme 5 below according to the type of X.

[Scheme 5]

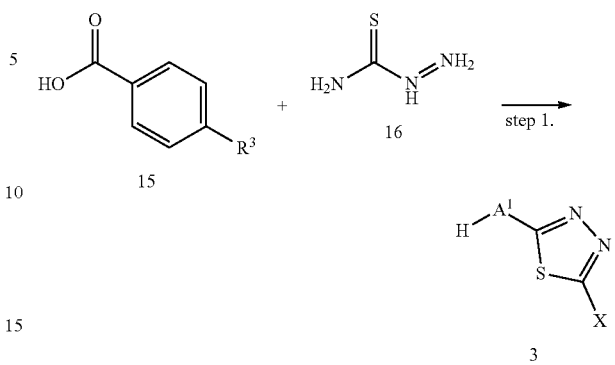

In Scheme 5, $R^3$ is a substituent selected from the group consisting of halogen, $C_{1-10}$ linear or branched alkyl unsubstituted or substituted with one or more halogens, $C_{1-10}$ linear or branched alkoxy unsubstituted or substituted with one or more alkoxy, unsubstituted or substituted $C_{6-10}$aryl and unsubstituted or substituted $C_{6-10}$aryloxy, wherein $R^3$ is independently $C_{1-10}$ linear or branched alkyl.

Hereinafter, the manufacturing method represented by Scheme 5 will be described in detail.

In the manufacturing method represented by Scheme 5, Step 1 is a step of preparing a compound represented by Chemical Formula 3 by reacting a compound represented by Chemical Formula 15 with a compound represented by Chemical Formula 16. Specifically, in this step, a benzonic acid compound represented by Formula 15 is subjected to a cyclization reaction with a thiosemicarbazide compound represented by Chemical Formula 16 in the presence of a chlorination reagent to prepare a compound represented by Chemical Formula 3.

The chlorination reagent usable in the above reaction may be thionyl chloride ($SOCl_2$), phosphonyl chloride ($POCl_3$), or the like.

As the reaction solvent, a water-soluble solvent such as water, an ether solvent such as tetrahydrofuran, dioxane, or 1,2-dimethoxyethane and the like may be used alone or in combination, and the reaction temperature is from 0° C. to the boiling point of the solvent.

In another embodiment, the present invention provides a pharmaceutical composition comprising a therapeutically effective amount of the compound of Chemical Formula 1 according to the present invention or a pharmaceutically acceptable salt thereof, and a pharmaceutically acceptable carrier.

In another embodiment, the present invention provides a method for treating a disease or condition comprising administering a therapeutically effective amount of a compound of Chemical Formula 1 or a pharmaceutically acceptable salt thereof to an individual in need thereof, wherein the disease or condition is a phosphodiesterase 9A related disease.

That is, the present invention provides a medical use, characterized in that the compound of Chemical Formula 1 according to the present invention or a pharmaceutically acceptable salt thereof is used as an active ingredient. In one embodiment, the medical use of the present invention is a phosphodiesterase 9A related disease.

In one embodiment, the phosphodiesterase 9A-related disease is a neurological disease or a mental disease. In one embodiment, the neurological or mental disorder is Alzheimer's disease, Huntington's disease, Lewy body dementia, or Pick's syndrome.

In another embodiment, the phosphodiesterase 9A-related disease is heart failure, particularly cardiac output-preserving heart failure and sickle cell disease.

The compounds of the present invention are generally administered in a therapeutically effective amount. The compounds of the present invention can be administered by any suitable route in the form of a pharmaceutical composition suitable for this route, and in an effective dosage for the intended treatment. Effective dosages are generally about 0.001 to about 100 mg/kg body weight/day, preferably about 0.01 to about 50 mg/kg/day, in single or divided doses. Depending on the age, species, and disease or condition being treated, dosage levels below the lower limit of this range may be suitable. In other cases, still larger dosages can be used without harmful side effects. Larger dosages can be divided into several smaller dosages, for administration throughout the day. Methods for determining an appropriate dosage are well known in the art to which the present invention pertains, and for example, Remington: The Science and Practice of Pharmacy, Mack Publishing Co., 20th ed., 2000 can be used.

For the treatment of the diseases or conditions referred to above, the compounds described herein or pharmaceutically acceptable salts thereof can be administered as follows:

Oral Administration

The compounds of the present disclosure may be administered orally, including by swallowing, so that the compound enters the gastrointestinal tract, or absorbed into the blood stream directly from the mouth (e.g., buccal or sublingual administration).

Suitable compositions for oral administration include solid, liquid, gel or powder formulations, and have a dosage form such as tablet, lozenge, capsule, granule or powder.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include, but are not limited to, lactose, starch, sodium starch glycolate, crospovidone, croscarmellose sodium, maltodextrin, or mixtures thereof.

Suitable lubricants, for use in a tablet, may be present in amounts from about 0.1% to about 5% by weight, and include, but are not limited to, talc, silicon dioxide, stearic acid, calcium, zinc or magnesium stearate, sodium stearyl fumarate and the like.

Suitable binders, for use in a tablet, include, but are not limited to, gelatin, polyethylene glycol, sugars, gums, starch, polyvinyl pyrrolidone, hydroxypropyl cellulose, hydroxypropylmethyl cellulose and the like. Suitable diluents, for use in a tablet, include, but are not limited to, mannitol, xylitol, lactose, dextrose, sucrose, sorbitol, microcrystalline cellulose and starch.

Suitable solubilizers, for use in a tablet, may be present in amounts from about 0.1% to about 3% by weight, and include, but are not limited to, polysorbates, sodium lauryl sulfate, sodium dodecyl sulfate, propylene carbonate, diethyleneglycol monoethyl ether, dimethyl isosorbide, polyethylene glycol (natural or hydrogenated) castor oil, HCOR™ (Nikkol), oleyl ester, Gelucire™, caprylic/caprylic acid mono/diglyceride, sorbitan fatty acid esters, and Solutol HS™.

Parenteral Administration

Compounds of the present disclosure may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release.

Most parenteral formulations are aqueous solutions containing excipients, including salts, buffering agents and isotonic agents.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Topical Administration

Compounds of the present disclosure may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical administration can also be performed by electroporation, iontophoresis, phonophoresis and the like.

Compositions for topical administration may be formulated as immediate or modified release, including delayed or sustained release.

Advantageous Effects

The present invention provides a compound capable of exhibiting various pharmacological activities by inhibiting PDE 9A activity, a pharmaceutical composition containing the compound as an active ingredient, their medical use (especially for treating or alleviating neuropathic diseases and mental diseases), and a method for treating or preventing comprising administering to an individual in need thereof.

MODE FOR INVENTION

The present invention will be described in more detail based on the following examples, but this is not intended to limit the scope of the present invention. In addition, those of ordinary skill in the art will be able to add various modifications and variations to the present invention within the scope not detrimental to the spirit of the present invention.

Preparation Example 1> Preparation of (4,4-difluorocyclohexyl)hydrazine Hydrogen Chloride

Step 1: Preparation of tert-butyl 2-(4,4-difluorocyclohexylidene)hydrazine-1-carboxylate

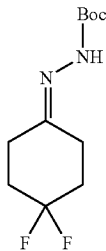

300 mg of 4,4-difluorocyclohexanone (2.24 mmol) was dissolved in 10 ml of hexane, and 296 mg of tert-butyl carbazate (2.24 mmol) was added, followed by stirring under reflux for 3 hours. After completion of the reaction, the mixture was concentrated under reduced pressure to give 550 mg of the title compound (2.24 mmol) in 100% yield.

Rf=0.30 (hexane:ethyl acetate=3:1, v/v)

$^1$H NMR (300 MHz, DMSO-$d_6$) δ 9.72 (br s, 1H), 2.45 (t, J=6.4 Hz, 2H), 2.37 (t, J=6.4 Hz, 2H), 1.99-2.12 (m, 4H), 1.43 (s, 9H)

Step 2: Preparation of tert-butyl 2-(4,4-difluorocyclohexyl)hydrazine-1-carboxylate

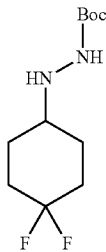

550 mg of tert-butyl 2-(4,4-difluorocyclohexylidene)hydrazine-1-carboxylate obtained in Step 1 was dissolved in in 10 ml of THF, and 950 mg of sodium triacetoxy borohydride (4.48 mmol) was added and stirred at room temperature for 15 hours. After completion of the reaction, the resultant was extracted with 100 ml of ethyl acetate, washed with 100 ml of an inorganic salt solution, dried over anhydrous sodium sulfate ($Na_2SO_4$), and concentrated under reduced pressure. The residue was purified by column chromatography (hexane:ethyl acetate=3:1, v/v) to give 465 mg of the title compound (1.86 mmol) in 84% yield.

Rf=0.45 (hexane:ethyl acetate=3:1, v/v)

$^1$H NMR (300 MHz, DMSO-$d_6$) δ 8.20 (br s, 1H), 4.38 (br s, 1H), 2.86-2.95 (m, 1H), 1.93-2.11 (m, 2H), 1.59-1.83 (m, 4H), 1.41-1.49 (m, 2H), 1.38 (s, 9H)

Step 3: Preparation of (4,4-difluorocyclohexyl)hydrazine hydrogen chloride

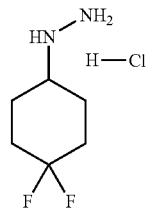

465 mg of tert-butyl 2-(4,4-difluorocyclohexyl)hydrazine-1-carboxylate (1.86 mmol) obtained in Step 2 was dissolved in 10 ml of methanol, and hydrochloric acid was added and stirred at 50° C. for 3 hours. After completion of the reaction, the resultant was concentrated under reduced pressure to give 335 mg of the title compound (1.79 mmol) in 96% yield.

$^1$H NMR (300 MHz, DMSO-$d_6$) δ 3.05-3.12 (m, 1H), 1.96-2.09 (m, 4H), 1.79-1.91 (m, 2H), 1.52-1.59 (m, 2H)

Preparation Example 2> Preparation of 2-((1-(4,4-difluorocyclohexyl)-4-oxo-4,5-dihydro-1H-pyrazolo[3,4-d]pyrimidin-6-yl)thio)acetic acid

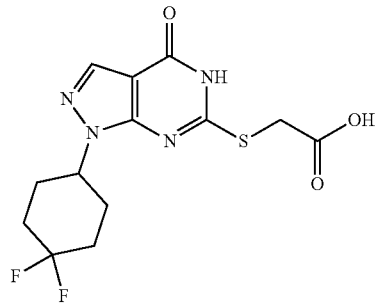 [SMILES: O=C(O)CSc1nc2c(cnn2C2CCC(F)(F)CC2)c(=O)[nH]1]

Step 1: Preparation of 4,6-dichloro-1-(4,4-difluorocyclohexyl)-1H-pyrazolo[3,4-d]pyrimidine

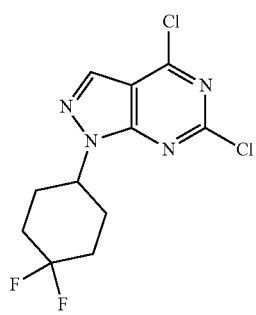 [SMILES: FC1(F)CCC(n2ncc3c(Cl)nc(Cl)nc32)CC1]

340 mg of 2,4,6-trichloropyrimidine-5-carbaldehyde (1.61 mmol) was dissolved in 6 ml of ethanol, and 300 mg of (4,4-difluorocyclohexyl)hydrazine hydrogen chloride (1.61 mmol) obtained in Preparation Example 1 Step 3 and 0.86 ml of N,N-diisopropylethylamine (4.82 mmol) were added at −78° C. and stirred for 3 hours. After completion of the reaction, the resultant was extracted with 100 ml of ethyl acetate, washed with 100 ml of an inorganic salt solution, dried over anhydrous sodium sulfate (Na$_2$SO$_4$), and concentrated under reduced pressure. The residue was purified by column chromatography (hexane:ethyl acetate=10:1, v/v) to give 360 mg of the title compound (1.17 mmol) in 73% yield.

Rf=0.35 (hexane:ethyl acetate=10:1, v/v)
$^1$H NMR (300 MHz, DMSO-d$_6$) δ 8.57 (s, 1H), 4.97-5.04 (m, 1H), 2.13-2.23 (m, 6H), 2.03-2.07 (m, 2H)

Step 2: Preparation of 6-chloro-1-(4,4-difluorocyclohexyl)-1,5-dihydro-4H-pyrazolo[3,4-d]pyrimidin-4-one

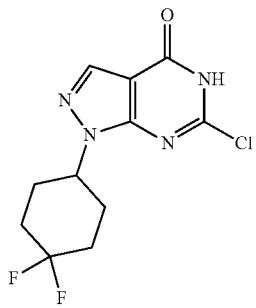 [SMILES: O=c1[nH]c(Cl)nc2c1cnn2C1CCC(F)(F)CC1]

340 mg of 4,6-dichloro-1-(4,4-difluorocyclohexyl)-1H-pyrazolo[3,4-d]pyrimidine (1.11 mmol) prepared in Step 1 above was dissolved in 6 ml of THF, and 1 ml of 2N sodium hydroxide (1.11 mmol) was added, and the mixture was stirred under reflux for 15 hours. After completion of the reaction, the mixture was acidified with 6N hydrochloric acid, and the precipitated solid compound was filtered to give 320 mg of the title compound (1.10 mmol) in 99% yield.

Rf=0.40 (dichloromethane:methanol=20:1, v/v)
$^1$H NMR (500 MHz, DMSO-d$_6$) δ 8.11 (s, 1H), 4.77-4.81 (m, 1H), 2.08-2.17 (m, 6H), 1.94-2.00 (m, 2H)

Step 3: Preparation of ethyl 2-((1-(4,4-difluorocyclohexanyl)-4-oxo-4,5-dihydro-1H-pyrazolo[3,4-d]pyrimidin-6-yl)thio)acetate

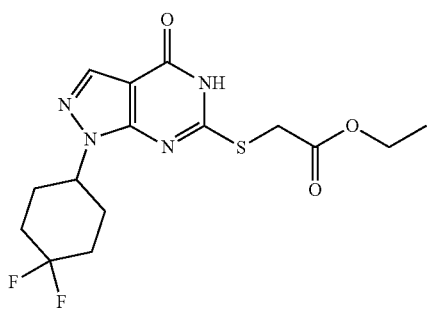 [SMILES: CCOC(=O)CSc1nc2c(cnn2C2CCC(F)(F)CC2)c(=O)[nH]1]

150 mg of 6-chloro-1-(4,4-difluorocyclohexyl)-1,5-dihydro-4H-pyrazolo[3,4-d]pyridin-4-one (0.520 mmol) prepared in Step 2 above, 153 mg of potassium carbonate (1.559 mmol), and 119 μl of ethyl thioglycolate (1.091 mmol) were dissolved in 3 ml DMF, followed by stirring at 90° C. for 3 hours. After completion of the reaction, the resultant was extracted with ethyl acetate and tetrahydrofuran, and washed with water, 1N hydrochloric acid, and saturated brine. The filtrate concentrated under reduced pressure was purified by column chromatography (methanol/dichloromethane=3%, v/v) to give 170 mg of the solid title compound in (0.457 mmol) in 88% yield.

Rf=0.60 (normal hexane:ethyl acetate=1:1, v/v)
$^1$H NMR (300 MHz, MeOD-d$_4$) δ 7.95 (s, 1H), 4.68-4.80 (m, 1H), 4.21 (q, J=7.1 Hz, 2H), 4.09 (s, 2H), 1.92-2.38 (m, 8H), 1.26 (t, J=7.1 Hz, 3H)

Step 4: Preparation of 2-((1-(4,4-difluorocyclohexyl)-4-oxo-4,5-dihydro-1H-pyrazolo[3,4-d]pyrimidin-6-yl)thio)acetic acid

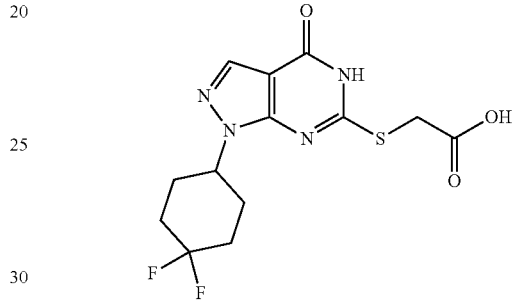

162 mg of ethyl 2-((1-(4,4-difluorocyclohexyl)-4-oxo-4,5-dihydro-1H-pyrazolo[3,4-d]pyrimidin-6-yl)thio)acetate prepared in Step 3 above (0.435 mmol) was dissolved in 3 ml tetrahydrofuran, and 2N sodium hydroxide was added, and the mixture was stirred at room temperature for 1 hour 30 minutes. After completion of the reaction, it was neutralized with 1N hydrochloric acid, extracted with ethyl acetate and tetrahydrofuran, and washed with water and saturated brine. The resultant was concentrated under reduced pressure to give 151 mg of the solid title compound (0.435 mmol) in 99% yield.

$^1$H NMR (500 MHz, DMSO-d$_6$) δ 12.87 (brs, 1H), 12.60 (brs, 1H), 7.98 (s, 1H), 4.65-4.73 (m, 1H), 4.00 (s, 2H), 1.95-2.23 (m, 8H)

<Example 1> Preparation of 2-((1-(4,4-difluorocyclohexyl)-4-oxo-4,5-dihydro-1H-pyrazolo[3,4-d]pyrimidin-6-yl)thio)-N-(5-chloro-1,3,4-thiadiazol-2-yl)acetamide

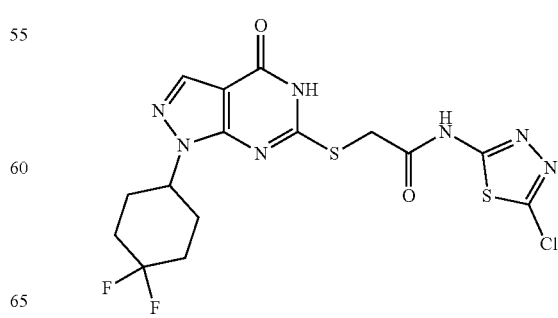

Step 1: Preparation of 2-((1-(4,4-difluorocyclohexyl)-4-oxo-4,5-dihydro-1H-pyrazolo[3,4-d]pyrimidin-6-yl)thio)-N-(5-chloro-1,3,4-thiadiazol-2-yl)acetamide

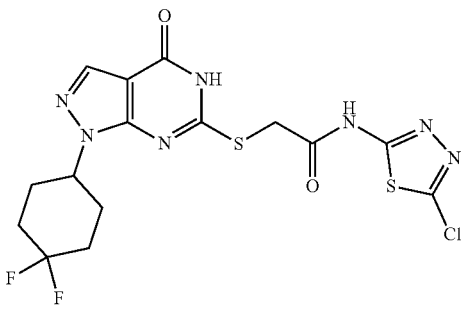 [SMILES: O=C(CSc1nc2c(cnn2C2CCC(F)(F)CC2)c(=O)[nH]1)Nc1nnc(Cl)s1]

40 mg of 2-((1-(4,4-difluorocyclohexyl)-4-oxo-4,5-dihydro-1H-pyrazolo[3,4-d]pyrimidin-6-yl)thio)acetic acid (0.116 mmol) obtained in Preparation Example 2, 24 mg of 5-chloro-1,3,4-thiadiazol-2-amine (0.174 mmol), 59 mg of CMPI (0.232 mmol) were dissolved in 2 ml of DMF, and 41 μl of DIPEA (0.232 mmol) was added and stirred at 50° C. for 16 hours. After completion of the reaction, water was added to precipitate, washed with water and ethyl ether, and filtered to give 12.6 mg of the solid title compound (0.027 mmol) in 24% yield.

$^1$H NMR (300 MHz, DMSO-$d_6$) δ 13.35 (brs, 1H), 12.63 (brs, 1H), 7.97 (s, 1H), 4.47-4.61 (m, 1H), 4.27 (s, 2H), 1.65-2.14 (m, 8H)

Preparation Example 3> Preparation of 2-((4-oxo-1-phenyl-4,5-dihydro-1H-pyrazolo[3,4-d]pyrimidin-6-yl)thio)acetic acid Step 1: Preparation of 4,6-dichloro-1-phenyl-1H-pyrazolo[3,4-d]pyrimidine 2 g of 2,4,6-trichloropyrimidine-5-carbaldehyde (9.44 mmol) was dissolved in 30 ml of ethanol, and 0.9 ml of phenylhydrazine hydrochloride (9.44 mmol) and 4.8 ml of N,N-diisopropylethylamine (28.32 mmol) were added at −78° C. and stirred for 3 hours. After completion of the reaction, the resultant was extracted with 300 ml of ethyl acetate, washed with 200 ml of an inorganic salt solution, dried over anhydrous sodium sulfate (Na$_2$SO$_4$), and concentrated under reduced pressure. The residue was purified by column chromatography (hexane:ethyl acetate=20:1, v/v) to give 1.7 g of the title compound (6.41 mmol) in 68% yield.

Rf=0.50 (hexane:ethyl acetate=10:1, v/v)

$^1$H NMR (300 MHz, CD$_3$OD) δ 8.35 (s, 1H), 8.17 (d, J=8.5 Hz, 2H), 7.59 (dd, J=8.5, 7.6 Hz, 2H), 7.44 (dd, J=7.6, 7.6 Hz, 1H)

Step 2: Preparation of 6-chloro-1-phenyl-1,5-dihydro-4H-pyrazolo[3,4-d]pyrimidin-4-one 1.9 g of 4,6-dichloro-1-phenyl-1H-pyrazolo[3,4-d]pyrimidine (8.98 mmol) prepared in Step 1 above was dissolved in 20 ml of THF, and 10 ml of 2N sodium hydroxide (17.96 mmol) was added and the mixture was stirred under reflux for 15 hours. After completion of the reaction, the mixture was acidified with 6N hydrochloric acid and the precipitated solid compound was filtered to give 2.2 g of the title compound (8.98 mmol) in 99% yield.

Rf=0.23 (dichloromethane:methanol=20:1, v/v)

$^1$H NMR (500 MHz, DMSO-$d_6$) δ 13.47 (br s, 1H), 8.35 (s, 1H), 7.94 (d, J=8.0 Hz, 2H), 7.58 (dd, J=8.0, 7.4 Hz, 2H), 7.43 (dd, J=7.4, 7.4 Hz, 1H)

Step 3: Preparation of ethyl 2-((4-oxo-1-phenyl-4,5-dihydro-1H-pyrazolo[3,4-d]pyrimidin-6-yl)thio)acetate 1 g of 6-chloro-1-phenyl-1,5-dihydro-4H-pyrazolo[3,4-d]pyridin-4-one (4.054 mmol) prepared in Step 2 above and 1.644 g of potassium carbonate (12.162 mmol) were dissolved in 15 ml DMF, 930 μl of ethylthioglycolate (4.514 mmol) was added, followed by stirring at 90° C. for 3 hours and 30 minutes. After completion of the reaction, the resultant was extracted was performed with ethyl acetate and tetrahydrofuran, and washed with water and saturated brine. The filtrate concentrated under reduced pressure was purified by column chromatography (normal hexane:ethyl acetate=3:1->1:1->methanol/dichloromethane=5%, v/v) to give 1.117 g of the solid title compound (3.381 mmol) in 83% yield.

Rf=0.53 (normal hexane:ethyl acetate=1:1, v/v)

$^1$H NMR (300 MHz, MeOD-d4) δ 8.15 (s, 1H), 8.00 (d, J=8.0 Hz, 2H), 7.50-7.57 (m, 2H), 7.36-7.43 (m, 1H), 4.03-4.12 (m, 4H), 1.14 (t, J=7.1 Hz, 3H)

Step 4: Preparation of 2-((4-oxo-1-phenyl-4,5-dihydro-1H-pyrazolo[3,4-d]pyrimidin-6-yl)thio)acetic acid

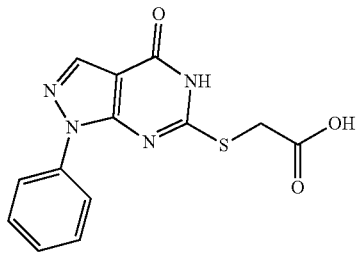 [SMILES: O=C(O)CSc1nc2c(cnn2-c2ccccc2)c(=O)[nH]1]

1.117 g of ethyl 2-((4-oxo-1-phenyl-4,5-dihydro-1H-pyrazolo[3,4-d]pyrimidin-6-yl)thio)acetate (3.381 mmol) prepared in Step 3 above was dissolved in 20 ml of tetrahydrofuran, and 2N sodium hydroxide was added, and the mixture was stirred at room temperature for 1 hour. After completion of the reaction, it was neutralized with 1N hydrochloric acid, extracted with ethyl acetate and tetrahydrofuran, and washed with water and saturated brine. The resultant was concentrated under reduced pressure to give 928 mg of the solid title compound (3.07 mmol) in 91% yield.

$^1$H NMR (300 MHz, DMSO-d$_6$) δ 13.01 (brs, 1H), 12.84 (brs, 1H), 8.25 (s, 1H), 8.05 (d, J=8.2 Hz, 2H), 7.49-7.56 (m, 2H), 7.35-7.42 (m, 1H), 4.03 (s, 2H)

Preparation Example 4> Preparation of 5-(ethylthio)-1,3,4-thiadiazol-2-amine

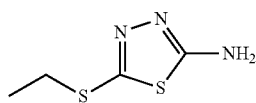

Step 1: Preparation of 5-(ethylthio)-1,3,4-thiadiazol-2-amine

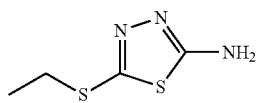

2 g of 5-amino-1,3,4-thiadiazole-2-thiol (15.96 mmol) and 1.01 g of potassium hydroxide (18.02 mmol) were dissolved in 20 ml of isopropyl alcohol and 15 ml of water, and 1.27 ml of iodoethane (15.767 mmol) was slowly added and stirred at room temperature for 4 hours and 60° C. for 1 hour. After completion of the reaction, it was added to 70 ml of ice water and left at 0° C. for 30 minutes. The resulting solid was filtered and washed with water to give 1.238 g of the solid title compound (7.678 mmol) in 48% yield.

$^1$H NMR (300 MHz, CDCl$_3$) δ 5.15 (brs, 2H), 3.18 (q, J=7.4 Hz, 2H), 1.42 (t, J=7.4 Hz, 3H)

<Example 2> Preparation of N-(5-(ethylthio)-1,3,4-thiadiazol-2-yl)-2-((4-oxo-1-phenyl-4,5-dihydro-1H-pyrazolo[3,4-d]pyrimidin-6-yl)thio)acetamide

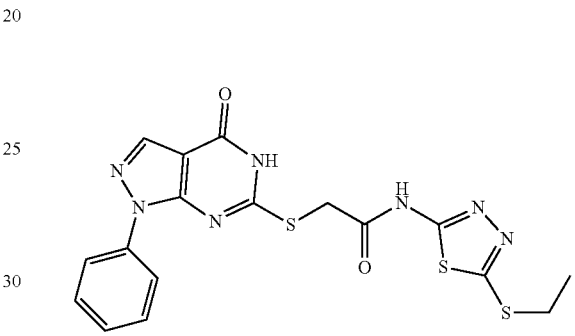

Step 1: Preparation of N-(5-(ethylthio)-1,3,4-thiadiazol-2-yl)-2-((4-oxo-1-phenyl-4,5-dihydro-1H-pyrazolo[3,4-d]pyrimidin-6-yl)thio)acetamide

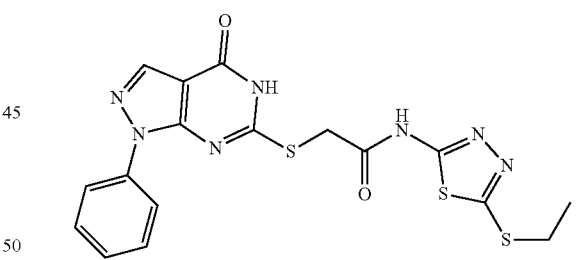

28 mg of 2-((4-oxo-1-phenyl-4,5-dihydro-1H-pyrazolo[3,4-d]pyrimidin-6-yl)thio)acetic acid (0.093 mmol) obtained in Preparation Example 3, 18 mg of 5-(ethylthio)-1,3,4-thiadiazol-2-amine (0.111 mmol) obtained in Preparation Example 4 and 36 mg of 2-chloro-1-methyl-pyridinium iodine (0.140 mmol) were dissolved in 2 ml of DMF, and then 24 μl of DIPEA (0.140 mmol) was added, followed by stirring at room temperature for 16 hours. After completion of the reaction, water was added to precipitate, washed with water and ethyl ether, and filtered to give 21.1 mg of the target solid compound (0.047 mmol) in 51% yield.

$^1$H NMR (300 MHz, DMSO-d$_6$) δ 12.82-13.08 (m 2H), 8.23 (s, 1H), 7.84 (d, J=7.7 Hz, 2H), 7.19-7.35 (m, 3H), 4.31 (s, 2H), 3.19 (q, J=7.2 Hz, 2H), 1.30 (t, J=7.2 Hz, 3H)

<Example 3> Preparation of N-(5-methyl-1,3,4-thiadiazol-2-yl)-2-((4-oxo-1-phenyl-4,5-dihydro-1H-pyrazolo[3,4-d]pyrimidin-6-yl)thio)acetamide

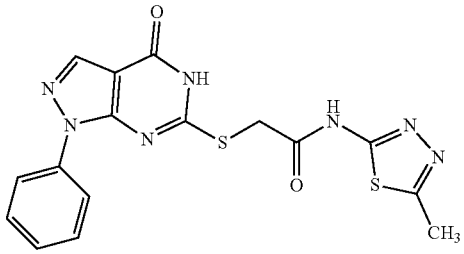 [SMILES: Cc1nnc(NC(=O)CSc2nc3c(cnn3-c3ccccc3)c(=O)[nH]2)s1]

Step 1: Preparation of N-(5-methyl-1,3,4-thiadiazol-2-yl)-2-((4-oxo-1-phenyl-4,5-dihydro-1H-pyrazolo[3,4-d]pyrimidin-6-yl)thio)acetamide

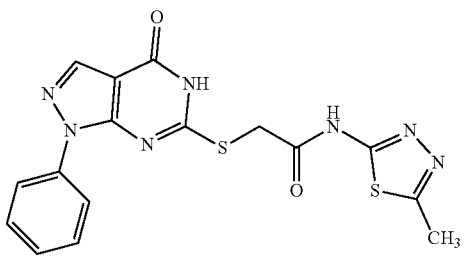 [SMILES: Cc1nnc(NC(=O)CSc2nc3c(cnn3-c3ccccc3)c(=O)[nH]2)s1]

50 mg of 2-((4-oxo-1-phenyl-4,5-dihydro-1H-pyrazolo[3,4-d]pyrimidin-6-yl)thio)acetic acid (0.165 mmol) obtained in Preparation Example 3, 57 mg of 2-amino-5-methyl-1,3,4-thiadiazole (0.496 mmol) and 63 mg of 2-chloro-1-methyl-pyridinium iodine (0.248 mmol) were dissolved in 2 ml of DMF, 43 µl of DIPEA (0.248 mmol) was added, followed by stirring at room temperature for 16 hours. After completion of the reaction, water was added to precipitate, washed with water, ethyl ether, and ethyl acetate, and filtered to give 37 mg of the solid title compound (0.093 mmol) in 56% yield.
$^1$H NMR (300 MHz, DMSO-$d_6$) δ 12.77-12.93 (m, 2H), 8.23 (s, 1H), 7.85 (d, J=7.7 Hz, 2H), 7.20-7.36 (m, 3H), 4.31 (s, 2H), 2.59 (s, 3H)

<Example 4> Preparation of 2-((4-oxo-1-phenyl-4,5-dihydro-1H-pyrazolo[3,4-d]pyrimidin-6-yl)thio)-N-(1,3,4-thiadiazol-2-yl)acetamide

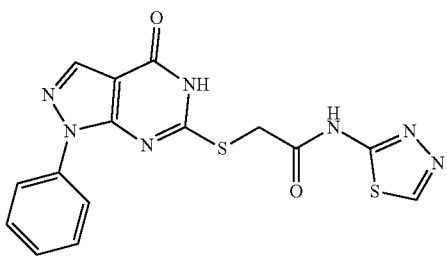 [SMILES: O=C(CSc1nc2c(cnn2-c2ccccc2)c(=O)[nH]1)Nc1nncs1]

Step 1: Preparation of 2-((4-oxo-1-phenyl-4,5-dihydro-1H-pyrazolo[3,4-d]pyrimidin-6-yl)thio)-N-(1,3,4-thiadiazol-2-yl)acetamide

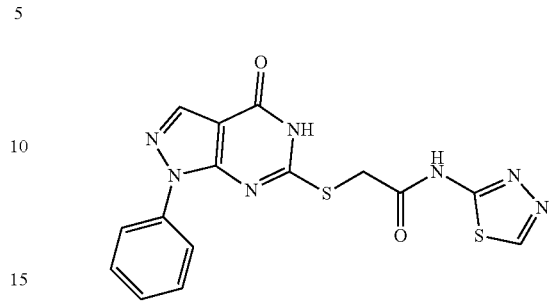

50 mg of 2-((4-oxo-1-phenyl-4,5-dihydro-1H-pyrazolo[3,4-d]pyrimidin-6-yl)thio)acetic acid (0.165 mmol) obtained in Preparation Example 3, 67 mg of 2-amino-1,3,4-thiadiazole (0.660 mmol) and 84 mg of 2-chloro-1-methyl-pyridinium iodine (0.330 mmol) were dissolved in 2 ml of DMF. Then, 58 µl of DIPEA (0.330 mmol) was added, and the mixture was stirred at room temperature for 16 hours. After completion of the reaction, water was added to precipitate, washed with water, ethyl ether, and ethyl acetate, and filtered to give 37.4 mg of the solid title compound (0.097 mmol) in 59% yield.
$^1$H NMR (500 MHz, DMSO-$d_6$) δ 13.00 (brs, 1H), 12.89 (brs, 1H), 9.16 (s, 1H), 8.23 (s, 1H), 7.83 (d, J=7.3 Hz, 2H), 7.24-7.29 (m, 2H), 7.19-7.23 (m, 1H), 4.33 (s, 2H)

<Example 5> Preparation of N-(5-ethyl-1,3,4-thiadiazol-2-yl)-2-((4-oxo-1-phenyl-4,5-dihydro-1H-pyrazolo[3,4-d]pyrimidin-6-yl)thio)acetamide

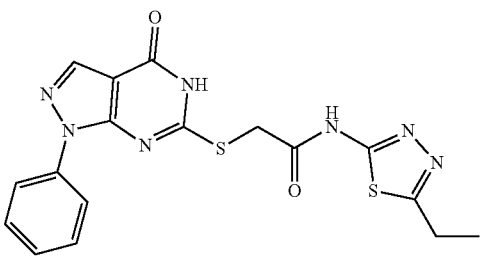 [SMILES: CCc1nnc(NC(=O)CSc2nc3c(cnn3-c3ccccc3)c(=O)[nH]2)s1]

Step 1: Preparation of N-(5-ethyl-1,3,4-thiadiazol-2-yl)-2-((4-oxo-1-phenyl-4,5-dihydro-1H-pyrazolo[3,4-d]pyrimidin-6-yl)thio)acetamide

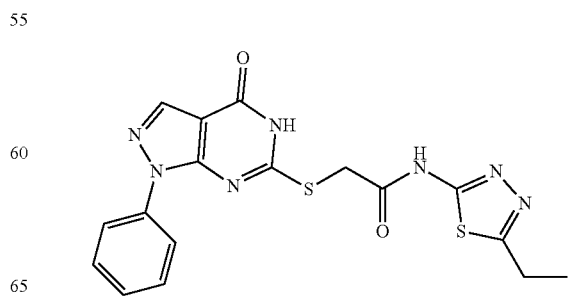

50 mg of 2-((4-oxo-1-phenyl-4,5-dihydro-1H-pyrazolo[3,4-d]pyrimidin-6-yl)thio)acetic acid (0.165 mmol) obtained in Preparation Example 3, 85 mg of 2-amino-5-ethyl-1,3,4-thiadiazole (0.660 mmol) and 84 mg of 2-chloro-1-methyl-pyridinium iodine (0.330 mmol) were dissolved in 2 ml of DMF, and 58 μl of DIPEA (0.330 mmol) was added, followed by stirring at room temperature for 16 hours. After completion of the reaction, water was added to precipitate, washed with water, ethyl ether, and ethyl acetate, and filtered to give 45 mg of the solid title compound (0.109 mmol) in 66% yield.

¹H NMR (500 MHz, DMSO-d₆) δ 12.88 (brs, 1H), 12.82 (brs, 1H), 8.23 (s, 1H), 7.85 (d, J=7.8 Hz, 2H), 7.28-7.33 (m, 2H), 7.21-7.25 (m, 1H), 4.31 (s, 2H)

Preparation Example 5> Preparation of 5-(benzylthio)-1,3,4-thiadiazol-2-amine

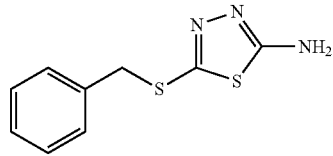 [SMILES: Nc1nnc(SCc2ccccc2)s1]

Step 1: Preparation of 5-(benzylthio)-1,3,4-thiadiazole-2-amine

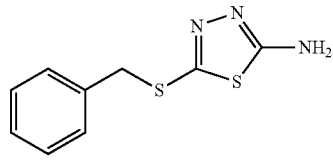 [SMILES: Nc1nnc(SCc2ccccc2)s1]

200 mg of 5-amino-1,3,4-thiadiazole-2-thiol (1.240 mmol) was dissolved in 5 ml of ethanol, and 2N sodium hydroxide and 155 μl of benzyl bromide (1.302 mmol) were added, followed by stirring for 16 hours and 1 hour. After completion of the reaction, the resultant was extracted with ethyl acetate and washed with water and saturated brine. The filtrate concentrated under reduced pressure was purified by column chromatography (methanol/dichloromethane=2%->5%, v/v) to give 254 mg of the solid title compound (1.137 mmol) in 92% yield.

Rf=0.33 (methanol/dichloromethane=5%, v/v)

¹H NMR (500 MHz, DMSO-d₆) δ 7.30-7.37 (m, 4H), 7.24-7.29 (m, 3H), 4.29 (s, 2H)

<Example 6> Preparation of N-(5-(benzylthio)-1,3,4-thiadiazol-2-yl)-2-(4-oxo-1-phenyl-4,5-dihydro-1H-pyrazolo[3,4-d]pyrimidin-6-yl)thio)acetamide

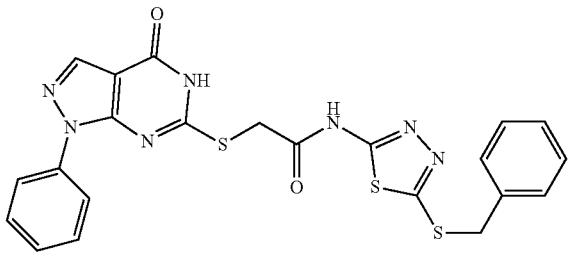 [SMILES: O=C(CSc1nc2c(cnn2-c2ccccc2)c(=O)[nH]1)Nc1nnc(SCc2ccccc2)s1]

Step 1: Preparation of N-(5-(benzylthio)-1,3,4-thiadiazol-2-yl)-2-(4-oxo-1-phenyl-4,5-dihydro-1H-pyrazolo[3,4-d]pyrimidin-6-yl)thio)acetamide

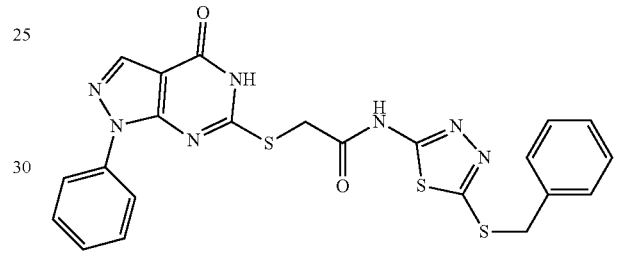

50 mg of 2-((4-oxo-1-phenyl-4,5-dihydro-1H-pyrazolo[3,4-d]pyrimidin-6-yl)thio)acetic acid (0.165 mmol) obtained in Preparation Example 3, 154 mg of 5-(benzylthio)-1,3,4-thiadiazol-2-amine (0.660 mmol) obtained in Preparation Example 5 and 84 mg of 2-chloro-1-methyl-pyridinium iodine (0.330 mmol) were dissolved in 2 ml of DMF, and 58 μl of DIPEA (0.330 mmol) was added, followed by stirring at room temperature for 16 hours. After completion of the reaction, water was added to precipitate, washed with water, ethyl ether, methanol, and ethyl acetate, and filtered to give 44.8 mg of the solid title compound (0.088 mmol) in 53% yield.

¹H NMR (500 MHz, DMSO-d₆) δ 13.03 (brs, 1H), 12.88 (brs, 1H), 8.24 (s, 1H), 7.82 (d, J=7.8 Hz, 2H), 7.33-7.37 (m, 2H), 7.20-7.31 (m, 6H), 4.45 (s, 2H), 4.30 (s, 2H)

<Example 7> Preparation of N-(5-bromo-1,3,4-thiadiazol-2-yl)-2-((4-oxo-1-phenyl-4,5-dihydro-1H-pyrazolo[3,4-d]pyrimidin-6-yl)thio)acetamide

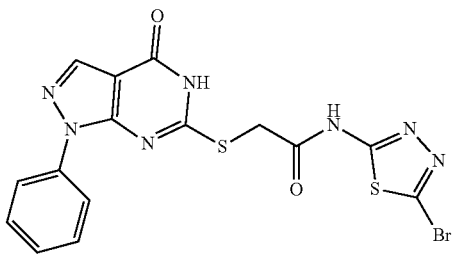 [SMILES: O=C(CSc1nc2c(cnn2-c2ccccc2)c(=O)[nH]1)Nc1nnc(Br)s1]

Step 1: Preparation of N-(5-bromo-1,3,4-thiadiazol-2-yl)-2-((4-oxo-1-phenyl-4,5-dihydro-1H-pyrazolo[3,4-d]pyrimidine-6-yl)thio)acetamide

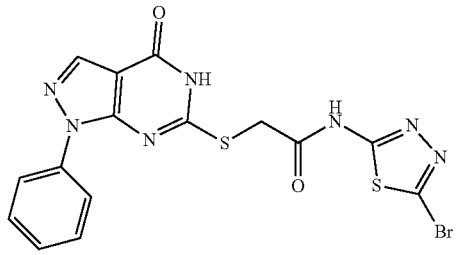 [SMILES: O=C(CSc1nc2c(cnn2-c2ccccc2)c(=O)[nH]1)Nc1nnc(Br)s1]

50 mg of 4-oxo-1-phenyl-4,5-dihydro-1H-pyrazolo[3,4-d]pyrimidin-6-yl)thio)acetic acid (0.165 mmol) obtained in Preparation Example 3, 119 mg of 2-amino-5-bromo-1,3,4-thiadiazole (0.660 mmol) and 84 mg of 2-chloro-1-methyl-pyridinium iodine (0.330 mmol) were dissolved in 2 ml of DMF. After that, 58 μl of DIPEA (0.330 mmol) was added, followed by stirring at room temperature for 16 hours. After completion of the reaction, water was added to precipitate, washed with water, ethyl ether, and ethyl acetate, and filtered to give 25.1 mg of the solid title compound (0.054 mmol) in 33% yield.

$^1$H NMR (500 MHz, DMSO-$d_6$) δ 13.31 (brs, 1H), 12.90 (brs, 1H), 8.23 (s, 1H), 7.83 (d, J=7.8 Hz, 2H), 7.29-7.34 (m, 2H), 7.22-7.26 (m, 1H), 4.34 (s, 2H)

Preparation Example 6> Preparation of 5-((4-chlorobenzyl)thio)-1,3,4-thiadiazol-2-amine

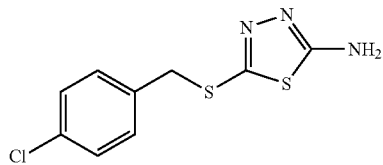 [SMILES: Nc1nnc(SCc2ccc(Cl)cc2)s1]

Step 1: Preparation of 5-((4-chlorobenzyl)thio)-1,3,4-thiadiazol-2-amine

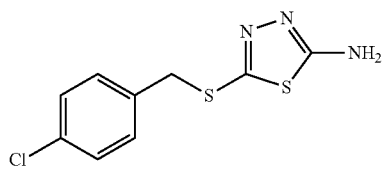 [SMILES: Nc1nnc(SCc2ccc(Cl)cc2)s1]

200 mg of 5-amino-1,3,4-thiadiazole-2-thiol (1.240 mmol) and 268 mg of 4-chlorobenzyl bromide (1.302 mmol) were dissolved in 5 ml of ethanol, and 2N sodium hydroxide was added and stirred at room temperature for 16 hours and 1 hour. After completion of the reaction, the resultant was extracted with ethyl acetate and washed with water and saturated brine. The filtrate concentrated under reduced pressure was purified by column chromatography (methanol/dichloromethane=2%->5%, v/v) to give 187 mg of the solid title compound (0.756 mmol) in 59% yield.

Rf=0.21 (methanol/dichloromethane=5%, v/v)

$^1$H NMR (300 MHz, DMSO-$d_6$) δ 7.33-7.41 (m, 4H), 7.29 (brs, 2H), 4.28 (s, 2H)

<Example 8> Preparation of N-(5-((4-chlorobenzyl)thio)-1,3,4-thiadiazol-2-yl)-2-(4-oxo-1-phenyl-4,5-dihydro-1H-pyrazolo[3,4-d]pyrimidin-6-yl)thio)acetamide

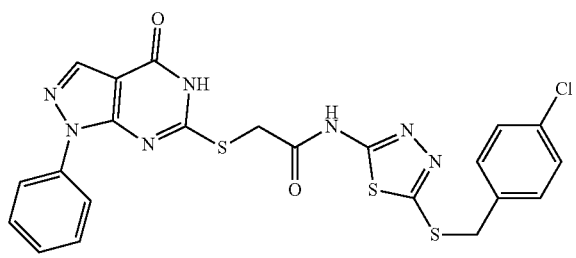 [SMILES: O=C(CSc1nc2c(cnn2-c2ccccc2)c(=O)[nH]1)Nc1nnc(SCc2ccc(Cl)cc2)s1]

Step 1: Preparation of N-(5-((4-chlorobenzyl)thio)-1,3,4-thiadiazol-2-yl)-2-(4-oxo-1-phenyl-4,5-dihydro-1H-pyrazolo[3,4-d]pyrimidin-6-yl)thio)acetamide

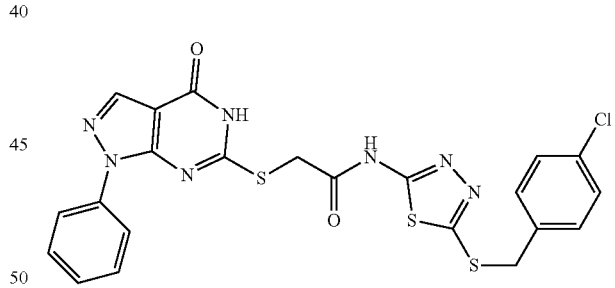

50 mg of 2-((4-oxo-1-phenyl-4,5-dihydro-1H-pyrazolo[3,4-d]pyrimidin-6-yl)thio)acetic acid (0.165 mmol) obtained in Preparation Example 3, 170 mg of 5-((4-chlorobenzyl)thio)-1,3,4-thiadiazol-2-amine (0.660 mmol) obtained in Preparation Example 6 and 84 mg of 2-chloro-1-methyl-pyridinium iodine (0.330 mmol) were dissolved in 2 ml of DMF, 58 μl of DIPEA (0.330 mmol) was added, followed by stirring at room temperature for 16 hours. After completion of the reaction, water was added to precipitate, washed with water, ethyl ether, methanol, and ethyl acetate, and filtered to give 27.5 mg of the solid title compound (0.051 mmol) in 31% yield.

$^1$H NMR (300 MHz, DMSO-$d_6$) δ 12.80-13.11 (m, 2H), 8.23 (s, 1H), 7.82 (d, J=7.4 Hz, 2H), 7.17-7.42 (m, 7H), 4.44 (s, 2H), 4.30 (s, 2H)

Preparation Example 7> Preparation of 5-((4-methylbenzyl)thio)-1,3,4-thiadiazol-2-amine

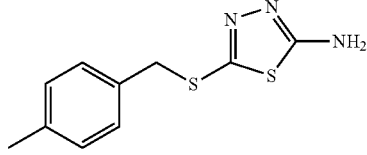

Step 1: Preparation of 5-((4-methylbenzyl)thio)-1,3,4-thiadiazol-2-amine

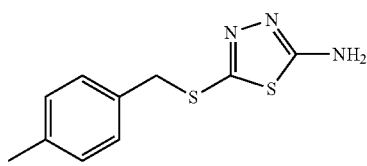

200 mg of 5-amino-1,3,4-thiadiazole-2-thiol (1.240 mmol) and 241 mg of 4-methylbenzyl bromide (1.302 mmol) were dissolved in 5 ml of ethanol, and 2N sodium hydroxide was added and stirred at room temperature for 16 hours and 1 hour. After completion of the reaction, the resultant was extracted with ethyl acetate and washed with water and saturated brine. The filtrate concentrated under reduced pressure was purified by column chromatography (methanol/dichloromethane=2%->5%, v/v) to give 257 mg of the solid title compound (1.083 mmol) in 87% yield.

Rf=0.20 (methanol/dichloromethane=5%, v/v)

$^1$H NMR (300 MHz, DMSO-$d_6$) δ 7.27 (brs, 2H), 7.23 (d, J=8.0 Hz, 2H), 7.12 (d, J=8.0 Hz, 2H), 4.25 (s, 2H), 2.27 (s, 3H)

<Example 9> Preparation of N-(5-((4-methylbenzyl)thio)-1,3,4-thiadiazol-2-yl)-2-(4-oxo-1-phenyl-4,5-dihydro-1H-pyrazolo[3,4-d]pyrimidin-6-yl)thio)acetamide

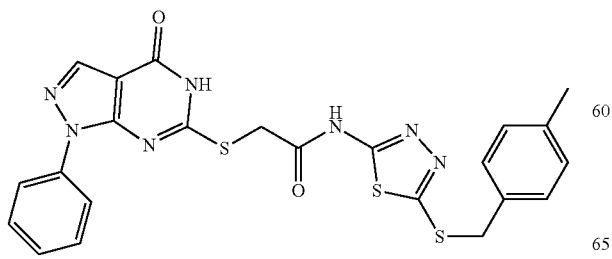

Step 1: Preparation of N-(5-((4-methylbenzyl)thio)-1,3,4-thiadiazol-2-yl)-2-(4-oxo-1-phenyl-4,5-dihydro-1H-pyrazolo[3,4-d]pyrimidin-6-yl)thio)acetamide

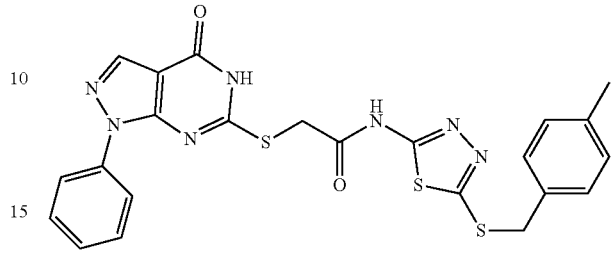

50 mg of 2-((4-oxo-1-phenyl-4,5-dihydro-1H-pyrazolo[3,4-d]pyrimidin-6-yl)thio)acetic acid (0.165 mmol) obtained in Preparation Example 3, 157 mg of 5-((4-methylbenzyl)thio)-1,3,4-thiadiazol-2-amine (0.660 mmol) obtained in Preparation Example 7 and 84 mg of 2-chloro-1-methylpyridinium iodine (0.330 mmol) were dissolved in 2 ml of DMF, 58 µl of DIPEA (0.330 mmol) was added, followed by stirring at room temperature for 16 hours. After completion of the reaction, water was added to precipitate, washed with water, ethyl ether, methanol, and ethyl acetate, and filtered to give 30.6 mg of the solid title compound (0.059 mmol) in 36% yield.

$^1$H NMR (300 MHz, DMSO-$d_6$) δ 12.87-13.06 (m, 2H), 8.24 (s, 1H), 7.81 (d, J=7.4 Hz, 2H), 7.19-7.31 (m, 5H), 7.03 (d, J=7.7 Hz, 2H), 4.40 (s, 2H), 4.29 (s, 2H), 2.20 (s, 3H)

Preparation Example 8> Preparation of 2-((4-oxo-1-phenyl-4,5-dihydro-1H-pyrazolo[3,4-d]pyrimidin-6-yl)thio)propanoic acid

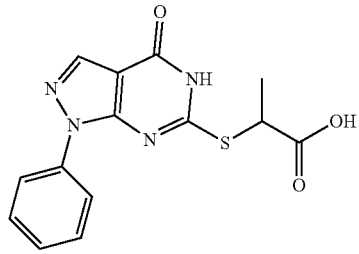 [SMILES: CC(Sc1nc2c(cnn2-c2ccccc2)c(=O)[nH]1)C(=O)O]

Step 1: Preparation of ethyl 2-((4-oxo-1-phenyl-4,5-dihydro-1H-pyrazolo[3,4-d]pyrimidin-6-yl)thio)propanoate

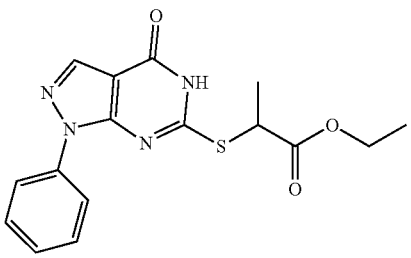 [SMILES: CCOC(=O)C(C)Sc1nc2c(cnn2-c2ccccc2)c(=O)[nH]1]

150 mg of 6-chloro-1-phenyl-1,5-dihydro-4H-pyrazolo[3,4-d]pyridin-4-one (0.608 mmol) prepared in Step 2 of Preparation Example 3 and 252 mg of potassium carbonate (1.824 mmol) were dissolved in 5 ml of DMF, 165 μl of ethyl 2-mercapto propionate (1.277 mmol) was added, followed by stirring at 90° C. for 3 hours and 30 minutes. After completion of the reaction, the resultant was extracted with ethyl acetate and tetrahydrofuran, and washed with water, 1N hydrochloric acid, and saturated brine. The filtrate concentrated under reduced pressure was purified by column chromatography (normal hexane:ethyl acetate=3:1->1:1->methanol/dichloromethane=5%, v/v) to give 154 mg of the solid title compound (0.447 mmol) in 74% yield.

Rf=0.51 (normal hexane:ethyl acetate=1:1, v/v)

$^1$H NMR (300 MHz, CDCl$_3$) δ 10.45 (brs, 1H), 8.22 (s, 1H), 8.04 (d, J=7.8 Hz, 2H), 7.50-7.55 (m, 2H), 7.35-7.40 (m, 1H), 4.58 (q, J=7.3 Hz, 1H), 4.17-4.25 (m, 1H), 4.06-4.13 (m, 1H), 1.71 (d, J=7.3 Hz, 3H), 1.21 (t, J=7.1 Hz, 3H)

Step 2: Preparation of 2-((4-oxo-1-phenyl-4,5-dihydro-1H-pyrazolo[3,4-d]pyrimidin-6-yl)thio)propanoic acid

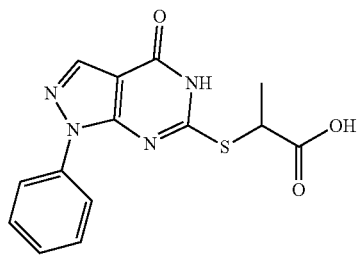 [SMILES: CC(Sc1nc2c(cnn2-c2ccccc2)c(=O)[nH]1)C(=O)O]

146 mg of ethyl 2-((4-oxo-1-phenyl-4,5-dihydro-1H-pyrazolo[3,4-d]pyrimidin-6-yl)thio)propanoate (3.381 mmol) prepared in Step 1 above was dissolved in 5 ml of tetrahydrofuran, 2N sodium hydroxide was added, followed by stirring at room temperature for 4 hours. After completion of the reaction, it was neutralized with 1N hydrochloric acid, extracted with ethyl acetate and tetrahydrofuran, and washed with water and saturated brine. It was concentrated under reduced pressure to give 134 mg of the solid title compound (0.423 mmol) in 99% yield.

$^1$H NMR (300 MHz, DMSO-d$_6$) δ 12.50-13.40 (m, 2H), 8.24 (s, 1H), 8.06 (d, J=7.5 Hz, 2H), 7.50-7.58 (m, 2H), 7.34-7.42 (m, 1H), 4.44 (q, J=7.5 Hz, 1H), 1.58 (d, J=7.5 Hz, 3H)

<Example 10> Preparation of N-(5-methyl-1,3,4-thiadiazol-2-yl)-2-((4-oxo-1-phenyl-4,5-dihydro-1H-pyrazolo[3,4-d]pyrimidin-6-yl)thio)propanamide

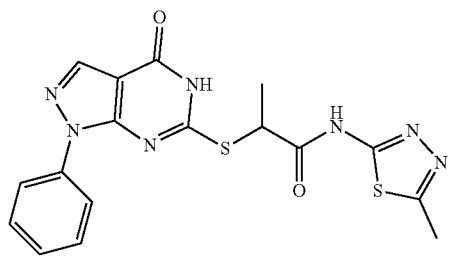 [SMILES: Cc1nnc(NC(=O)C(C)Sc2nc3c(cnn3-c3ccccc3)c(=O)[nH]2)s1]

Step 3: Preparation of N-(5-methyl-1,3,4-thiadiazol-2-yl)-2-((4-oxo-1-phenyl-4,5-dihydro-1H-pyrazolo[3,4-d]pyrimidin-6-yl)thio)propanamide

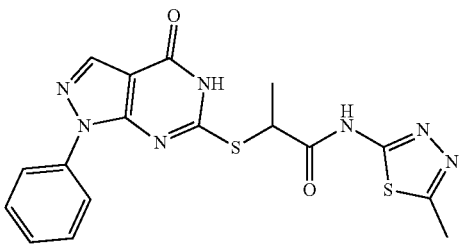 [SMILES: Cc1nnc(NC(=O)C(C)Sc2nc3c(cnn3-c3ccccc3)c(=O)[nH]2)s1]

30 mg of 2-((4-oxo-1-phenyl-4,5-dihydro-1H-pyrazolo[3,4-d]pyrimidin-6-yl)thio)propanoic acid (0.095 mmol) obtained in Preparation Example 8, 22 mg of 2-amino-5-methyl-1,3,4-thiadiazole (0.190 mmol), and 48 mg of BOP-Cl (0.190 mmol) were dissolved in 2 ml of DMF, and 26 μl of TEA (0.190 mmol) was added and stirred at room temperature for 16 hours. After completion of the reaction, the resultant was extracted with ethyl acetate and washed with water and saturated brine. The filtrate concentrated under reduced pressure was purified by column chromatography (hexane:ethyl acetate=1:1->methanol/dichloromethane=5%, v/v) to give 13.6 mg of the solid title compound (0.033 mmol) in 35% yield.

Rf=0.19 (Hex:EA=1:1, v/v)

$^1$H NMR (300 MHz, DMSO-d$_6$) δ 12.80-12.90 (m, 2H), 8.23 (s, 1H), 7.92 (d, J=7.9 Hz, 2H), 7.39-7.47 (m, 2H), 7.26-7.33 (m, 1H), 4.77 (q, J=7.5 Hz, 1H), 2.59 (s, 3H), 1.64 (d, J=7.5 Hz, 3H)

<Example 11> Preparation of N-(5-(ethylthio)-1,3,4-thiadiazol-2-yl)-2-((4-oxo-1-phenyl-4,5-dihydro-1H-pyrazolo[3,4-d]pyrimidin-6-yl)thio)propanamide

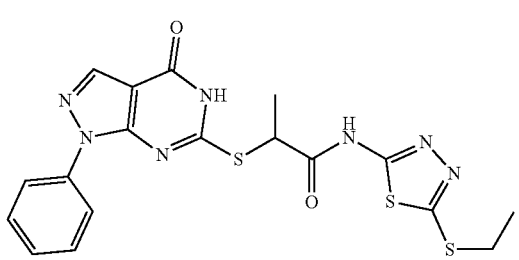 [SMILES: CCSc1nnc(NC(=O)C(C)Sc2nc3c(cnn3-c3ccccc3)c(=O)[nH]2)s1]

Step 1: Preparation of N-(5-(ethylthio)-1,3,4-thiadiazol-2-yl)-2-((4-oxo-1-phenyl-4,5-dihydro-1H-pyrazolo[3,4-d]pyrimidin-6-yl)thio)propanamide

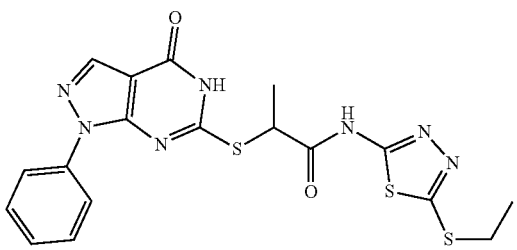 [SMILES: CCSc1nnc(NC(=O)C(C)Sc2nc3c(cnn3-c3ccccc3)c(=O)[nH]2)s1]

40 mg of 2-((4-oxo-1-phenyl-4,5-dihydro-1H-pyrazolo[3,4-d]pyrimidin-6-yl)thio)propanoic acid (0.126 mmol) obtained in Preparation Example 8, 41 mg of 5-(ethylthio)-1,3,4-thiadiazol-2-amine (0.253 mmol) obtained in Preparation Example 4, and 64 mg of BOP-Cl (0.253 mmol) were dissolved in 2 ml of DMF, and 35 μl of TEA (0.253 mmol) was added and stirred at room temperature for 16 hours. After completion of the reaction, the resultant was extracted with ethyl acetate and washed with water and saturated brine. The filtrate concentrated under reduced pressure was purified by column chromatography (hexane:ethyl acetate=1:1->methanol/dichloromethane=5%, v/v) to give 19.8 mg of the solid title compound (0.043 mmol) in 34% yield.

Rf=0.18 (Hex:EA=1:1, v/v)

$^1$H NMR (500 MHz, DMSO-$d_6$) δ 13.07 (brs, 1H), 12.87 (brs, 1H), 8.24 (s, 1H), 7.89 (d, J=7.8 Hz, 2H), 7.39-7.44 (m, 2H), 7.27-7.31 (m, 1H), 4.76 (q, J=7.0 Hz, 1H), 3.20 (q, J=7.3 Hz, 2H), 1.64 (d, J=7.0 Hz, 3H), 1.31 (t, J=7.3 Hz, 3H)

<Example 12> Preparation of N-(5-bromo-1,3,4-thiadiazol-2-yl)-2-((4-oxo-1-phenyl-4,5-dihydro-1H-pyrazolo[3,4-d]pyrimidin-6-yl)thio)propanamide

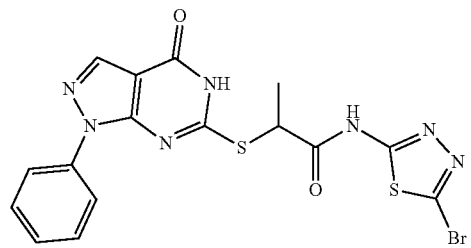 [SMILES: CC(Sc1nc2c(cnn2-c2ccccc2)c(=O)[nH]1)C(=O)Nc1nnc(Br)s1]

Step 1: Preparation of N-(5-bromo-1,3,4-thiadiazol-2-yl)-2-((4-oxo-1-phenyl-4,5-dihydro-1H-pyrazolo[3,4-d]pyrimidin-6-yl)thio)propanamide

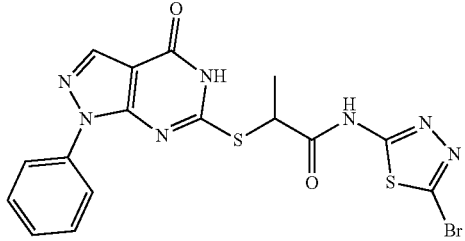 [SMILES: CC(Sc1nc2c(cnn2-c2ccccc2)c(=O)[nH]1)C(=O)Nc1nnc(Br)s1]

40 mg of 2-((4-oxo-1-phenyl-4,5-dihydro-1H-pyrazolo[3,4-d]pyrimidin-6-yl)thio)propanoic acid (0.126 mmol) obtained in Preparation Example 8, 41 mg of 5-(ethylthio)-1,3,4-thiadiazol-2-amine (0.253 mmol), and 64 mg of BOP-Cl (0.253 mmol) were dissolved in 2 ml of DMF. After that, 35 μl of TEA (0.253 mmol) was added, followed by stirring at room temperature for 16 hours. After completion of the reaction, the resultant was extracted with ethyl acetate and washed with water and saturated brine. The filtrate concentrated under reduced pressure was purified by column chromatography (hexane:ethyl acetate=1:1->methanol/dichloromethane=3%, v/v) to give 13.1 mg of the solid title compound (0.027 mmol) in 22% yield.

Rf=0.43 (Hex:EA=1:1, v/v)

$^1$H NMR (300 MHz, DMSO-$d_6$) δ 8.23 (s, 1H), 7.91 (d, J=6.8 Hz, 2H), 7.41-7.49 (m, 2H), 7.27-7.34 (m, 1H), 4.71 (q, J=7.2 Hz, 1H), 1.64 (d, J=7.2 Hz, 3H)

<Example 13> Preparation of N-(5-(methylthio)-1,3,4-thiadiazol-2-yl)-2-((4-oxo-1-phenyl-4,5-dihydro-1H-pyrazolo[3,4-d]pyrimidin-6-yl)thio)acetamide

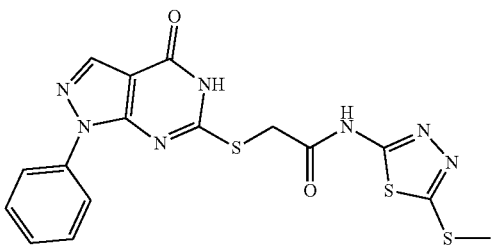 [SMILES: CSc1nnc(NC(=O)CSc2nc3c(cnn3-c3ccccc3)c(=O)[nH]2)s1]

Step 1: Preparation of N-(5-(methylthio)-1,3,4-thiadiazol-2-yl)-2-((4-oxo-1-phenyl-4,5-dihydro-1H-pyrazolo[3,4-d]pyrimidin-6-yl)thio)acetamide

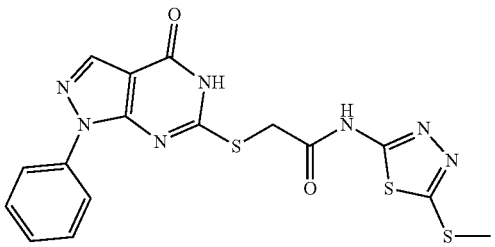 [SMILES: CSc1nnc(NC(=O)CSc2nc3c(cnn3-c3ccccc3)c(=O)[nH]2)s1]

50 mg of 2-((4-oxo-1-phenyl-4,5-dihydro-1H-pyrazolo[3,4-d]pyrimidin-6-yl)thio)acetic acid (0.165 mmol) obtained in Preparation Example 3, 97 mg of 5-(methylthio)-1,3,4-thiadiazol-2-amine (0.660 mmol) and 84 mg of 2-chloro-1-methyl-pyridinium iodine (0.330 mmol) were dissolved in 2 ml of DMF, and 58 μl of DIPEA (0.330 mmol) was added and stirred at room temperature for 16 hours. After completion of the reaction, water was added to precipitate, washed with water and ethyl ether, and filtered to give 56.3 mg of the solid title compound (0.130 mmol) in 79% yield.

$^1$H NMR (300 MHz, DMSO-d$_6$) δ 13.02 (brs, 1H), 12.89 (brs, 1H), 8.24 (s, 1H), 7.84 (d, J=7.7 Hz, 2H), 7.21-7.37 (m, 3H), 4.32 (s, 2H), 2.69 (s, 3H)

Preparation Example 9> Preparation of 5-(isopropylthio)-1,3,4-thiadiazol-2-amine

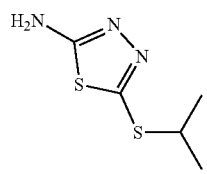

Step 1: Preparation of 5-(isopropylthio)-1,3,4-thiadiazol-2-amine

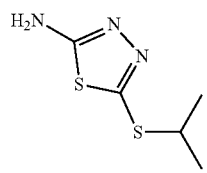

500 mg of 5-amino-1,3,4-thiadiazole-2-thiol (3.754 mmol) and 316 mg of potassium hydroxide (5.631 mmol) was dissolved in 5 ml of isopropyl alcohol and 3 ml of water, and 375 μl of 2-iodopropane (3.754 mmol) was slowly added and stirred at room temperature for 4 hours and 60° C. for 1 hour. After completion of the reaction, it was added to 70 ml of ice water and left at 0° C. for 30 minutes. The resulting solid was filtered and washed with water to give 391 mg of the solid title compound (2.231 mmol) in 59% yield.

$^1$H NMR (300 MHz, DMSO-d$_6$) δ 7.34 (brs, 2H), 3.50 (sep, J=6.6 Hz, 1H), 1.29 (d, J=6.6 Hz, 6H)

<Example 14> Preparation of N-(5-(isopropylthio)-1,3,4-thiadiazol-2-yl)-2-((4-oxo-1-phenyl-4,5-dihydro-1H-pyrazolo[3,4-d]pyrimidin-6-yl)thio)acetamide

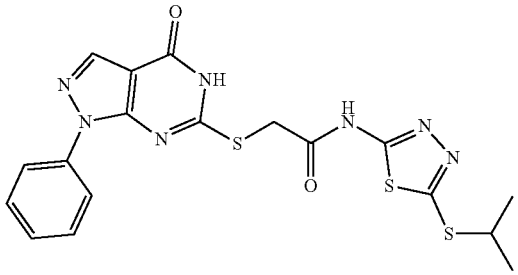 [SMILES: CC(C)Sc1nnc(NC(=O)CSc2nc3c(cnn3-c3ccccc3)c(=O)[nH]2)s1]

Step 1: Preparation of N-(5-(ethylthio)-1,3,4-thiadiazol-2-yl)-2-((4-oxo-1-phenyl-4,5-dihydro-1H-pyrazolo[3,4-d]pyrimidin-6-yl)thio)acetamide

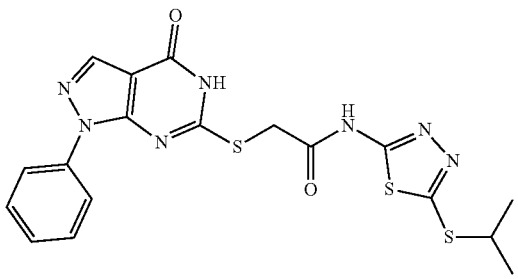 [SMILES: CC(C)Sc1nnc(NC(=O)CSc2nc3c(cnn3-c3ccccc3)c(=O)[nH]2)s1]

50 mg of 2-((4-oxo-1-phenyl-4,5-dihydro-1H-pyrazolo[3,4-d]pyrimidin-6-yl)thio)acetic acid (0.165 mmol) obtained in Preparation Example 3, 116 mg of 5-(isopropyl)-1,3,4-thiadiazol-2-amine (0.660 mmol) obtained in Preparation Example 9 and 84 mg of 2-chloro-1-methyl-pyridinium iodine (0.330 mmol) were dissolved in 2 ml of DMF, and 58 μl of DIPEA (0.330 mmol) was added, followed by stirring at room temperature for 16 hours. After completion of the reaction, water was added to precipitate, washed with water and ethyl ether, and filtered to give 40.9 mg of the solid title compound (0.089 mmol) in 54% yield.

$^1$H NMR (300 MHz, DMSO-d$_6$) δ 13.07 (brs, 1H), 12.99 (brs, 1H), 8.23 (s, 1H), 7.83 (d, J=7.4 Hz, 2H), 7.18-7.33 (m, 3H), 4.32 (s, 2H), 3.66-3.78 (m, 1H), 1.31 (d, J=6.6 Hz, 6H)

Preparation Example 10> Preparation of 5-(propylthio)-1,3,4-thiadiazol-2-amine

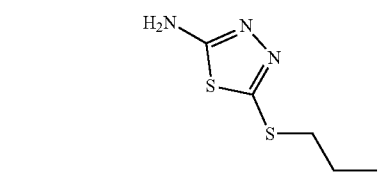

Step 1: Preparation of 5-(propylthio)-1,3,4-thiadiazol-2-amine

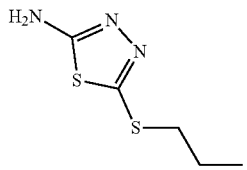

500 mg of 5-amino-1,3,4-thiadiazole-2-thiol (3.754 mmol) and 316 mg of potassium hydroxide (5.631 mmol) were dissolved in 5 ml of isopropyl alcohol and 3 ml of water, 440 µl of 1-iodopropane (4.505 mmol) was slowly added and stirred at room temperature for 4 hours and 60° C. for 1 hour. After completion of the reaction, it was added to 70 ml of ice water and left at 0° C. for 30 minutes. The resulting solid was filtered and washed with water to give 530 mg of the solid title compound (3.024 mmol) in 81% yield.

$^1$H NMR (300 MHz, DMSO-d$_6$) δ 7.34 (brs, 2H), 3.50 (sep, J=6.6 Hz, 1H), 1.29 (d, J=6.6 Hz, 6H)

<Example 15> Preparation of N-(5-(isopropylthio)-1,3,4-thiadiazol-2-yl)-2-((4-oxo-1-phenyl-4,5-dihydro-1H-pyrazolo[3,4-d]pyrimidin-6-yl)thio)acetamide

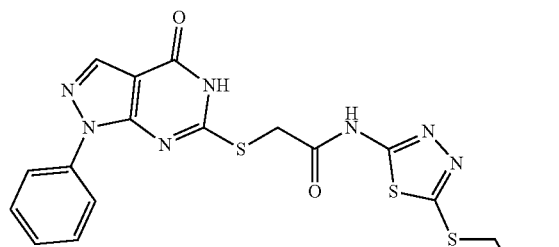

Step 1: Preparation of N-(5-(isopropylthio)-1,3,4-thiadiazol-2-yl)-2-((4-oxo-1-phenyl-4,5-dihydro-1H-pyrazolo[3,4-d]pyrimidin-6-yl)thio)acetamide

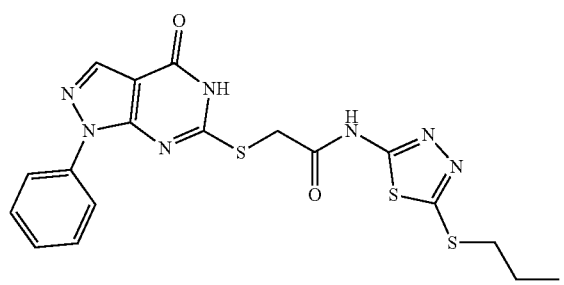 [SMILES: CCCSc1nnc(NC(=O)CSc2nc3c(cnn3-c3ccccc3)c(=O)[nH]2)s1]

50 mg of 2-((4-oxo-1-phenyl-4,5-dihydro-1H-pyrazolo[3,4-d]pyrimidin-6-yl)thio)acetic acid (0.165 mmol) obtained in Preparation Example 3, 116 mg of 5-propyl-1,3,4-thiadiazol-2-amine (0.660 mmol) obtained in Preparation Example 10 and 84 mg of 2-chloro-1-methyl-pyridinium iodine (0.330 mmol) were dissolved in 2 ml of DMF, and 58 µl of DIPEA (0.330 mmol) was added, and stirred at room temperature for 16 hours. After completion of the reaction, water was added to precipitate, washed with water and ethyl ether, and filtered to give 40.9 mg of the solid title compound (0.089 mmol) in 54% yield.

$^1$H NMR (300 MHz, DMSO-d$_6$) δ 13.07 (brs, 1H), 12.99 (brs, 1H), 8.23 (s, 1H), 7.83 (d, J=7.4 Hz, 2H), 7.18-7.33 (m, 3H), 4.32 (s, 2H), 3.66-3.78 (m, 1H), 1.31 (d, J=6.6 Hz, 6H)

Preparation Example 11> Preparation of 2-((1-(4-fluorophenyl)-4-oxo-4,5-dihydro-1H-pyrazolo[3,4-d]pyrimidin-6-yl)thio)acetic acid

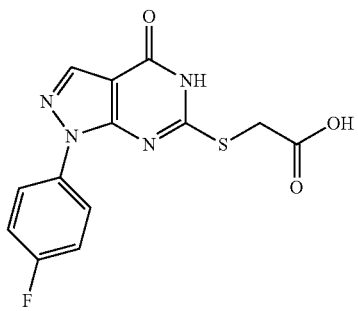 [SMILES: O=C(O)CSc1nc2c(cnn2-c2ccc(F)cc2)c(=O)[nH]1]

Step 1: Preparation of ethyl 2-((1-(4-fluorophenyl)-4-oxo-4,5-dihydro-1H-pyrazolo[3,4-d]pyrimidin-6-yl)thio)acetate

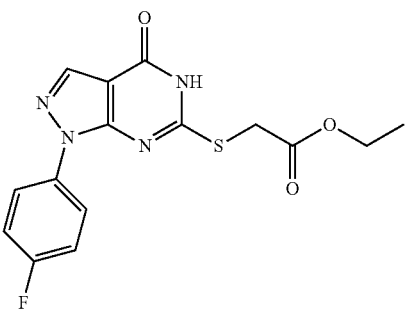 [SMILES: CCOC(=O)CSc1nc2c(cnn2-c2ccc(F)cc2)c(=O)[nH]1]

100 mg of 6-chloro-1-(4-fluorophenyl)-1,5-dihydro-4H-pyrazolo[3,4-d]pyridin-4-one (0.378 mmol), 153 mg of potassium carbonate (2.232 mmol), and 87 µl of ethyl thioglycolate (0.794 mmol) were dissolved in 3 ml of DMF, followed by stirring at 90° C. for 3 hours. After completion of the reaction, the resultant was extracted with ethyl acetate and tetrahydrofuran, followed by washing with water, 1N hydrochloric acid, and saturated brine. The filtrate concentrated under reduced pressure was purified by column chromatography (methanol/dichloromethane=3%, v/v) to give 106 mg of the solid title compound (0.304 mmol) in 81% yield.

Rf=0.68 (normal hexane:ethyl acetate=1:1, v/v)

$^1$H NMR (500 MHz, DMSO-d$_6$) δ 12.86 (brs, 1H), 8.25 (s, 1H), 7.99-8.04 (m, 2H), 7.34-7.40 (m, 2H), 4.12 (s, 2H), 4.00 (q, J=6.9 Hz, 2H), 1.05 (t, J=6.9 Hz, 3H)

Step 2: Preparation of 2-((1-(4-fluorophenyl)-4-oxo-4,5-dihydro-1H-pyrazolo[3,4-d]pyrimidin-6-yl)thio)acetic acid

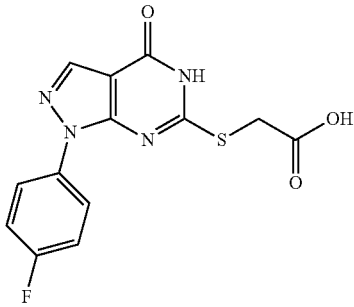 [SMILES: O=C(O)CSc1nc2c(cnn2-c2ccc(F)cc2)c(=O)[nH]1]

101 mg of ethyl 2-((1-(4-fluorophenyl)-4-oxo-4,5-dihydro-1H-pyrazolo[3,4-d]pyrimidin-6-yl)thio)acetate (0.290 mmol) obtained in Step 1 was dissolved in 3 ml of tetrahydrofuran, and 2N sodium hydroxide was added, followed by stirring at room temperature for 16 hours. After completion of the reaction, it was neutralized with 1N hydrochloric acid, extracted with ethyl acetate and tetrahydrofuran, and washed with water and saturated brine. The resultant was concentrated under reduced pressure to give 63 mg of the solid title compound (0.197 mmol) in 68% yield.
$^1$H NMR (300 MHz, DMSO-$d_6$) δ 12.98 (brs, 1H), 12.84 (brs, 1H), 8.25 (s, 1H), 8.01-8.09 (m, 2H), 7.30-7.39 (m, 2H), 4.02 (s, 2H)

<Example 16> Preparation of N-(5-(ethylthio)-1,3,4-thiadiazol-2-yl)-2-((1-(4-fluorophenyl)-4-oxo-4,5-dihydro-1H-pyrazolo[3,4-d]pyrimidin-6-yl)thio) acetamide

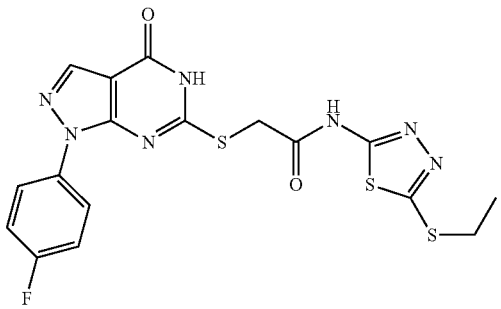 [SMILES: CCSc1nnc(NC(=O)CSc2nc3c(cnn3-c3ccc(F)cc3)c(=O)[nH]2)s1]

Step 1: Preparation of N-(5-(ethylthio)-1,3,4-thiadiazol-2-yl)-2-((1-(4-fluorophenyl)-4-oxo-4,5-dihydro-1H-pyrazolo[3,4-d]pyrimidin-6-yl)thio)acetamide

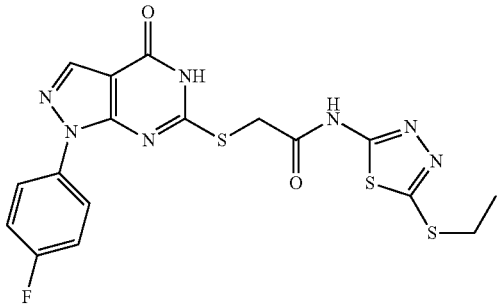 [SMILES: CCSc1nnc(NC(=O)CSc2nc3c(cnn3-c3ccc(F)cc3)c(=O)[nH]2)s1]

30 mg of 2-((1-(4-fluorophenyl)-4-oxo-4,5-dihydro-1H-pyrazolo[3,4-d]pyrimidin-6-yl)thio)acetic acid (0.094 mmol) obtained in Preparation Example 11, 61 mg of 5-(ethylthio)-1,3,4-thiadiazole-2-amine (0.376 mmol) obtained in Preparation Example 3, and 48 mg of CMPI (0.187 mmol) were dissolved in 2 ml of DMF, and 33 μl of DIPEA (0.187 mmol) was added, and stirred at room temperature for 16 hours. After completion of the reaction, water was added to precipitate, washed with water and ethyl ether, and filtered to give 9.4 mg of the solid title compound (0.020 mmol) in 22% yield.
$^1$H NMR (300 MHz, DMSO-$d_6$) δ 12.82-13.04 (m, 2H), 8.23 (s, 1H), 7.65 (dd, 7=13.6, 8.8 Hz, 2H), 7.13 (dd, J=8.8, 8.8 Hz, 2H), 4.30 (s, 2H), 3.19 (q, 7=7.1 Hz, 2H), 1.30 (t, 7=7.1 Hz, 3H)

<Example 17> Preparation of N-(5-bromo-1,3,4-thiadiazol-2-yl)-2-((1-(4-fluorophenyl)-4-oxo-4,5-dihydro-1H-pyrazolo[3,4-d]pyrimidin-6-yl)thio) acetamide

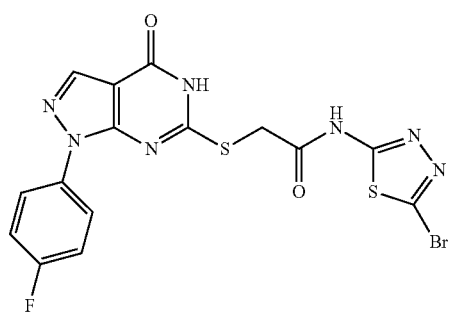 [SMILES: O=C(CSc1nc2c(cnn2-c2ccc(F)cc2)c(=O)[nH]1)Nc1nnc(Br)s1]

Step 1: Preparation of N-(5-bromo-1,3,4-thiadiazol-2-yl)-2-((1-(4-fluorophenyl)-4-oxo-4,5-dihydro-1H-pyrazolo[3,4-d]pyrimidin-6-yl)thio)acetamide

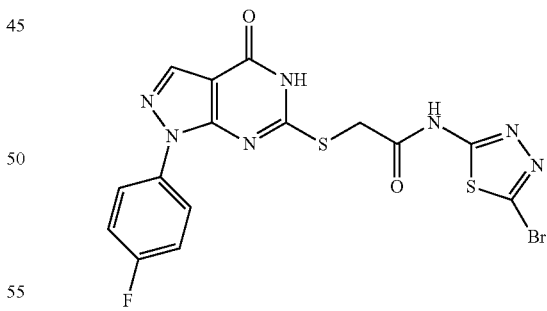

30 mg of 2-((1-(4-fluorophenyl)-4-oxo-4,5-dihydro-1H-pyrazolo[3,4-d]pyrimidin-6-yl)thio)acetic acid (0.094 mmol) obtained in Preparation Example 11, 68 mg of 5-bromo-1,3,4-thiadiazole-2-amine (0.376 mmol), and 48 mg of CMPI (0.187 mmol) were dissolved in 2 ml of DMF. Then, 33 μl of DIPEA (0.187 mmol) was added, followed by stirring at room temperature for 16 hours. After completion of the reaction, water was added to precipitate, washed with water and ethyl ether, and filtered to give 9.4 mg of the solid title compound (0.020 mmol) in 22% yield.

$^1$H NMR (300 MHz, DMSO-$d_6$) δ 13.25 (brs, 1H), 12.91 (brs, 1H), 8.23 (s, 1H), 7.64 (dd, J=13.8, 8.8 Hz, 2H), 7.15 (dd, J=8.8, 8.5 Hz, 2H), 4.33 (s, 2H)

<Example 18> Preparation of N-(5-(ethylthio)-1,3,4-thiadiazol-2-yl)-N-methyl-2-((4-oxo-1-phenyl-4,5-dihydro-1H-pyrazolo[3,4-d]pyrimidin-6-yl)thio)acetamide

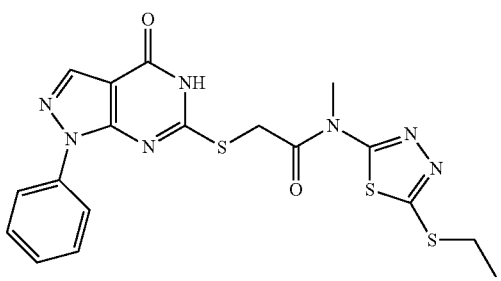 [SMILES: CCSc1nnc(N(C)C(=O)CSc2nc3c(cnn3-c3ccccc3)c(=O)[nH]2)s1]

Step 1: Preparation of N-(5-(ethylthio)-1,3,4-thiadiazol-2-yl)-N-methyl-2-((4-oxo-1-phenyl-4,5-dihydro-1H-pyrazolo[3,4-d]pyrimidin-6-yl)thio)acetamide

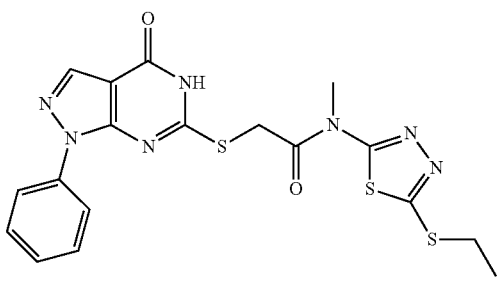 [SMILES: CCSc1nnc(N(C)C(=O)CSc2nc3c(cnn3-c3ccccc3)c(=O)[nH]2)s1]

35 mg of 2-((4-oxo-1-phenyl-4,5-dihydro-1H-pyrazolo[3,4-d]pyrimidin-6-yl)thio)acetic acid (0.114 mmol) obtained in Preparation Example 3, 60 mg of 5-(methylthio)-N-methyl-1,3,4-thiadiazol-2-amine (0.342 mmol)) and 58 mg of 2-chloro-1-methyl-pyridinium iodine (0.228 mmol) were dissolved in 2 ml of DMF, and 40 μl of DIPEA (0.228 mmol) was added, followed by stirring at room temperature for 16 hours. After completion of the reaction, water was added to precipitate, washed with water and ethyl ether, and filtered to give 31.3 mg of the solid title compound (0.068 mmol) in 60% yield.

$^1$H NMR (300 MHz, DMSO-$d_6$) δ 12.92 (brs, 1H), 8.24 (s, 1H), 7.73-7.80 (m, 2H), 7.22-7.29 (m, 3H), 4.68 (s, 2H), 3.81 (s, 3H), 3.19 (q, J=7.1 Hz, 2H), 1.30 (t, J=7.1 Hz, 3H)

<Example 19> Preparation of 2-((1-(4,4-difluorocyclohexyl)-4-oxo-4,5-dihydro-1H-pyrazolo[3,4-d]pyrimidine-6-yl)thio)-N-(5-(ethylthio)-1,3,4-thiadiazol-2-yl)acetamide

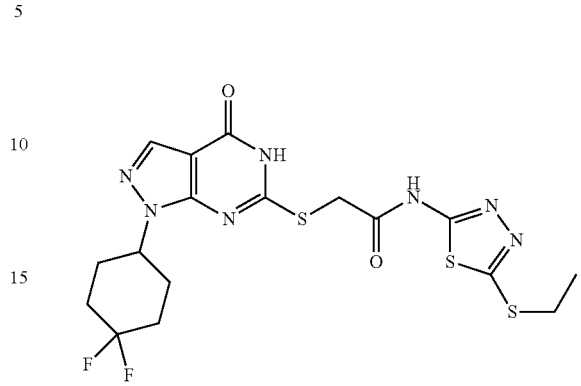

Step 1: Preparation of 2-((1-(4,4-difluorocyclohexyl)-4-oxo-4,5-dihydro-1H-pyrazolo[3,4-d]pyrimidin-6-yl)thio)-N-(5-(ethylthio)-1,3,4-thiadiazol-2-yl)acetamide

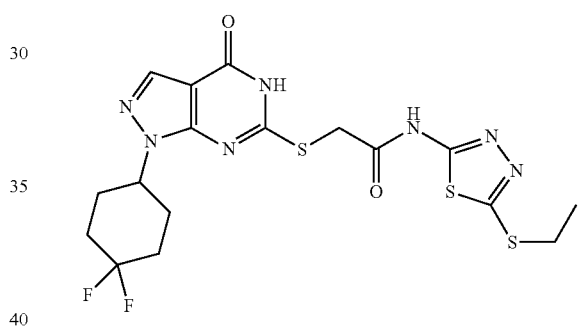

40 mg of 2-((1-(4,4-difluorocyclohexyl)-4-oxo-4,5-dihydro-1H-pyrazolo[3,4-d]pyrimidine-6-yl)thio)acetic acid (0.116 mmol) obtained in Preparation Example 2, 56 mg of 5-(ethylthio)-1,3,4-thiadiazole-2-amine (0.348 mmol) obtained in Preparation Example 4, and 88 mg of HATU (0.232 mmol) were dissolved in 2 ml of DMF, and 41 μl of DIPEA (0.232 mmol) was added, followed by stirring at room temperature for 16 hours. After completion of the reaction, water was added to precipitate, washed with water and ethyl ether, and filtered to give 21 mg of the solid title compound (0.043 mmol) in 22% yield.

$^1$H NMR (300 MHz, DMSO-$d_6$) δ 13.09 (brs, 1H), 12.62 (brs, 1H), 7.96 (s, 1H), 4.46-4.55 (m, 1H), 4.24 (s, 2H), 3.21 (q, J=7.1 Hz, 2H), 1.66-2.01 (m, 8H), 1.32 (t, J=7.1 Hz, 3H)

Preparation Example 12> Preparation of 5-(p-tolyl)-1,3,4-thiadiazol-2-amine

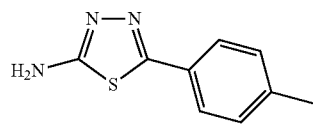

Step 1: Preparation of
5-(p-tolyl)-1,3,4-thiadiazol-2-amine

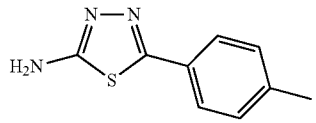

Para-toluic acid (500 mg, 3.67 mmol) was dissolved in an excess of phosphoryl chloride, and thiosemicarbazide (1.004 g, 11.02 mmol) was added. After 2 hours reaction at 75° C., the mixture was cooled. After water was added, it was boiled for 4 hours and cooled. After recrystallization with 50% potassium hydroxide aqueous solution and filtration, 677 mg (3.52 mmol) was obtained in 96% yield.
Rf=0.45 (EA:HEX=1:10)
$^1$H NMR (300 MHz, DMSO-$d_6$) δ 7.83 (br s, 2H), 7.80 (d, J=8.0 Hz, 2H), 7.44 (d, J=8.0 Hz, 2H), 2.66 (s, 3H)

<Example 20> Preparation of 2-((4-oxo-1-phenyl-4, 5-dihydro-1H-pyrazolo[3,4-d]pyrimidin-6-yl)thio)-N-(5-(p-tolyl)-1,3,4-thiadiazol-2-yl)propanamide

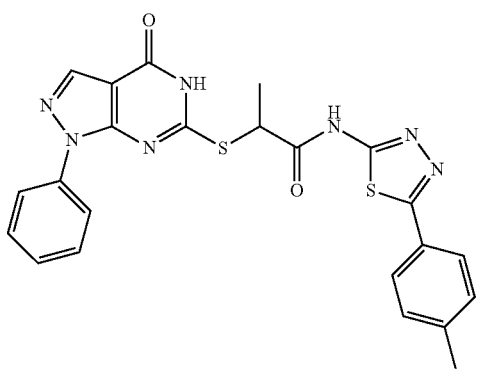 [SMILES: Cc1ccc(-c2nnc(NC(=O)C(C)Sc3nc4c(cnn4-c4ccccc4)c(=O)[nH]3)s2)cc1]

Step 1: Preparation of 2-((4-oxo-1-phenyl-4,5-dihydro-1H-pyrazolo[3,4-d]pyrimidin-6-)thio)-N-(5-(p-tolyl)-1,3,4-thiadiazol-2-yl)propanamide

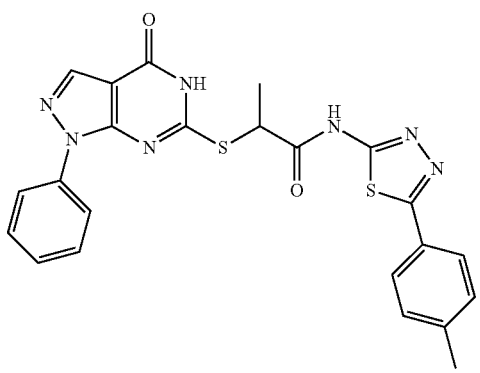 [SMILES: Cc1ccc(-c2nnc(NC(=O)C(C)Sc3nc4c(cnn4-c4ccccc4)c(=O)[nH]3)s2)cc1]

2-((4-oxo-1-phenyl-4,5-dihydro-1H-pyrazolo[3,4-d]pyrimidin-6-yl)thio)propanoic acid (40 mg, 0.165 mmol) obtained in Preparation Example 8 was dissolved in dimethylformamide, and 5-(p-tolyl)-1,3,4-thiadiazol-2-amine (101 mg, 0.661 mmol) obtained in Preparation Example 12, HATU (50 mg, 0.33 mmol), HOAT (36 mg, 0.33 mmol), and DIPEA (47 μl, 0.33 mmol) were added. A white solid was formed when cold water is added after reacting at room temperature for more than 12 hours. The solid was filtered and then subjected to column chromatography (MeOH/MC 5%) to give 10 mg (0.021 mmol) in 16% yield.
Rf=0.20 (EA:HEX=2:1)
$^1$H NMR (300 MHz, DMSO-$d_6$) δ 13.03 (br s, 1H), 12.92 (br s, 1H), 8.23 (s, 1H), 7.91 (d, J=7.7 Hz, 2H), 7.79 (d, J=7.7 Hz, 2H), 7.40-7.45 (m, 2H), 7.28-7.34 (m, 3H), 4.79 (q, J=7.4 Hz, 1H), 2.35 (s, 1H), 1.65 (d, J=7.4 Hz, 3H)

<Example 21> Preparation of 2-((1-(4,4-difluorocyclohexyl)-4-oxo-4,5-dihydro-1H-pyrazolo[3,4-d]pyrimidin-6-yl)thio)-N-(5-bromo-1,3,4-thiadiazol-2-yl)acetamide

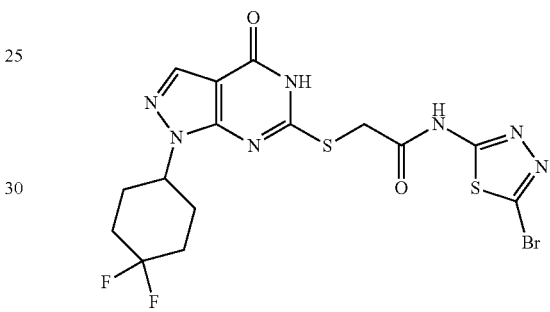

Step 1: Preparation of 2-((1-(4,4-difluorocyclohexyl)-4-oxo-4,5-dihydro-1H-pyrazolo[3,4-d]pyrimidin-6-yl)thio)-N-(5-bromo-1,3,4-thiadiazol-2-yl)acetamide

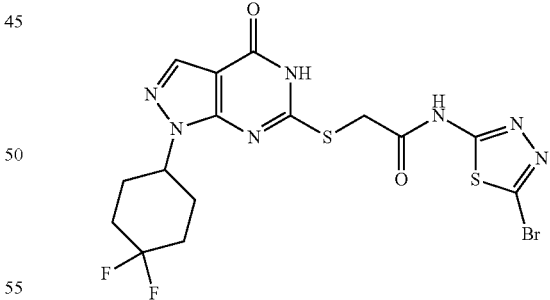

40 mg of 2-((1-(4,4-difluorocyclohexyl)-4-oxo-4,5-dihydro-1H-pyrazolo[3,4-d]pyrimidine-6-yl)thio)acetic acid (0.116 mmol) obtained in Example 2, 65 mg of 5-bromo-1,3,4-thiadiazol-2-amine (0.348 mmol), and 41 mg of CDMT (0.232 mmol) were dissolved in 2 ml of DMF, 26 μl of NMM (0.232 mmol) was added, followed by stirring at room temperature for 16 hours. After completion of the reaction, the resultant was extracted with ethyl acetate and washed with water and saturated brine. The filtrate concentrated under reduced pressure was purified by column chromatography (hexane:ethyl acetate=1:1->methanol/dichloromethane 5%) to give 14 mg of the solid title compound (0.028 mmol) in 24% yield.

Rf=0.47 (methanol/dichloromethane=10%, v/v)

$^1$H NMR (500 MHz, MeOD-d$_4$) δ 7.94 (s, 1H), 4.57-4.62 (m, 1H), 4.24 (s, 2H), 1.74-2.19 (m, 8H)

<Example 22> Preparation of N-(5-(tertiary-butyl)-1,3,4-thiadiazol-2-yl)-2-((4-oxo-1-phenyl-4,5-dihydro-1H-pyrazolo[3,4-d]pyrimidin-6-yl)thio)acetamide

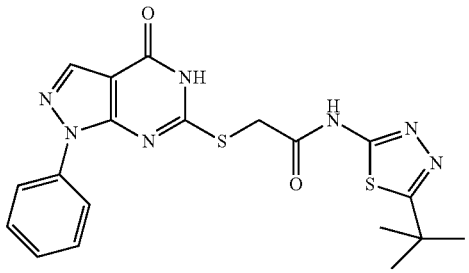 [SMILES: CC(C)(C)c1nnc(NC(=O)CSc2nc3c(cnn3-c3ccccc3)c(=O)[nH]2)s1]

Step 1: Preparation of N-(5-(tertiary-butyl)-1,3,4-thiadiazol-2-yl)-2-((4-oxo-1-phenyl-4,5-dihydro-1H-pyrazolo[3,4-d]pyrimidin-6-yl)thio)acetamide

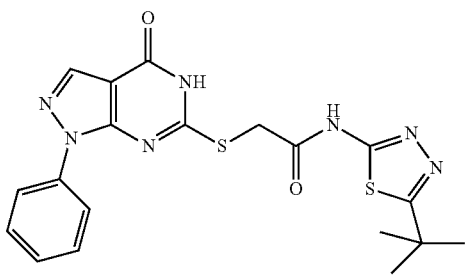 [SMILES: CC(C)(C)c1nnc(NC(=O)CSc2nc3c(cnn3-c3ccccc3)c(=O)[nH]2)s1]

40 mg of 2-((4-oxo-1-phenyl-4,5-dihydro-1H-pyrazolo[3,4-d]pyrimidin-6-yl)thio)acetic acid (0.132 mmol) obtained in Preparation Example 3, 62 mg of 5-tertiarybutyl-1,3,4-thiadiazol-2-amine (0.397 mmol) and 67 mg of 2-chloro-1-methyl-pyridinium iodine (0.264 mmol) were dissolved in 2 ml of DMF, and 46 μl of DIPEA (0.264 mmol) was added, and stirred at room temperature for 16 hours. After completion of the reaction, water was added to precipitate, washed with water and ethyl ether, and filtered to give 23.5 mg of the solid title compound (0.053 mmol) in 40% yield.

$^1$H NMR (300 MHz, DMSO-d$_6$) δ 12.77-12.92 (m, 2H). 8.23 (s, 1H), 7.84 (d, J=7.4 Hz, 2H), 7.17-7.31 (m, 3H), 4.29 (s, 2H), 1.37 (s, 9H)

Preparation Example 13> Preparation of 5-(4-fluorophenyl)-1,3,4-thiadiazol-2-amine

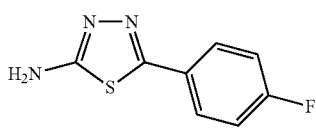

Step 1: Preparation of 5-(4-fluorophenyl)-1,3,4-thiadiazol-2-amine

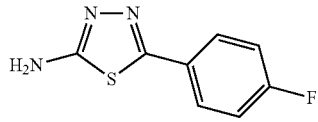 [SMILES: Nc1nnc(-c2ccc(F)cc2)s1]

After dissolving 4-fluorobenzoic acid (300 mg, 2.14 mmol) in an excess of phosphoryl chloride, thiosemicarbazide (195 mg, 2.14 mmol) was added. After 2 hours reaction at 75° C., the mixture was cooled. And after adding water, the mixture was boiled for 4 hours and cooled. After recrystallization with 50% potassium hydroxide aqueous solution and filtering, 233 mg (1.20 mmol) was obtained in 56% yield.

Rf=0.32 (EA:HEX=3:1)

$^1$H NMR (300 MHz, DMSO-d$_6$) δ 13.09 (br s, 1H), 12.91 (br s, 1H), 8.23 (s, 1H), 7.95-7.99 (m, 2H), 7.85 (d, J=7.7 Hz, 2H), 7.28-7.38 (m, 4H), 7.19-7.24 (m, 1H), 4.35 (s, 2H)

<Example 23> Preparation of N-(5-(4-fluorophenyl)-1,3,4-thiadiazol-2-yl)-2-((4-oxo-1-phenyl-4,5-dihydro-1H-pyrazolo[3,4-d]pyrimidin-6-yl)thio) acetamide

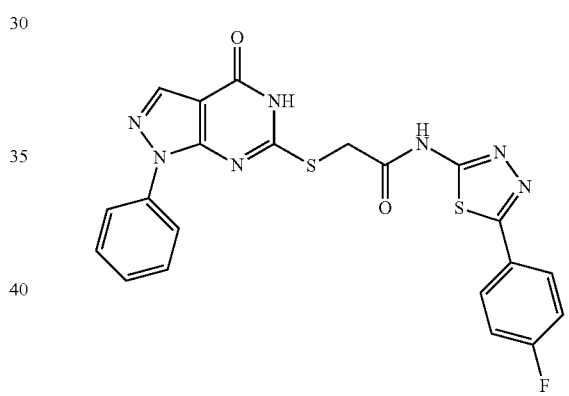

Step 1: Preparation of N-(5-(4-fluorophenyl)-1,3,4-thiadiazol-2-yl)-2-((4-oxo-1-phenyl-4,5-dihydro-1H-pyrazolo[3,4-d]pyrimidin-6-yl)thio)acetamide

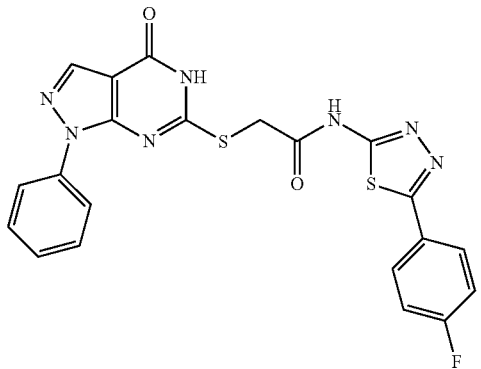 [SMILES: O=C(CSc1nc2c(cnn2-c2ccccc2)c(=O)[nH]1)Nc1nnc(-c2ccc(F)cc2)s1]

2-((4-oxo-1-phenyl-4,5-dihydro-1H-pyrazolo[3,4-d]pyrimidin-6-yl)thio)acetic acid (40 mg, 0.138 mmol) obtained in Preparation Example 3 was dissolved in dimethylformamide, and 5-(4-fluorophanyl)-1,3,4-thiadiazol-2-amine (107 mg, 0.55 mmol) obtained in Preparation Example 13, HATU (105 mg, 0.276 mmol), HOAT (37 mg, 0.276 mmol), and DIPEA (48 μl, 0.276 mmol) were added. A white solid was formed when cold water was added after reacting at room temperature for more than 12 hours. The solid was filtered and purified by column chromatography (EA:HEX=3:1->MeOH/MC=5%) to give 40 mg (0.084 mmol) in 61% yield.

Rf=0.32 (EA:HEX=3:1)

$^1$H NMR (300 MHz, DMSO-d$_6$) δ 13.09 (br s, 1H), 12.91 (br s, 1H), 8.23 (s, 1H), 7.95-7.99 (m, 2H), 7.85 (d, J=7.7 Hz, 2H), 7.28-7.38 (m, 4H), 7.19-7.24 (m, 1H), 4.35 (s, 2H)

<Example 24> Preparation of 2-((4-oxo-1-phenyl-4,5-dihydro-1H-pyrazolo[3,4-d]pyrimidin-6-yl)thio)-N-(5-(p-tolyl)-1,3,4-thiadiazol-2-yl)acetamide

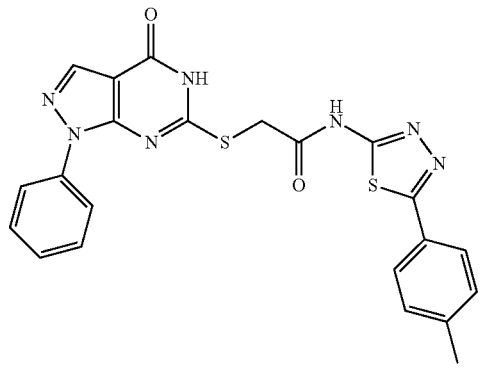 [SMILES: Cc1ccc(-c2nnc(NC(=O)CSc3nc4c(cnn4-c4ccccc4)c(=O)[nH]3)s2)cc1]

Step 1: Preparation of 2-((4-oxo-1-phenyl-4,5-dihydro-1H-pyrazolo[3,4-d]pyrimidin-6-yl)thio)-N-(5-(p-tolyl)-1,3,4-thiadiazol-2-yl)acetamide

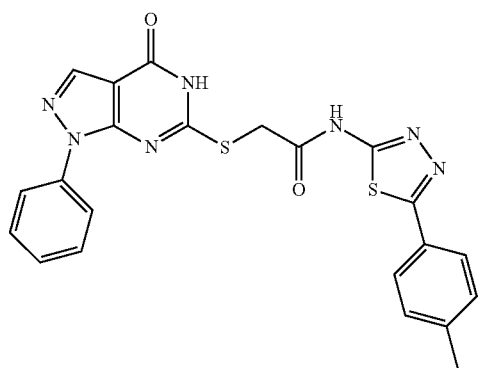 [SMILES: Cc1ccc(-c2nnc(NC(=O)CSc3nc4c(cnn4-c4ccccc4)c(=O)[nH]3)s2)cc1]

2-((4-oxo-1-phenyl-4,5-dihydro-1H-pyrazolo[3,4-d]pyrimidin-6-yl)thio)acetic acid (40 mg, 0.138 mmol) obtained in Preparation Example 3 was dissolved in dimethylformamide, and 5-(p-tolyl)-1,3,4-thiadiazol-2-amine (64 mg, 0.552 mmol) obtained in Preparation Example 12, HATU (105 mg, 0.276 mmol), HOAT (37 mg, 0.276 mmol), and DIPEA (48 μl, 0.276 mmol) were added. A white solid was formed when cold water was added after reacting at room temperature for more than 12 hours. Filtration of the solid gave 39 mg (0.081 mmol) in 59% yield.

Rf=0.35 (EA:HEX=3:1)

$^1$H NMR (300 MHz, DMSO-d$_6$) δ 13.05 (br s, 1H), 12.89 (br s, 1H), 8.23 (s, 1H), 7.85 (d, J=7.9 Hz, 2H), 7.80 (d, J=7.9 Hz, 2H), 7.28-7.33 (m, 4H), 7.19-7.24 (m, 1H), 4.35 (s, 2H), 2.35 (s, 3H)

Preparation Example 14> Preparation of 5-phenyl-1,3,4-thiadiazol-2-amine

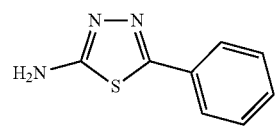 [SMILES: Nc1nnc(-c2ccccc2)s1]

Step 1: Preparation of 5-phenyl-1,3,4-thiadiazol-2-amine

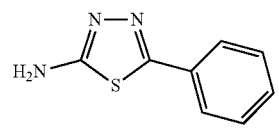

After dissolving benzoic acid (500 mg, 4.09 mmol) in an excess of phosphoryl chloride, thiosemicabazide (373 mg, 4.09 mmol) was added. After 2 hours reaction at 75° C., the mixture was cooled. And after adding water, the mixture was boiled for 4 hours and cooled. After recrystallization with 50% potassium hydroxide aqueous solution and filtration, 300 mg (1.68 mmol) was obtained in 41% yield.

Rf=0.45 (EA:HEX=1:10)

$^1$H NMR (300 MHz, DMSO-d$_6$) δ 7.73 (dd, J=1.9, 8.2 Hz, 2H), 7.40-7.46 (m, 5H)

<Example 25> Preparation of N-(5-phenyl-1,3,4-thiadiazol-2-yl)-2-((4-oxo-1-phenyl-4,5-dihydro-1H-pyrazolo[3,4-d]pyrimidin-6-yl)thio)acetamide

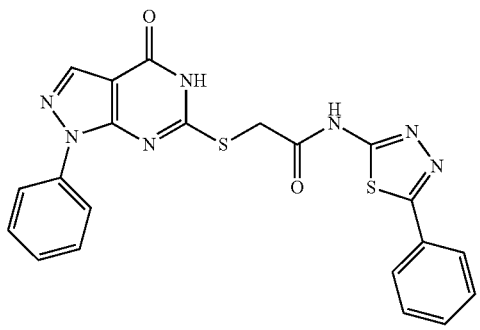 [SMILES: O=C(CSc1nc2c(cnn2-c2ccccc2)c(=O)[nH]1)Nc1nnc(-c2ccccc2)s1]

Step 1: Preparation of N-(5-phenyl-1,3,4-thiadiazol-2-yl)-2-((4-oxo-1-phenyl-4,5-dihydro-1H-pyrazolo[3,4-d]pyrimidin-6-yl)thio)acetamide

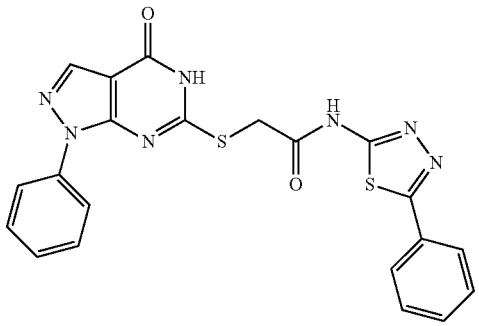 [SMILES: O=C(CSc1nc2c(cnn2-c2ccccc2)c(=O)[nH]1)Nc1nnc(-c2ccccc2)s1]

2-((4-oxo-1-phenyl-4,5-dihydro-1H-pyrazolo[3,4-d]pyrimidin-6-yl)thio)acetic acid (40 mg, 0.138 mmol) obtained in Preparation Example 3 was dissolved in dimethylformamide, and 5-phenyl-1,3,4-thiadiazol-2-amine (42 mg, 0.413 mmol) obtained in Preparation Example 14, HATU (105 mg, 0.276 mmol), HOAT (37 mg, 0.276 mmol), and DIPEA (48 µl, 0.276 mmol) were added. A white solid was formed when cold water was added after reacting at room temperature for more than 12 hours. Filtration of the solid gave 48 mg (0.102 mmol) in 74% yield.

Rf=0.22 (EA:HEX=3:1)

$^1$H NMR (300 MHz, DMSO-$d_6$) δ 12.99 (br s, 1H), 8.22 (s, 1H), 7.84-7.91 (m, 4H), 7.50-7.52 (m, 3H), 7.28-7.31 (m, 2H), 7.19-7.22 (m, 1H), 4.34 (s, 2H)

Preparation Example 15> Preparation of 2-((4-oxo-1-phenyl-4,5-dihydro-1H-pyrazolo[3,4-d]pyrimidin-6-yl)thio)-2-phenylacetic acid

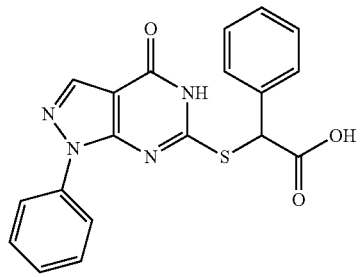 [SMILES: O=C(O)C(Sc1nc2c(cnn2-c2ccccc2)c(=O)[nH]1)c1ccccc1]

Step 1: Preparation of ethyl 2-((4-oxo-1-phenyl-4,5-dihydro-1H-pyrazolo[3,4-d]pyrimidin-6-yl)thio)-2-phenylacetate

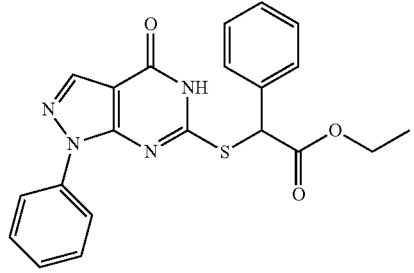 [SMILES: CCOC(=O)C(Sc1nc2c(cnn2-c2ccccc2)c(=O)[nH]1)c1ccccc1]

184 mg of 6-chloro-1-phenyl-1,5-dihydro-4H-pyrazolo[3,4-d]pyridin-4-one (0.744 mmol) obtained in Preparation Example 3 Step 2, 302 mg of potassium carbonate (2.232 mmol) and 219 mg of ethyl 2-mercapto-2-phenylacetate (1.116 mmol) were dissolved in 5 ml of DMF and stirred at 90° C. for 16 hours. After completion of the reaction, the resultant was extracted with ethyl acetate and tetrahydrofuran, and washed with water, 1N hydrochloric acid, and saturated brine. The filtrate concentrated under reduced pressure was purified by column chromatography (normal hexane:ethyl acetate=2:1->1:1->methanol/dichloromethane=5%, v/v) to give 80 mg of the solid title compound (0.197 mmol) in 26% yield.

Rf=0.54 (normal hexane:ethyl acetate=1:1, v/v)

$^1$H NMR (500 MHz, CDCl$_3$) δ 10.22 (brs, 1H), 8.20 (s, 1H), 8.00 (d, J=7.8 Hz, 2H), 7.52-7.57 (m, 2H), 7.45-7.50 (m, 2H), 7.36-7.43 (m, 4H), 5.65 (s, 1H), 4.14-4.21 (m, 1H), 3.99-4.07 (m, 1H), 1.11 (t, J=7.1 Hz, 3H)

Step 2: Preparation of 2-((4-oxo-1-phenyl-4,5-dihydro-1H-pyrazolo[3,4-d]pyrimidin-6-yl)thio)-2-phenylacetic acid

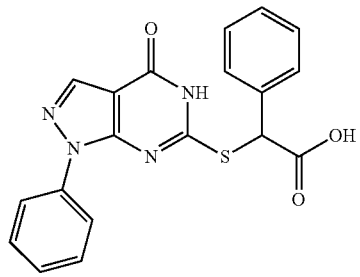 [SMILES: O=C(O)C(Sc1nc2c(cnn2-c2ccccc2)c(=O)[nH]1)c1ccccc1]

73 mg of ethyl 2-((4-oxo-1-phenyl-4,5-dihydro-1H-pyrazolo[3,4-d]pyrimidin-6-yl)thio)-2-phenylacetate (0.180 mmol) obtained in Step 1 was dissolved in 3 ml of tetrahydrofuran, and 2N sodium hydroxide was added, followed by stirring at room temperature for 16 hours. After completion of the reaction, it was neutralized with 1N hydrochloric acid, extracted with ethyl acetate and tetrahydrofuran, and washed with water and saturated brine. The resultant was concentrated under reduced pressure to give 71 mg of the solid title compound (0.180 mmol) in 99% yield.

$^1$H NMR (300 MHz, MeOD-$d_4$) δ 8.16 (s, 1H), 8.03 (d, J=7.7 Hz, 2H), 7.48-7.59 (m, 4H), 7.35-7.44 (m, 4H), 5.63 (s, 1H)

<Example 26> N-(5-(ethylthio)-1,3,4-thiadiazol-2-yl)-2-((4-oxo-1-phenyl-4,5-dihydro-1H-pyrazolo[3,4-d]pyrimidin-6-yl)thio)-2-phenylacetamide

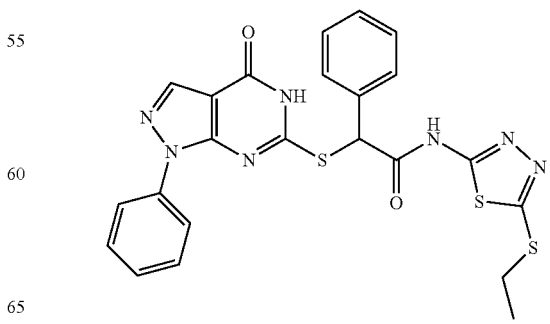

Step 1: Preparation of N-(5-(ethylthio)-1,3,4-thiadiazol-2-yl)-2-((4-oxo-1-phenyl-4,5-dihydro-1H-pyrazolo[3,4-d]pyrimidin-6-yl)thio)-2-phenylacetamide

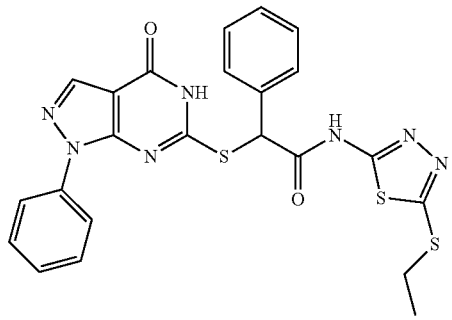 [SMILES: CCSc1nnc(NC(=O)C(Sc2nc3c(cnn3-c3ccccc3)c(=O)[nH]2)c2ccccc2)s1]

28 mg of 2-((4-oxo-1-phenyl-4,5-dihydro-1H-pyrazolo[3,4-d]pyrimidin-6-yl)thio)-2-phenylacetic acid (0.074 mmol) obtained in Preparation Example 15, 36 mg of 5-(ethylthio)-1,3,4-thiadiazole-2-amine (0.368 mmol) obtained in Preparation Example 4, and 38 mg of BOP-Cl (0.148 mmol) were dissolved in 2 ml of DMF, and then 26 μl of DIPEA (0.148 mmol) was added, followed by stirring at room temperature for 64 hours. After completion of the reaction, the resultant was extracted with ethyl acetate and washed with water and saturated brine. The filtrate concentrated under reduced pressure was purified by column chromatography (hexane:ethyl acetate=3:1->1:1, v/v) to give 5 mg of the solid title compound (0.0096 mmol) in 13% yield.

Rf=0.45 (Hex:EA=1:1, v/v)
$^1$H NMR (300 MHz, MeOD-$d_4$) δ 8.15 (s, 1H), 7.71 (d, J=1N Hz, 2H), 7.47-7.53 (m, 2H), 7.30-7.43 (m, 5H), 7.19-7.26 (m, 1H), 5.79 (s, 1H), 3.20 (q, J=7.5 Hz, 2H), 1.39 (t, J=7.5 Hz, 3H)

Preparation Example 16> Preparation of (tetrahydro-2H-pyran-4-yl)hydrazine hydrogen chloride

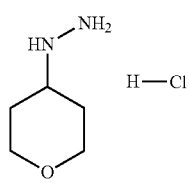

Step 1: Preparation of tert-butyl 2-(tetrahydro-4H-4-ylidene)hydrazine-1-carboxylate

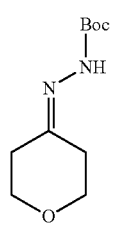

3 g of tetrahydro-4H-pyran4-one (29.96 mmol) was dissolved in 60 ml of hexane, and 3.96 g of tert-butyl carbazate (29.96 mmol) was added, followed by stirring under reflux for 3 hours. After completion of the reaction, the resultant was concentrated under reduced pressure to give 6.4 g of the title compound (29.96 mmol) in 100% yield.

Rf=0.19 (hexane:ethyl acetate=1:1, v/v)
$^1$H NMR (300 MHz, DMSO-$d_6$) δ 9.65 (br s, 1H), 3.69 (t, J=5.7 Hz, 2H), 3.60 (t, J=5.7 Hz, 2H), 2.41 (t, J=5.7 Hz, 2H), 2.27 (t, J=5.7 Hz, 2H), 1.43 (s, 9H)

Step 2: Preparation of tert-butyl 2-(tetrahydro-2H-pyran-4-yl)hydrazine-1-carboxylate

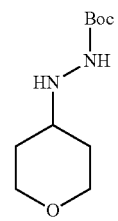 [SMILES: CC(C)(C)OC(=O)NNC1CCOCC1]

6.4 g of tert-butyl 2-(tetrahydro-4H-4-ylidene)hydrazine-1-carboxylate (29.96 mmol) obtained in Step 1 was dissolved in 50 ml of THF, and 12.7 g of sodium triacetoxy borohydride (59.92 mmol) was added and stirred at room temperature for 15 hours. After completion of the reaction, the resultant was extracted with 500 ml of ethyl acetate, washed with 500 ml of an inorganic salt solution, dried over anhydrous sodium sulfate (Na$_2$SO$_4$), and concentrated under reduced pressure. The residue was purified by column chromatography (hexane:ethyl acetate=1:2, v/v) to give 6 g of the title compound (27.74 mmol) in 92% yield.

Rf=0.38 (hexane:ethyl acetate=1:2, v/v)
$^1$H NMR (300 MHz, CDCl$_3$) δ 6.24 (br s, 1H), 3.95-3.99 (m, 2H), 3.38-3.43 (m, 2H), 3.05-3.11 (m, 1H), 1.75-1.81 (m, 2H), 1.40-1.52 (m, 11H)

Step 3: Preparation of (tetrahydro-2H-pyran-4-yl)hydrazine hydrogen chloride

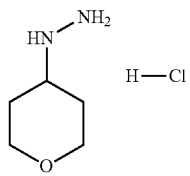

6 g of tert-butyl 2-(tetrahydro-2H-pyran-4-yl)hydrazine-1-carboxylate (27.74 mmol) obtained in Step 2 above was dissolved in 50 ml of methanol, and hydrochloric acid was added and stirred at 50° C. for 3 hours. After completion of the reaction, the resultant was concentrated under reduced pressure to give 4 g of the title compound (26.21 mmol) in 94% yield.

Rf=0.00 (hexane:ethyl acetate=3:1, v/v)
$^1$H NMR (300 MHz, DMSO-$d_6$) δ 7.25 (br s, 1H), 3.83-3.92 (m, 2H), 3.23-3.31 (m, 2H), 3.08-3.18 (m, 1H), 1.84-1.95 (m, 2H), 1.41-1.54 (m, 2H)

<Preparation Example 17> Preparation of 2-((4-oxo-1-(tetrahydro-2H-pyran-4-yl)-4,5-dihydro-1H-pyrazolo[3,4-d]pyrimidine-6-yl)thio)acetic acid

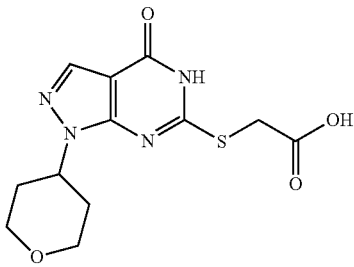 [SMILES: O=C(O)CSc1nc2c(cnn2C2CCOCC2)c(=O)[nH]1]

Step 1: Preparation of 4,6-dichloro-1-(tetrahydro-2H-pyran-4-yl)-1H-pyrazolo[3,4-d]pyrimidine

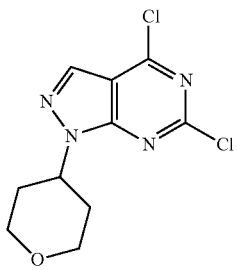 [SMILES: Clc1nc(Cl)c2cnn(C3CCOCC3)c2n1]

5.55 g of 2,4,6-trichloropyrimidine-5-carbaldehyde (26.21 mmol) obtained in Preparation Example 16 was dissolved in 50 ml of ethanol, and 4 g of (tetrahydro-2H-pyran-4-yl)hydrazine hydrogen chloride (26.21 mmol) obtained in Step 3 above and 14 ml of N,N-diisopropylethylamine (78.63 mmol) were added −78° C. and stirred for 3 hours. After completion of the reaction, the resultant was extracted with 100 ml of ethyl acetate, washed with 100 ml of an inorganic salt solution, dried over anhydrous sodium sulfate ($Na_2SO_4$), and concentrated under reduced pressure. The residue was purified by column chromatography (hexane:ethyl acetate=5:1, v/v) to give 6.5 g of the title compound (23.80 mmol) in 91% yield.

Rf=0.20 (hexane:ethyl acetate=9:1, v/v)

$^1$H NMR (300 MHz, DMSO-$d_6$) δ 8.57 (s, 1H), 4.96-5.03 (m, 1H), 3.98-4.02 (m, 2H), 3.56-3.61 (m, 2H), 2.10-2.19 (m, 2H), 1.90-1.95 (m, 2H)

Step 2: Preparation of 6-chloro-1-(tetrahydro-2H-pyran-4-yl)-1,5-dihydro-4H-pyrazolo[3,4-d]pyrimidin-4-one

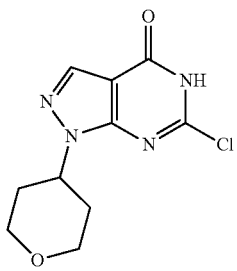 [SMILES: O=c1[nH]c(Cl)nc2c1cnn2C1CCOCC1]

6.5 g of 4,6-dichloro-1-(tetrahydro-2H-pyran-4-yl)-1H-pyrazolo[3,4-d]pyrimidine (23.80 mmol) prepared in Step 1 above was dissolved in 50 ml of THF, and 25 ml of 2N sodium hydroxide (23.80 mmol) was added, followed by stirring under reflux for 15 hours. After completion of the reaction, the mixture was acidified with 6N hydrochloric acid, and the precipitated solid compound was filtered to give 5.4 g of the title compound (21.20 mmol) in 89% yield.

Rf=0.20 (dichloromethane:methanol=20:1, v/v)

$^1$H NMR (500 MHz, DMSO-$d_6$) δ 13.21 (br s, 1H), 8.11 (s, 1H), 4.75-4.81 (m, 1H), 3.95-3.99 (m, 2H), 3.51-3.56 (m, 2H), 2.05-2.12 (m, 2H), 1.81-1.86 (m, 2H)

Step 3: Preparation of ethyl 2-((4-oxo-1-(tetrahydro-2H-pyran-4-yl)-4,5-dihydro-1H-pyrazolo[3,4-d]pyrimidine-6-yl)thio)acetate

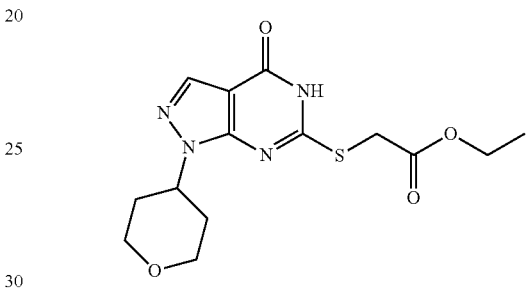

300 mg of 6-chloro-1-(tetrahydro-2H-pyran-4-yl)-1,5-dihydro-4H-pyrazolo[3,4-d]pyridin-4-one (1.178 mmol) obtained in Step 2 above, 478 mg of potassium carbonate (3.117 mmol) and 270 μl of ethyl thioglycolate (2.474 mmol) were dissolved in 5 ml of DMF, followed by stirring at 90° C. for 16 hours. After completion of the reaction, the resultant was extracted with ethyl acetate and tetrahydrofuran, and washed with water, 1N hydrochloric acid, and saturated brine. The filtrate concentrated under reduced pressure was purified by column chromatography (methanol/dichloromethane 3%, v/v) to give 374 mg of the solid title compound (1.105 mmol) in 94% yield.

Rf=0.27 (normal hexane:ethyl acetate=1:1, v/v)

$^1$H NMR (300 MHz, CDCl$_3$) δ 10.71 (brs, 1H), 8.04 (s, 1H), 4.68-4.81 (m, 1H), 4.25 (q, J=7.1 Hz, 2H), 4.11-4.20 (m, 2H), 4.00 (s, 2H), 3.54-3.65 (m, 2H), 2.29-2.45 (m, 2H), 1.87-1.96 (m, 2H), 1.31 (t, J=7.1 Hz, 3H)

Step 4: Preparation of 2-((4-oxo-1-(tetrahydro-2H-pyran-4-yl)-4,5-dihydro-1H-pyrazolo[3,4-d]pyrimidin-6-yl)thio)acetic acid

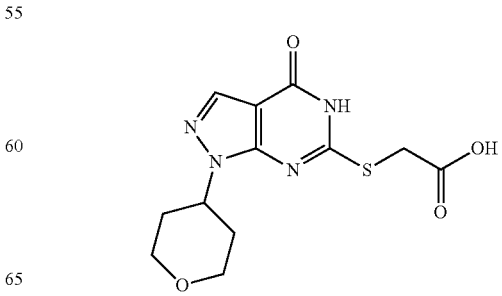

360 mg of ethyl 2-((4-oxo-1-(tetrahydro-2H-pyran-4-yl)-4,5-dihydro-1H-pyrazolo[3,4-d]pyrimidin-6-yl)thio)acetate (1.064 mmol) prepared in Step 3 above was dissolved in 5 ml of tetrahydrofuran, and 2N sodium hydroxide was added, and stirred at room temperature for 16 hours. After completion of the reaction, it was neutralized with 1N hydrochloric acid, extracted with ethyl acetate and tetrahydrofuran, and washed with water and saturated brine. After concentration under reduced pressure, 277 mg of the solid title compound (0.893 mmol) was obtained in 84% yield.

$^1$H NMR (300 MHz, DMSO-$d_6$) δ 12.86 (brs, 1H), 12.54 (brs, 1H), 7.98 (s, 1H), 4.65-4.78 (m, 1H), 3.94-4.03 (m, 4H), 3.41-3.52 (m, 2H), 1.99-2.15 (m, 2H), 1.79-1.88 (m, 2H)

<Example 27> Preparation of N-(5-(ethylthio)-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio)acetamide

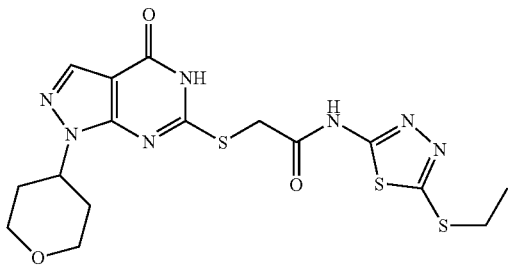 [SMILES: CCSc1nnc(NC(=O)CSc2nc3c(cnn3C3CCOCC3)c(=O)[nH]2)s1]

Step 1: Preparation of N-(5-(ethylthio)-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio)acetamide

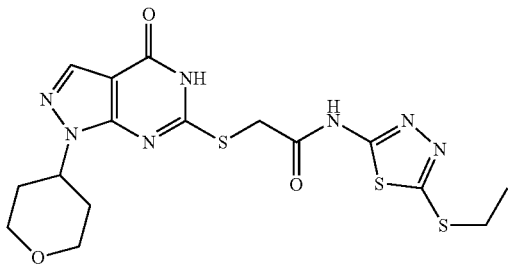 [SMILES: CCSc1nnc(NC(=O)CSc2nc3c(cnn3C3CCOCC3)c(=O)[nH]2)s1]

40 mg of 2-((4-oxo-1-(tetrahydro-2H-pyran-4-yl)-4,5-dihydro-1H-pyrazolo[3,4-d]pyrimidin-6-yl)thio)acetic acid (0.129 mmol) obtained in Preparation Example 17, 62 mg of 5-(ethylthio)-1,3,4-thiadiazol-2-amine (0.387 mmol) obtained in Preparation Example 4, and 66 mg of CMPI (0.258 mmol) were dissolved in 2 ml of DMF, and 45 μl of DIPEA (0.258 mmol) was added, followed by stirring at room temperature for 72 hours. After completion of the reaction, the resultant was extracted with ethyl acetate and washed with water and saturated brine. The filtrate concentrated under reduced pressure was purified by column chromatography (hexane:ethyl acetate=1:1->methanol/dichloromethane 3%, v/v) to give 19.5 mg of the solid title compound (0.043 mmol) in 33% yield.

Rf=0.23 (hexane:ethyl acetate=1:1, v/v)

$^1$H NMR (500 MHz, DMSO-$d_6$) δ 7.96 (s, 1H), 4.48-4.56 (m, 1H), 4.23 (s, 2H), 3.74-3.80 (m, 2H), 3.15-3.24 (m, 4H), 1.89-1.99 (m, 2H), 1.50-1.57 (m, 2H), 1.31 (t, J=7.3 Hz, 3H)

Preparation Example 18> Preparation of 2-((1-(4,4-difluorocyclohexyl)-4-oxo-4,5-dihydro-1H-pyrazolo[3,4-d]pyrimidin-6-yl)thio)propanoic acid

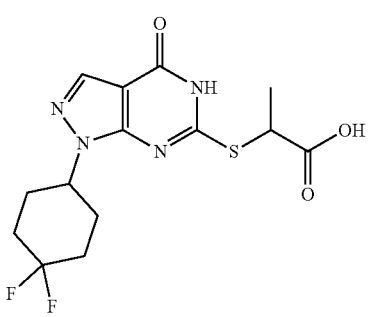 [SMILES: CC(Sc1nc2c(cnn2C2CCC(F)(F)CC2)c(=O)[nH]1)C(=O)O]

Step 1: Preparation of ethyl 2-((1-(4,4-difluorocyclohexanyl)-4-oxo-4,5-dihydro-1H-pyrazolo[3,4-d]pyrimidin-6-yl)thio)propanoate

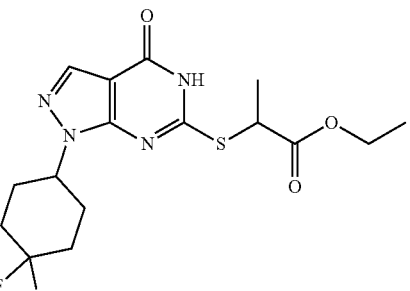

300 mg of 6-chloro-1-(4,4-difluorocyclohexyl)-1,5-dihydro-4H-pyrazolo[3,4-d]pyridin-4-one (1.039 mmol) obtained in Preparation Example 2 Step 2, 431 mg of potassium carbonate (3.117 mmol), and 282 μl of ethyl 2-mercaptopropionate (2.182 mmol) were dissolved in 5 ml of DMF and stirred at 90° C. for 3 hours. After completion of the reaction, the resultant was extracted with ethyl acetate and tetrahydrofuran, and washed with water, 1N hydrochloric acid, and saturated brine. The filtrate concentrated under reduced pressure was purified by column chromatography (hexane:ethyl acetate=2:1, v/v) to give 201 mg of the solid title compound (0.520 mmol) in 50% yield.

Rf=0.65 (normal hexane:ethyl acetate=1:1, v/v)

$^1$H NMR (300 MHz, CDCl$_3$) δ 10.74 (brs, 1H), 8.03 (s, 1H), 4.61-4.74 (m, 1H), 4.49 (q, J=7.2 Hz, 1H), 4.09-4.31 (m, 2H), 2.24-2.48 (m, 4H), 1.88-2.13 (m, 4H), 1.70 (d, J=7.2 Hz, 3H), 1.28 (t, J=7.1 Hz, 3H)

Step 2: Preparation of 2-((1-(4,4-difluorocyclo-hexyl)-4-oxo-4,5-dihydro-1H-pyrazolo[3,4-d]pyrimidin-6-yl)thio)propanoic acid

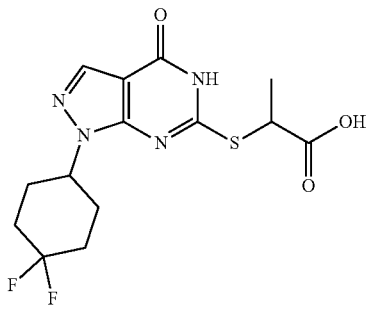 [SMILES: CC(Sc1nc2c(cnn2C2CCC(F)(F)CC2)c(=O)[nH]1)C(=O)O]

200 mg of ethyl 2-((1-(4,4-difluorocyclohexyl)-4-oxo-4,5-dihydro-1H-pyrazolo[3,4-d]pyrimidin-6-yl)thio)propanoate (0.518 mmol) obtained in Step 1 was dissolved in 3 ml of tetrahydrofuran, and 2N sodium hydroxide was added, and stirred at room temperature for 1 hour minutes. After completion of the reaction, it was neutralized with 1N hydrochloric acid, extracted with ethyl acetate and tetrahydrofuran, and washed with water and saturated brine. The resultant was concentrated under reduced pressure to give 166 mg of the solid title compound (0.463 mmol) in 89% yield.

$^1$H NMR (300 MHz, DMSO-d$_6$) δ 7.97 (s, 1H), 4.65-4.77 (m, 1H), 4.42 (q, J=7.2 Hz, 1H), 1.93-2.23 (m, 8H), 1.56 (d, J=7.2 Hz, 3H)

<Example 28> Preparation of 2-((1-(4,4-difluorocyclohexyl)-4-oxo-4,5-dihydro-1H-pyrazolo[3,4-d]pyrimidin-6-yl)thio)-N-(5-(ethylthio)-1,3,4-thiadiazol-2-yl)propanamide

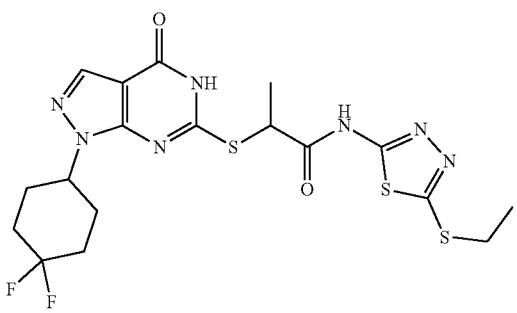 [SMILES: CCSc1nnc(NC(=O)C(C)Sc2nc3c(cnn3C3CCC(F)(F)CC3)c(=O)[nH]2)s1]

Step 1: Preparation of 2-((1-(4,4-difluorocyclohexyl)-4-oxo-4,5-dihydro-1H-pyrazolo[3,4-d]pyrimidin-6-yl)thio)-N-(5-(ethylthio)-1,3,4-thiadiazol-2-yl)propanamide

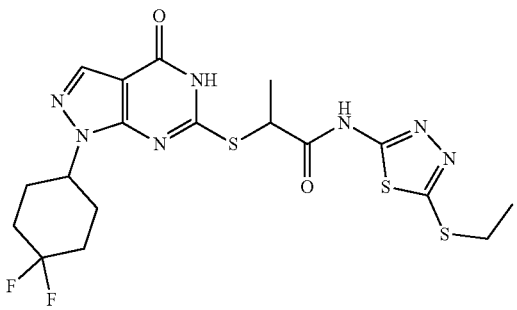 [SMILES: CCSc1nnc(NC(=O)C(C)Sc2nc3c(cnn3C3CCC(F)(F)CC3)c(=O)[nH]2)s1]

40 mg of 2-((1-(4,4-difluorocyclohexyl)-4-oxo-4,5-dihydro-1H-pyrazolo[3,4-d]pyrimidin-6-yl)thio)acetic acid (0.112 mmol) obtained in Preparation Example 18, 54 mg of 5-(ethylthio)-1,3,4-thiadiazole-2-amine (0.336 mmol) obtained in Preparation Example 4, and 39 mg of CDMT (0.223 mmol) was dissolved in 2 ml of DMF, 25 μl of NMM (0.223 mmol) was added, followed by stirring at room temperature for 48 hours. After completion of the reaction, the resultant was extracted with ethyl acetate and washed with water and saturated brine. The filtrate concentrated under reduced pressure was purified by column chromatography (hexane:ethyl acetate=1.5:1->1:1.5, v/v) to give 28.7 mg of the solid title compound (0.057 mmol) in 51% yield.

Rf=0.24 (hexane:ethyl acetate=1:1, v/v)

$^1$H NMR (300 MHz, CDCl$_3$) δ 12.05-12.70 (m, 2H), 8.02 (s, 1H), 4.61-4.80 (m, 2H), 3.24 (q, J=7.2 Hz, 2H), 2.13-2.41 (m, 4H), 1.91-2.02 (m, 4H), 1.78 (d, J=7.5 Hz, 3H), 1.42 (t, J=7.2 Hz, 3H)

Preparation Example 19> Preparation of (tetrahydro-2H-thiopyran-4-yl)hydrazine hydrogen chloride

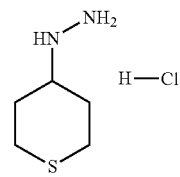

Step 1: Preparation of tert-butyl 2-(tetrahydro-4H-thiopyran-4-ylidene)hydrazine-1-carboxylate

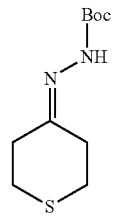

3.3 g of tetrahydro-4H-thiopyran-4-one (28.40 mmol) was dissolved in 60 ml of hexane, and 4.13 g of tert-butyl carbazate (31.24 mmol) was added, followed by stirring under reflux for 3 hours. After completion of the reaction, the resultant was concentrated under reduced pressure to give 6.5 g of the title compound (28.40 mmol) in 100% yield.

Rf=0.15 (hexane:ethyl acetate=3:1, v/v)

$^1$H NMR (500 MHz, DMSO-d$_6$) δ 9.67 (br s, 1H), 2.73-2.76 (m, 2H), 2.65-2.68 (m, 2H), 2.60-2.63 (m, 2H), 2.47-2.50 (m, 2H), 1.43 (s, 9H)

Step 2: Preparation of tert-butyl 2-(tetrahydro-2H-thiopyran-4-yl)hydrazine-1-carboxylate

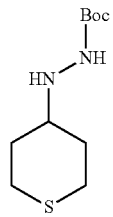

6.4 g of tert-butyl 2-(tetrahydro-4H-thiopyran-4-ylidene)hydrazine-1-carboxylate (28.40 mmol) obtained in Step 1 above was dissolved in 80 ml of THF and 12 g of sodium triacetoxy borohydride (56.80 mmol) was added and stirred at room temperature for 15 hours. After completion of the reaction, the resultant was extracted with 300 ml of ethyl acetate, washed with 300 ml of an inorganic salt solution, dried over anhydrous sodium sulfate ($Na_2SO_4$), and concentrated under reduced pressure. The residue was purified by column chromatography (hexane:ethyl acetate=2:1, v/v) to give 6.5 g of the title compound (27.97 mmol) in 98% yield.

Rf=0.34 (hexane:ethyl acetate=2:1, v/v)

$^1$H NMR (500 MHz, DMSO-$d_6$) δ 8.20 (br s, 1H), 4.28 (br s, 1H), 2.65-2.73 (m, 3H), 2.05-2.49 (m, 2H), 1.93-1.98 (m, 2H), 1.34-1.43 (m, 1H)

Step 3: Preparation of (tetrahydro-2H-pyran-4-yl)hydrazine hydrogen chloride

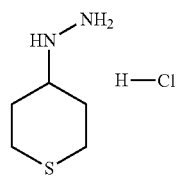

6.5 g of tert-butyl 2-(tetrahydro-2H-thiopyran-4-yl)hydrazine-1-carboxylate (27.97 mmol) obtained in Step 2 was dissolved in 60 ml of methanol, and hydrochloric acid was added thereto and stirred 50° C. for 3 hours. After completion of the reaction, the reaction solution was concentrated under reduced pressure to give 4.7 g of the title compound (27.97 mmol) in 94% yield.

$^1$H NMR (500 MHz, DMSO-$d_6$) δ 2.91-2.96 (m, 1H), 2.66-2.72 (m, 2H), 2.57-2.62 (m, 2H), 2.25-2.29 (m, 2H), 1.53-1.60 (m, 2H)

Preparation Example 20> Preparation of 2-((4-oxo-1-(tetrahydro-2H-thiopyran-4-yl)-4,5-dihydro-1H-pyrazolo[3,4-d]pyrimidin-6-yl)thio)acetic acid

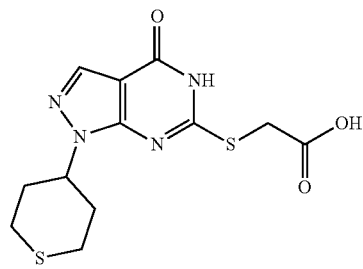 [SMILES: O=C(O)CSc1nc2c(cnn2C2CCSCC2)c(=O)[nH]1]

Step 1: Preparation of 4,6-dichloro-1-(tetrahydro-2H-thiopyran-4-yl)-1H-pyrazolo[3,4-d]pyrimidine

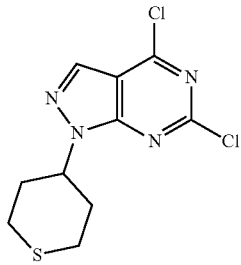 [SMILES: Clc1nc(Cl)c2cnn(C3CCSCC3)c2n1]

5.9 g of 2,4,6-trichloropyrimidine-5-carbaldehyde (27.97 mmol) obtained in Preparation Example 19 was dissolved in 60 ml of ethanol, and 4.7 g of (tetrahydro-2H-thiopyran-4-yl)hydrazine hydrogen chloride (27.97 mmol) obtained in Step 3 above and 15 ml of N,N-diisopropylethylamine (83.91 mmol) were added at −78° C. and stirred for 3 hours. After completion of the reaction, the resultant was extracted with 200 ml of ethyl acetate, washed with 200 ml of an inorganic salt solution, dried over anhydrous sodium sulfate ($Na_2SO_4$), and the reaction solution was concentrated under reduced pressure. The residue was purified by column chromatography (hexane:ethyl acetate=5:1, v/v) to give 7 g of the title compound (24.20 mmol) in 86% yield.

Rf=0.41 (hexane:ethyl acetate=10:1, v/v)

$^1$H NMR (500 MHz, DMSO-$d_6$) δ 8.57 (s, 1H), 4.78-4.85 (m, 1H), 2.93-2.98 (m, 2H), 2.73-2.78 (m, 2H), 2.15-2.25 (m, 4H)

Step 2: Preparation of 6-chloro-1-(tetrahydro-2H-thiopyran-4-yl)-1,5-dihydro-4H-pyrazolo[3,4-d]pyrimidin-4-one

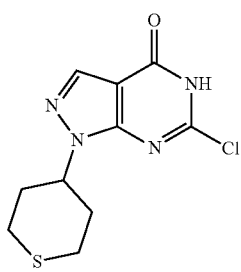 [SMILES: O=c1[nH]c(Cl)nc2c1cnn2C1CCSCC1]

7 g of 4,6-dichloro-1-(tetrahydro-2H-thiopyran-4-yl)-1H-pyrazolo[3,4-d]pyrimidine (24.20 mmol) prepared in Step 1 above was dissolved in 50 ml of THF, and 25 ml of 2N sodium hydroxide (47.60 mmol) was added, and stirred under reflux for 15 hours. After completion of the reaction, the mixture was acidified with 6N hydrochloric acid, and the precipitated solid compound was filtered to give 5.7 g of the title compound (21.05 mmol) in 87% yield.

Rf=0.31 (dichloromethane:methanol=20:1, v/v)

$^1$H NMR (500 MHz, DMSO-$d_6$) δ 13.20 (br s, 1H), 8.11 (s, 1H), 4.56-4.63 (m, 1H), 2.88-2.94 (m, 2H), 2.72-2.76 (m, 2H), 2.10-2.20 (m, 4H)

Step 3: Preparation of ethyl 2-((4-oxo-1-(tetrahydro-2H-thiopyran-4-yl)-4,5-dihydro-1H-pyrazolo[3,4-d]pyrimidin-6-yl)thio)acetate

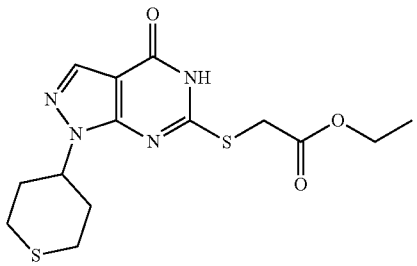 [SMILES: CCOC(=O)CSc1nc2c(cnn2C2CCSCC2)c(=O)[nH]1]

200 mg of 6-chloro-1-(tetrahydro-2H-thiopyran-4-yl)-1,5-dihydro-4H-pyrazolo[3,4-d]pyridin-4-one (0.739 mmol) obtained in Step 2 above, 300 mg of potassium carbonate (2.216 mmol), and 170 µl of ethyl thioglycolate (1.552 mmol) were dissolved in 4 ml of DMF, followed by stirring at 90° C. for 3 hours. After completion of the reaction, the resultant was extracted with ethyl acetate and tetrahydrofuran, followed by washing with water, 1N hydrochloric acid, and saturated brine. The filtrate concentrated under reduced pressure was purified by column chromatography (hexane:ethyl acetate=1:1, v/v) to give 196 mg of the solid title compound (0.553 mmol) in 75% yield.

Rf=0.47 (normal hexane:ethyl acetate=1:1, v/v)

$^1$H NMR (500 MHz, CDCl$_3$) δ 10.08 (brs, 1H), 8.02 (s, 1H), 4.48-4.56 (m, 1H), 4.26 (q, J=7.1 Hz, 2H), 4.00 (s, 2H), 2.79-2.93 (m, 4H), 2.36-2.46 (m, 2H), 2.21-2.28 (m, 2H), 1.32 (t, J=7.1 Hz, 3H)

Step 4: Preparation of 2-((4-oxo-1-(tetrahydro-2H-thiopyran-4-yl)-4,5-dihydro-1H-pyrazolo[3,4-d]pyrimidin-6-yl)thio)acetic acid

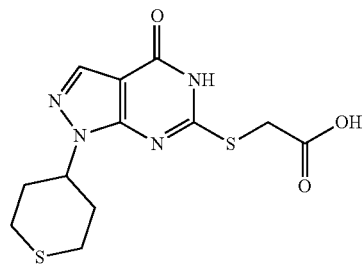 [SMILES: O=C(O)CSc1nc2c(cnn2C2CCSCC2)c(=O)[nH]1]

185 mg of ethyl 2-((4-oxo-1-(tetrahydro-2H-thiopyran-4-yl)-4,5-dihydro-1H-pyrazolo[3,4-d]pyrimidin-6-yl)thio)acetate (0.522 mmol) prepared in Step 3 above was dissolved in 5 ml of tetrahydrofuran, and 2N sodium hydroxide was added, followed by stirring at room temperature for 16 hours. After completion of the reaction, it was neutralized with 1N hydrochloric acid, extracted with ethyl acetate and tetrahydrofuran, and washed with water and saturated brine. The resultant was concentrated under reduced pressure to give 173 mg of the solid title compound (0.530 mmol) in 99% yield.

$^1$H NMR (300 MHz, DMSO-d$_6$) δ 7.97 (s, 1H), 4.45-4.58 (m, 1H), 3.98 (s, 2H), 2.69-2.88 (m, 4H), 2.07-2.21 (m, 4H)

<Example 29> Preparation of N-(5-(ethylthio)-1,3,4-thiadiazol-2-yl)-2-((4-oxo-1-(tetrahydro-2H-thiopyran-4-yl)-4,5-dihydro-1H-pyrazolo[3,4-d]pyrimidin-6-yl)thio)acetamide

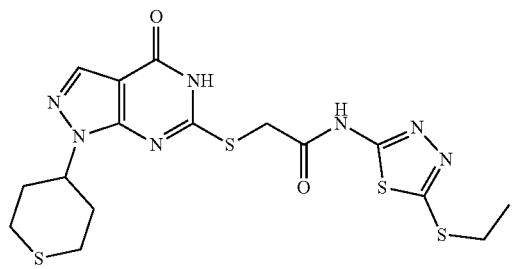 [SMILES: CCSc1nnc(NC(=O)CSc2nc3c(cnn3C3CCSCC3)c(=O)[nH]2)s1]

Step 1: Preparation of N-(5-(ethylthio)-1,3,4-thiadiazol-2-yl)-2-((4-oxo-1-(tetrahydro-2H-thiopyran-4-yl)-4,5-dihydro-1H-pyrazolo[3,4-d]pyrimidin-6-yl)thio)acetamide

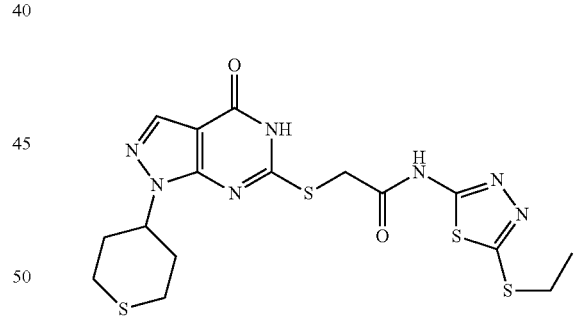

40 mg of 2-((4-oxo-1-(tetrahydro-2H-thiopyran-4-yl)-4,5-dihydro-1H-pyrazolo[3,4-d]pyridmidin-6-yl)thio)acetic acid (0.123 mmol) obtained in Preparation Example 20, 63 mg of 5-(ethylthio)-1,3,4-thiadiazol-2-amine (0.369 mmol), and 63 mg of CMPI (0.245 mmol) were dissolved in 2 ml of DMF and 43 µl of DIPEA (0.245 mmol) was added, followed by stirring at room temperature for 72 hours. After completion of the reaction, water was added to precipitate, washed with water and ethyl ether, and filtered to give 31.1 mg of the solid title compound (0.066 mmol) in 54% yield.

$^1$H NMR (300 MHz, DMSO-d$_6$) δ 13.07 (brs, 1H), 12.59 (brs, 1H), 7.95 (s, 1H), 4.28-4.40 (m, 1H), 4.24 (s, 2H), 3.21 (q, J=7.3 Hz, 2H), 2.51-2.58 (m, 4H), 1.82-2.07 (m, 4H), 1.32 (t, J=7.3 Hz, 3H)

\<Example 30\> Preparation of N-(5-chloro-1,3,4-thiadiazol-2-yl)-2-((4-oxo-1-phenyl-4,5-dihydro-1H-pyrazolo[3,4-d]pyrimidin-6-yl)thio)acetamide

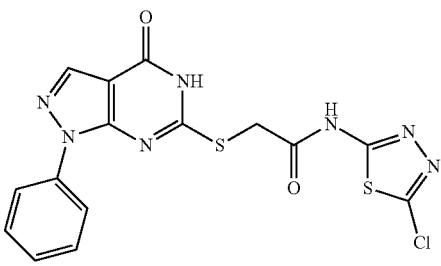 [SMILES: O=C(CSc1nc2c(cnn2-c2ccccc2)c(=O)[nH]1)Nc1nnc(Cl)s1]

Step 1: Preparation of N-(5-chloro-1,3,4-thiadiazol-2-yl)-2-((4-oxo-1-phenyl-4,5-dihydro-1H-pyrazolo[3,4-d]pyrimidin-6-yl)thio)acetamide

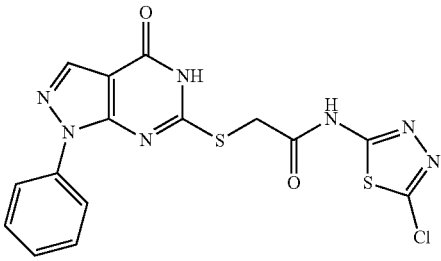 [SMILES: O=C(CSc1nc2c(cnn2-c2ccccc2)c(=O)[nH]1)Nc1nnc(Cl)s1]

40 mg of 2-((4-oxo-1-phenyl-4,5-dihydro-1H-pyrazolo[3,4-d]pyrimidin-6-yl)thio)acetic acid (0.132 mmol) obtained in Preparation Example 3, 54 mg of 5-chloro-1,3,4-thiadiazol-2-amine (0.397 mmol) and 58 mg of 2-chloro-1,3-dimethylimidazonium tetrafluoroborate (0.265 mmol) were dissolved in 2 ml of DMF, and 46 μl of DIPEA (0.264 mmol) was added, followed by stirring at 50° C. for 16 hours. After completion of the reaction, water was added to precipitate, washed with water and ethyl ether, and filtered to give 29 mg of the solid title compound (0.069 mmol) in 52% yield.

$^1$H NMR (300 MHz, DMSO-$d_6$) δ 12.91-13.20 (m, 2H), 8.23 (s, 1H), 7.84 (d, J=7.7 Hz, 2H), 7.30-7.37 (m, 2H), 7.21-7.28 (m, 1H), 4.33 (s, 2H)

\<Example 31\> Preparation of 2-((1-(4,4-difluorocyclohexyl)-4-oxo-4,5-dihydro-1H-pyrazolo[3,4-d]pyrimidin-6-yl)thio)-N-(5-bromo-1,3,4-thiadiazol-2-yl)propanamide

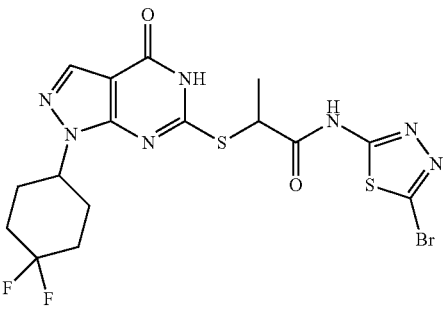 [SMILES: CC(Sc1nc2c(cnn2C2CCC(F)(F)CC2)c(=O)[nH]1)C(=O)Nc1nnc(Br)s1]

Step 1: Preparation of 2-((1-(4,4-difluorocyclohexyl)-4-oxo-4,5-dihydro-1H-pyrazolo[3,4-d]pyrimidin-6-yl)thio)-N-(5-bromo-1,3,4-thiadiazol-2-yl)propanamide

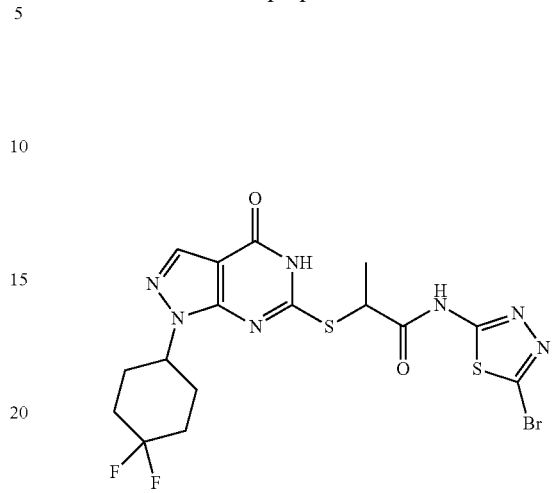

56 mg of 2-((1-(4,4-difluorocyclohexyl)-4-oxo-4,5-dihydro-1H-pyrazolo[3,4-d]pyrimidin-6-yl)thio)acetic acid (0.156 mmol) obtained in Preparation Example 18, 84 mg of 5-bromo-1,3,4-thiadiazol-2-amine (0.468 mmol), and 80 mg of CDMT (0.313 mmol) were dissolved in 2 ml of DMF, and 34 μl of NMM (0.313 mmol) was added, followed by stirring at 50° C. for 16 hours. After completion of the reaction, the resultant was extracted with ethyl acetate and washed with water and saturated brine. The filtrate concentrated under reduced pressure was purified by column chromatography (hexane:ethyl acetate=1:1, v/v) to give 36 mg of the solid title compound (0.069 mmol) in 44% yield.

Rf=0.29 (hexane:ethyl acetate=1:1, v/v)

$^1$H NMR (300 MHz, DMSO-$d_6$) δ 13.39 (brs, 1H), 12.63 (brs, 1H), 7.97 (s, 1H), 4.69 (q, J=7.2 Hz, 1H), 4.48-4.60 (m, 1H), 1.65-2.28 (m, 8H), 1.59 (d, J=7.2 Hz, 3H)

\<Example 32\> Preparation of N-(5-bromo-1,3,4-thiadiazol-2-yl)-2-((4-oxo-1-(tetrahydro-2H-thiopyran-4-yl)-4,5-dihydro-1H-pyrazolo[3,4-d]pyrimidin-6-yl)thio)acetamide

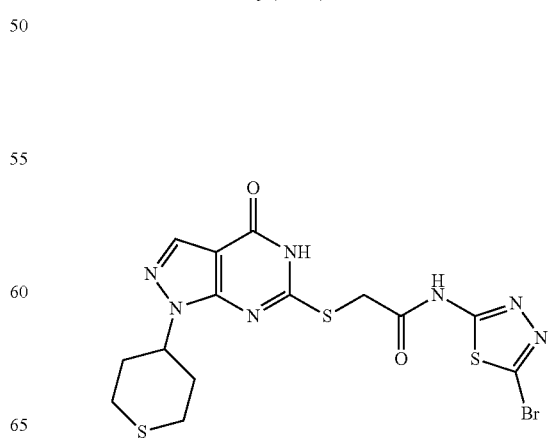

Step 1: Preparation of N-(5-bromo-1,3,4-thiadiazol-2-yl)-2-((4-oxo-1-(tetrahydro-2H-thiopyran-4-yl)-4,5-dihydro-1H-pyrazolo[3,4-d]pyrimidin-6-yl)thio)acetamide

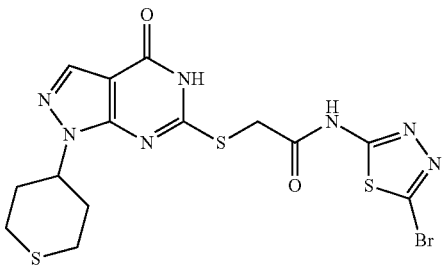 [SMILES: O=C(CSc1nc2c(cnn2C2CCSCC2)c(=O)[nH]1)Nc1nnc(Br)s1]

50 mg of 2-((4-oxo-1-(tetrahydro-2H-thiopyran-4-yl)-4,5-dihydro-1H-pyrazolo[3,4-d]pyrimidin-6-yl)thio)acetic acid (0.153 mmol) obtained in Preparation Example 20, 41 mg of 5-bromo-1,3,4-thiadiazol-2-amine (0.229 mmol), and 78 mg of CMPI (0.306 mmol) were dissolved in 2 ml of DMF, and 53 µl of DIPEA (0.306 mmol) was added, and stirred at 50° C. for 16 hours. After completion of the reaction, water was added to precipitate, washed with water and ethyl ether, and filtered to give 17.9 mg of the solid title compound (0.037 mmol) in 24% yield.

$^1$H NMR (300 MHz, DMSO-$d_6$) δ 13.37 (brs, 1H), 12.61 (brs, 1H), 7.96 (s, 1H), 4.31-3.49 (m, 1H), 4.27 (s, 2H), 2.51-2.60 (m, 4H), 1.84-2.05 (m, 4H)

<Example 33> Preparation of N-(5-bromo-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio)acetamide

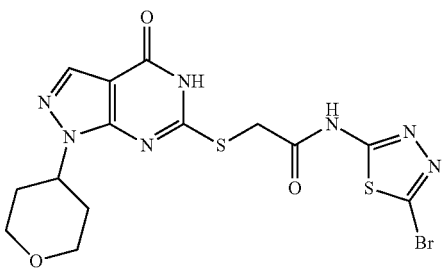

Step 1: Preparation of N-(5-bromo-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio)acetamide

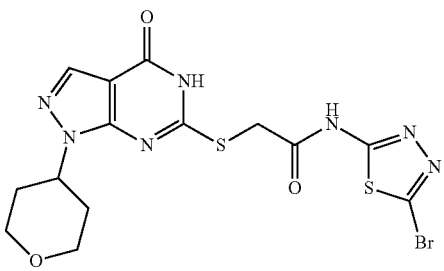 [SMILES: O=C(CSc1nc2c(cnn2C2CCOCC2)c(=O)[nH]1)Nc1nnc(Br)s1]

45 mg of 2-((4-oxo-1-(tetrahydro-2H-pyran-4-yl)-4,5-dihydro-1H-pyrazolo[3,4-d]pyrimidin-6-yl)thio)acetic acid (0.145 mmol) obtained in Preparation Example 17, 78 mg of 5-bromo-1,3,4-thiadiazol-2-amine (0.435 mmol), and 74 mg of CMPI (0.290 mmol) was dissolved in 2 ml of DMF, and 51 µl of DIPEA (0.290 mmol) was added, followed by stirring at 50° C. for 16 hours. After completion of the reaction, the resultant was extracted with ethyl acetate and washed with water and saturated brine. The filtrate concentrated under reduced pressure was purified by column chromatography (hexane:ethyl acetate=1:1->methanol/dichloromethane 3%, v/v) to give 16.1 mg of the solid title compound (0.034 mmol) in 24% yield.

Rf=0.11 (hexane:ethyl acetate=1:1, v/v)

$^1$H NMR (300 MHz, DMSO-$d_6$) δ 13.39 (brs, 1H), 12.64 (brs, 1H), 7.96 (s, 1H), 4.45-4.59 (m, 1H), 4.26 (s, 2H), 3.73-3.84 (m, 2H), 3.13-3.25 (m, 2H), 1.86-2.04 (m, 2H)

Preparation Example 21> Preparation of 2-((1-cyclohexyl-4-oxo-4,5-dihydro-1H-pyrazolo[3,4-d]pyrimidin-6-yl)thio)acetic acid

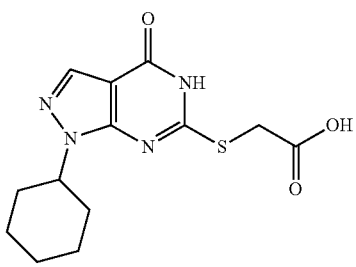 [SMILES: O=C(O)CSc1nc2c(cnn2C2CCCCC2)c(=O)[nH]1]

Step 1: Preparation of 4,6-dichloro-1-cyclohexyl-1H-pyrazolo[3,4-d]pyrimidine

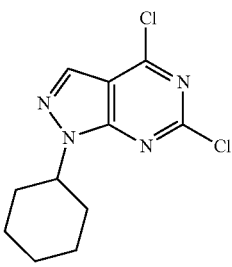 [SMILES: Clc1nc(Cl)c2cnn(C3CCCCC3)c2n1]

4.39 g of 2,4,6-trichloropyrimidine-5-carbaldehyde (20.71 mmol) was dissolved in 50 ml of ethanol, and 3.12 g of cyclohexyl hydrazine hydrogen chloride (20.71 mmol) and 11 ml of N,N-diisopropylethylamine (62.13 mmol) were added at −78° C. and stirred for 3 hours. After completion of the reaction, the resultant was extracted with 200 ml of ethyl acetate, washed with 200 ml of an inorganic salt solution, dried over anhydrous sodium sulfate (Na$_2$SO$_4$), and concentrated under reduced pressure. The residue was purified by column chromatography (hexane:ethyl acetate=10:1, v/v) to give 5.2 g of the title compound (19.18 mmol) in 92% yield.

Rf=0.39 (hexane:ethyl acetate=10:1, v/v)

¹H NMR (500 MHz, CDCl₃) δ 8.15 (s, 1H), 4.75-4.82 (m, 1H), 2.01-2.08 (m, 2H), 1.93-1.99 (m, 2H), 1.77-1.81 (m, 1H), 1.48-1.57 (m, 2H), 1.30-1.39 (m, 1H), 1.01-1.04 (m, 2H)

Step 2: Preparation of 6-chloro-1-cyclohexyl-1,5-dihydro-4H-pyrazolo[3,4-d]pyrimidin-4-one

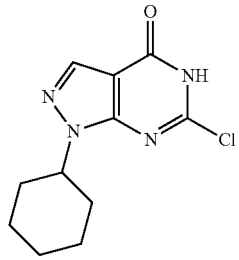 [SMILES: O=c1[nH]c(Cl)nc2c1cnn2C1CCCCC1]

5 g of 4,6-dichloro-1-cyclohexyl-1H-pyrazolo[3,4-d]pyrimidine (18.44 mmol) prepared in Step 1 above was dissolved in 12 ml of THF, and 19 ml of 2N sodium hydroxide (36.88 mmol) was added and stirred under reflux for 15 hours. After completion of the reaction, the mixture was acidified with 6N hydrochloric acid, and the precipitated solid compound was filtered to give 4.6 g of the title compound (18.20 mmol) in 98% yield.

Rf=0.35 (dichloromethane:methanol=20:1, v/v)

¹H NMR (500 MHz, DMSO-d₆) δ 13.18 (br s, 1H0, 8.07 (s, 1H), 4.46-4.52 (m, 1H), 1.80-1.87 (m, 4H), 1.66-1.69 (m, 1H), 1.40-1.48 (m, 2H), 1.18-1.25 (m, 1H)

Step 3: Preparation of ethyl 2-((1-cyclohexyl-4-oxo-4,5-dihydro-1H-pyrazolo[3,4-d]pyrimidin-6-yl)thio)acetate

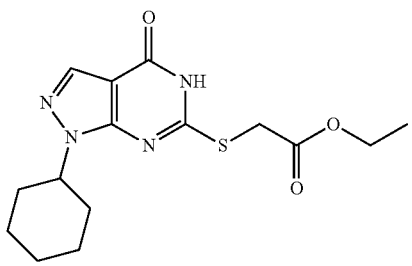 [SMILES: CCOC(=O)CSc1nc2c(cnn2C2CCCCC2)c(=O)[nH]1]

400 mg of 6-chloro-1-cyclohexyl-1,5-dihydro-4H-pyrazolo[3,4-d]pyridin-4-one (1.583 mmol) obtained in Step 2 above, 642 mg of potassium carbonate (4.749 mmol)), and 363 μl of ethyl thioglycolate (3.324 mmol) were dissolved in 5 ml of DMF and stirred at 90° C. for 3 hours. After completion of the reaction, the resultant was extracted with ethyl acetate and tetrahydrofuran, followed by washing with water, 1N hydrochloric acid, and saturated brine. The filtrate concentrated under reduced pressure was purified by column chromatography (hexane:ethyl acetate=1:1, v/v) to give 376 mg of the solid title compound (1.118 mmol) in 71% yield.

Rf=0.52 (normal hexane:ethyl acetate=1:1, v/v)

¹H NMR (300 MHz, CDCl₃) δ 10.58 (brs, 1H), 8.00 (s, 1H), 4.45-4.57 (m, 1H), 4.25 (q, J=7.1 Hz, 2H), 3.99 (s, 2H), 1.89-2.04 (m, 6H), 1.69-1.80 (m, 2H), 1.35-1.53 (m, 2H), 1.31 (t, J=7.1 Hz, 3H)

Step 4: Preparation of 2-((1-cyclohexyl-4-oxo-4,5-dihydro-1H-pyrazolo[3,4-d]pyrimidin-6-yl)thio) acetic acid

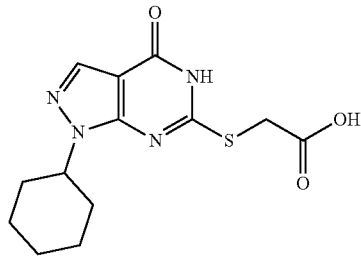 [SMILES: O=C(O)CSc1nc2c(cnn2C2CCCCC2)c(=O)[nH]1]

370 mg of ethyl 2-((1-cyclohexyl-4-oxo-4,5-dihydro-1H-pyrazolo[3,4-d]pyrimidin-6-yl)thio)acetate (1.118 mmol) prepared in Step 3 above was dissolved in 5 ml of tetrahydrofuran, and 2N sodium hydroxide was added, followed by stirring at room temperature for 16 hours. After completion of the reaction, it was neutralized with 1N hydrochloric acid, extracted with ethyl acetate and tetrahydrofuran, and washed with water and saturated brine. The resultant was concentrated under reduced pressure to give 354 mg of the solid title compound (1.118 mmol) in 99% yield.

¹H NMR (300 MHz, DMSO-d₆) δ 12.85 (brs, 1H), 12.53 (brs, 1H), 7.92 (s, 1H), 4.38-4.52 (m, 1H), 3.97 (s, 2H), 1.61-1.92 (m, 7H), 1.18-1.50 (m, 3H)

<Example 34> Preparation of N-(5-(ethylthio)-1,3,4-thiadiazol-2-yl)-2-((4-oxo-1-cyclohexyl-4,5-dihydro-1H-pyrazolo[3,4-d]pyrimidin-6-yl)thio)acetamide

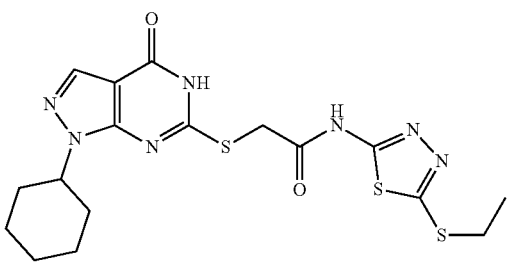 [SMILES: CCSc1nnc(NC(=O)CSc2nc3c(cnn3C3CCCCC3)c(=O)[nH]2)s1]

Step 1: Preparation of N-(5-(ethylthio)-1,3,4-thiadiazol-2-yl)-2-((4-oxo-1-cyclohexyl-4,5-dihydro-1H-pyrazolo[3,4-d]pyrimidin-6-yl)thio)acetamide

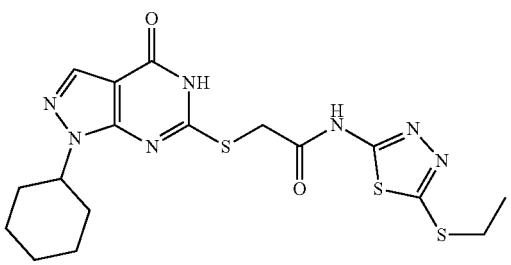 [SMILES: CCSc1nnc(NC(=O)CSc2nc3c(cnn3C3CCCCC3)c(=O)[nH]2)s1]

40 mg of 2-((1-cyclohexyl-4-oxo-4,5-dihydro-1H-pyrazolo[3,4-d]pyrimidin-6-yl)thio)acetic acid (0.130 mmol) obtained in Preparation Example 21, 63 mg of 5-(ethylthio)-1,3,4-thiadiazol-2-amine (0.390 mmol), and 66 mg of CMPI (0.260 mmol) were dissolved in 2 ml of DMF, and then 45 µl of DIPEA (0.260 mmol) was added, followed by stirring at 50° C. for 18 hours. After completion of the reaction, the resultant was extracted with ethyl acetate and tetrahydrofuran, followed by washing with water and saturated brine. The filtrate concentrated under reduced pressure was purified by column chromatography (hexane:ethyl acetate=1:1->1:2, v/v) to give 13.4 mg of the solid title compound (0.030 mmol) in 23% yield.

Rf=0.18 (hexane:ethyl acetate=1:1, v/v)

$^1$H NMR (300 MHz, DMSO-d$_6$) δ 7.91 (s, 1H), 4.24-4.31 (m, 1H), 4.23 (s, 2H), 3.20 (q, J=7.3 Hz, 2H), 1.47-1.77 (m, 7H), 1.31 (t, J=7.3 Hz, 3H), 1.03-1.17 (m, 3H)

<Example 35> Preparation of N-(5-bromo-1,3,4-thiadiazol-2-yl)-2-((4-oxo-1-cyclohexyl-4,5-dihydro-1H-pyrazolo[3,4-d]pyrimidin-6-yl)thio)acetamide Step 1: Preparation of N-(5-bromo-1,3,4-thiadiazol-2-yl)-2-((4-oxo-1-cyclohexyl-4,5-dihydro-1H-pyrazolo[3,4-d]pyrimidin-6-yl)thio)acetamide 40 mg of 2-((1-cyclohexyl-4-oxo-4,5-dihydro-1H-pyrazolo[3,4-d]pyrimidin-6-yl)thio)acetic acid (0.130 mmol) obtained in Preparation Example 21, 66 mg of 5-bromo-1,3,4-thiadiazol-2-amine (0.390 mmol), and 66 mg of CMPI (0.260 mmol) were dissolved in 2 ml of DMF, and 45 µl of DIPEA (0.260 mmol) was added, followed by stirring at 50° C. for 18 hours. After completion of the reaction, water was added to precipitate, washed with water and ethyl ether, and filtered to give 9.7 mg of the solid title compound (0.021 mmol) in 16% yield.

$^1$H NMR (300 MHz, DMSO-d6) δ 13.36 (brs, 1H), 12.58 (brs, 1H), 7.92 (s, 1H), 4.17-4.30 (m, 3H), 1.48-1.90 (m, 7H), 1.01-1.26 (m, 3H)

<Example 36> Preparation of N-(5-chloro-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio)acetamide Step 1: Preparation of N-(5-chloro-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio)acetamide 40 mg of 2-((4-oxo-1-(tetrahydro-2H-pyran-4-yl)-4,5-dihydro-1H-pyrazolo[3,4-d]pyrimidin-6-yl)thio)acetic acid (0.129 mmol) obtained in Preparation Example 17, 66 mg of 5-chloro-1,3,4-thiadiazol-2-amine (0.258 mmol), and 66 mg of CMPI (0.258 mmol) was dissolved in 2 ml of DMF, and 45 µl of DIPEA (0.258 mmol) was added, followed by stirring at 50° C. for 16 hours. After completion of the reaction, the resultant was extracted with ethyl acetate and washed with water and saturated brine. The filtrate concentrated under reduced pressure was purified by column chromatography (hexane:ethyl acetate=1:1->methanol/dichloromethane 3%, v/v) to give 21.9 mg of the solid title compound (0.051 mmol) in 40% yield.

Rf=0.09 (hexane:ethyl acetate=1:1, v/v)

$^1$H NMR (300 MHz, DMSO-d6) δ 13.39 (brs, 1H), 12.64 (brs, 1H), 7.99 (s, 1H), 4.47-4.60 (m, 1H), 4.26 (s, 2H), 3.75-3.85 (m, 2H), 3.14-3.25 (m, 2H), 1.86-2.03 (m, 2H), 1.50-1.60 (m, 2H), 1.86-2.04 (m, 2H)

Preparation Example 22> Preparation of 2-((1-iso-propyl-4-oxo-4,5-dihydro-1H-pyrazolo[3,4-d]pyrimidin-6-yl)thio)acetic acid

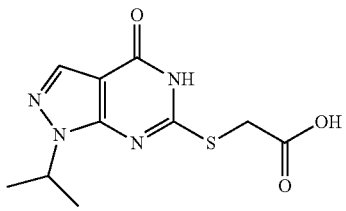 [SMILES: CC(C)n1ncc2c(=O)[nH]c(SCC(=O)O)nc21]

Step 1: Preparation of 4,6-dichloro-1-isopropyl-1H-pyrazolo[3,4-d]pyrimidine

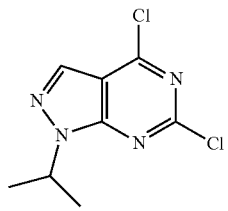

2.22 g of 2,4,6-trichloropyrimidine-5-carbaldehyde (10.49 mmol) was dissolved in 30 ml of ethanol, and 1.16 g of isopropyl hydrazine hydrogen chloride (10.49 mmol) and 5.5 ml of N,N-diisopropylethylamine (31.47 mmol) was added at −78° C. and stirred for 3 hours. After completion of the reaction, the resultant was extracted with 200 ml of ethyl acetate, washed with 200 ml of an inorganic salt solution, dried over anhydrous sodium sulfate (Na$_2$SO$_4$), and concentrated under reduced pressure. The residue was purified by column chromatography (hexane:ethyl acetate=10:1, v/v) to give 2.1 g of the title compound (9.08 mmol) in 87% yield.

Rf=0.48 (hexane:ethyl acetate=10:1, v/v)

$^1$H NMR (500 MHz, CDCl$_3$) δ 8.16 (s, 1H), 5.16-5.22 (m, 1H), 1.60 (d, J=6.7 Hz, 6H)

Step 2: Preparation of 6-chloro-1-isopropyl-1,5-dihydro-4H-pyrazolo[3,4-d]pyrimidin-4-one

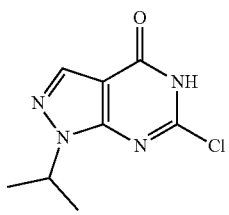

2 g of 4,6-dichloro-1-isopropyl-1H-pyrazolo[3,4-d]pyrimidine (8.65 mmol) prepared in Step 1 was dissolved in 12 ml of THF, and 8.6 ml of 2N sodium hydroxide (17.13 mmol) was added and stirred under reflux for 15 hours. After completion of the reaction, the mixture was acidified with 6N hydrochloric acid, and the precipitated solid compound was filtered to give 1.7 g of the title compound (7.99 mmol) in 92% yield.

Rf=0.29 (dichloromethane:methanol=20:1, v/v)

$^1$H NMR (500 MHz, DMSO-d$_6$) δ 13.16 (br s, 1H), 8.08 (s, 1H), 4.85-4.91 (m, 1H), 1.44 (d, J=7.0 Hz, 6H)

Step 3: Preparation of ethyl 2-((1-isopropyl-4-oxo-4,5-dihydro-1H-pyrazolo[3,4-d]pyrimidin-6-yl)thio)acetate

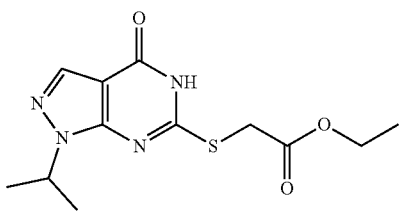 [SMILES: CCOC(=O)CSc1nc2c(cnn2C(C)C)c(=O)[nH]1]

300 mg of 6-chloro-1-isopropyl-1,5-dihydro-4H-pyrazolo[3,4-d]pyridin-4-one (1.411 mmol) obtained in Step 2, 572 mg of potassium carbonate (4.233 mmol), and 324 μl of ethyl thioglycolate (2.963 mmol) were dissolved in 5 ml of DMF and stirred at 90° C. for 3 hours. After completion of the reaction, the resultant was extracted with ethyl acetate and tetrahydrofuran, followed by washing with water, 1N hydrochloric acid, and saturated brine. The filtrate concentrated under reduced pressure was purified by column chromatography (hexane:ethyl acetate=1:1->methanol/dichloromethane=5%, v/v) to give 287 mg of the solid title compound (0.968 mmol) in 69% yield.

Rf=0.44 (normal hexane:ethyl acetate=1:1, v/v)

$^1$H NMR (300 MHz, CDCl$_3$) δ 10.78 (brs, 1H), 8.04 (s, 1H), 4.89-5.00 (m, 1H), 4.25 (q, J=7.1 Hz, 2H), 4.00 (s, 2H), 1.54 (d, J=6.9 Hz, 6H), 1.31 (t, J=7.1 Hz, 3H)

Step 4: Preparation of 2-((1-isopropyl-4-oxo-4,5-dihydro-1H-pyrazolo[3,4-d]pyrimidin-6-yl)thio)acetic acid

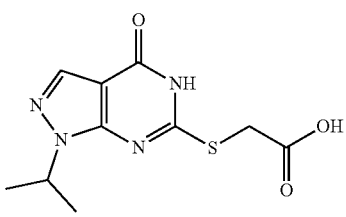 [SMILES: CC(C)n1ncc2c(=O)[nH]c(SCC(=O)O)nc21]

287 mg of ethyl 2-((1-isopropyl-4-oxo-4,5-dihydro-1H-pyrazolo[3,4-d]pyrimidin-6-yl)thio)acetate (0.968 mmol) prepared in Step 3 above was dissolved in 5 ml of tetrahydrofuran, and 2N sodium hydroxide was added, followed by stirring at room temperature for 16 hours. After completion of the reaction, it was neutralized with 1N hydrochloric acid, extracted with ethyl acetate and tetrahydrofuran, and washed with water and saturated brine. The resultant was concentrated under reduced pressure to give 252 mg of the solid title compound (0.939 mmol) in 97% yield.

$^1$H MMR (300 MHz, DMSO-d$_6$) δ 12.90 (brs, 1H), 12.56 (brs, 1H), 7.95 (s, 1H), 4.80-4.90 (m, 1H), 3.90 (s, 2H), 1.42 (d, J=6.6 Hz, 6H)

<Example 37> Preparation of N-(5-(ethylthio)-1,3,4-thiadiazol-2-yl)-2-((1-isopropyl-4-oxo-4,5-dihydro-1H-pyrazolo[3,4-d]pyrimidin-6-yl)thio)acetamide

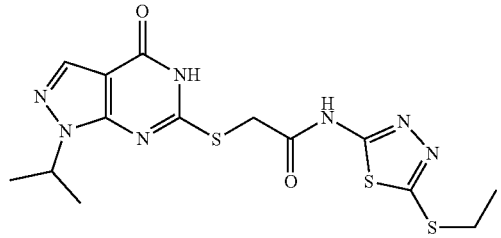 [SMILES: CCSc1nnc(NC(=O)CSc2nc3c(cnn3C(C)C)c(=O)[nH]2)s1]

Step 1: Preparation of N-(5-(ethylthio)-1,3,4-thiadiazol-2-yl)-2-((1-isopropyl-4-oxo-4,5-dihydro-1H-pyrazolo[3,4-d]pyrimidin-6-yl)thio)acetamide

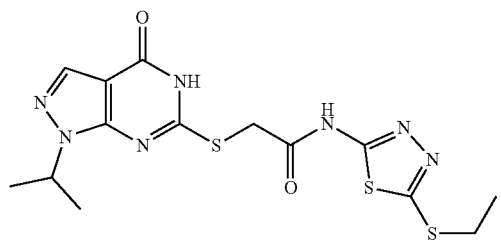 [SMILES: CCSc1nnc(NC(=O)CSc2nc3c(cnn3C(C)C)c(=O)[nH]2)s1]

40 mg of 2-((1-isopropyl-4-oxo-4,5-dihydro-1H-pyrazolo[3,4-d]pyrimidin-6-yl)thio)acetic acid (0.149 mmol) obtained in Preparation Example 22, 36 mg of 5-(ethylthio)-1,3,4-thiadiazol-2-amine (0.224 mmol) obtained in Preparation Example 4, and 76 mg of CMPI (0.298 mmol) was dissolved in 2 ml of DMF, and 52 µl of DIPEA (0.298 mmol) was added, followed by stirring at 50° C. for 18 hours. After completion of the reaction, the resultant was extracted was performed with ethyl acetate and tetrahydrofuran, followed by washing with water and saturated brine. The filtrate concentrated under reduced pressure was purified by column chromatography (hexane:ethyl acetate=1:1->methanol/dichloromethane=5%, v/v) to give 32.3 mg of the solid title compound (0.078 mmol) in 53% yield.

Rf=0.13 (hexane:ethyl acetate=1:1, v/v)

$^1$H NMR (300 MHz, DMSO-$d_6$) δ 13.11 (brs, 1H), 12.61 (brs, 1H), 7.93 (s, 1H), 4.69-4.79 (m, 1H), 4.22 (s, 2H), 3.20 (q, J=7.2 Hz, 2H), 1.30 (t, J=7.2 Hz, 3H), 1.15 (d, J=6.6 Hz, 6H)

<Example 38> Preparation of N-(5-bromo-1,3,4-thiadiazol-2-yl)-2-((1-isopropyl-4-oxo-4,5-dihydro-1H-pyrazolo[3,4-d]pyrimidin-6-yl)thio)acetamide

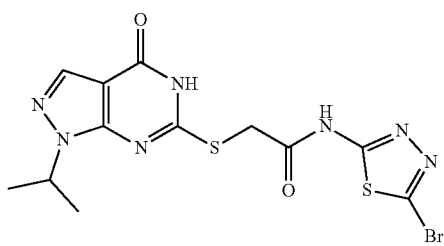 [SMILES: CC(C)n1ncc2c(=O)[nH]c(SCC(=O)Nc3nnc(Br)s3)nc21]

Step 1: Preparation of N-(5-bromo-1,3,4-thiadiazol-2-yl)-2-((1-isopropyl-4-oxo-4,5-dihydro-1H-pyrazolo[3,4-d]pyrimidin-6-yl)thio)acetamide

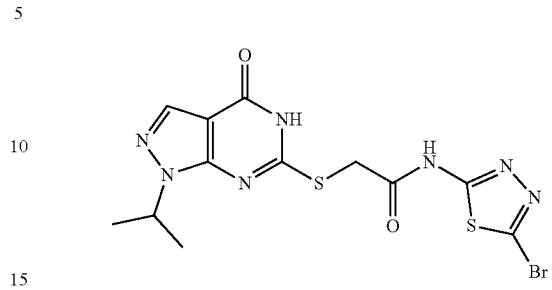

40 mg of 2-((1-isopropyl-4-oxo-4,5-dihydro-1H-pyrazolo[3,4-d]pyrimidin-6-yl)thio)acetic acid (0.149 mmol) obtained in Preparation Example 22, 40 mg of 5-bromo-1,3,4-thiadiazol-2-amine (0.224 mmol), and 76 mg of CMPI (0.298 mmol) were dissolved in 2 ml of DMF, and 52 µl of DIPEA (0.298 mmol) was added, followed by stirring at 50° C. for 18 hours. After completion of the reaction, the resultant was extracted with ethyl acetate and tetrahydrofuran, followed by washing with water and saturated brine. The filtrate concentrated under reduced pressure was purified by column chromatography (hexane:ethyl acetate=1:1->methanol/dichloromethane=5%, v/v) to give 22.2 mg of the solid title compound (0.052 mmol) in 53% yield.

Rf=0.11 (hexane:ethyl acetate=1:1, v/v)

$^1$H NMR (300 MHz, DMSO-$d_6$) δ 13.41 (brs, 1H), 12.59 (brs, 1H), 7.93 (s, 1H), 4.68-4.79 (m, 1H), 4.25 (s, 2H), 1.15 (d, J=6.6 Hz, 6H)

<Example 39> Preparation of N-(5-chloro-1,3,4-thiadiazol-2-yl)-2-((4-oxo-1-(tetrahydro-2H-thiopyran-4-yl)-4,5-dihydro-1H-pyrazolo[3,4-d]pyrimidin-6-yl)thio)acetamide

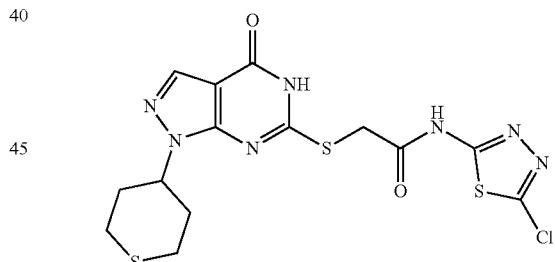

Step 1: Preparation of N-(5-chloro-1,3,4-thiadiazol-2-yl)-2-((4-oxo-1-(tetrahydro-2H-thiopyran-4-yl)-4,5-dihydro-1H-pyrazolo[3,4-d]pyrimidin-6-yl)thio)acetamide

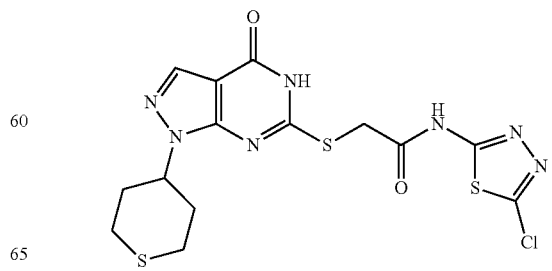

40 mg of 2-((4-oxo-1-(tetrahydro-2H-thiopyran-4-yl)-4,5-dihydro-1H-pyrazolo[3,4-d]pyrimidin-6-yl)thio)acetic acid (0.123 mmol) obtained in Preparation Example 20, 25 mg of 5-chloro-1,3,4-thiadiazol-2-amine (0.184 mmol), and 63 mg of CMPI (0.246 mmol) were dissolved in 2 ml of DMF, and 43 μl of DIPEA (0.246 mmol) was added, followed by stirring at 50° C. for 16 hours. After completion of the reaction, water was added to precipitate, washed with water and ethyl ether, and filtered to give 14.7 mg of the solid title compound (0.033 mmol) in 27% yield.

$^1$H NMR (300 MHz, DMSO-$d_6$) δ 13.37 (brs, 1H), 12.65 (brs, 1H), 7.96 (s, 1H), 4.31-4.41 (m, 1H), 4.26 (s, 2H), 2.53-2.62 (m, 4H), 1.85-2.08 (m, 4H)

Preparation Example 23> Preparation of 2-((1-cyclopropyl-4-oxo-4,5-dihydro-1H-pyrazolo[3,4-d]pyrimidin-6-yl)thio)acetic acid

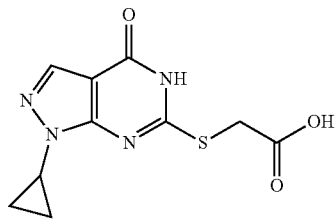 [SMILES: O=C(O)CSc1nc2c(cnn2C2CC2)c(=O)[nH]1]

Step 1: Preparation of 4,6-dichloro-1-cyclopropyl-1H-pyrazolo[3,4-d]pyrimidine

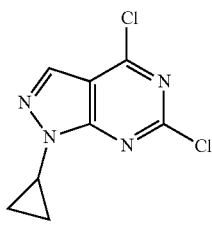 [SMILES: Clc1nc(Cl)c2cnn(C3CC3)c2n1]

1.95 g of 2,4,6-trichloropyrimidine-5-carbaldehyde (9.21 mmol) was dissolved in 30 ml of ethanol, and 1 g of cyclopropyl hydrazine hydrogen chloride (9.21 mmol) and 4.8 ml of N,N-diisopropylethylamine (27.63 mmol) were added at −78° C. and stirred for 3 hours. After completion of the reaction, the resultant was extracted with 200 ml of ethyl acetate, washed with 200 ml of an inorganic salt solution, dried over anhydrous sodium sulfate (Na$_2$SO$_4$), and concentrated under reduced pressure. The residue was purified by column chromatography (hexane:ethyl acetate=10:1, v/v) to give 950 mg of the title compound (4.15 mmol) in 45% yield.

Rf=0.45 (hexane:ethyl acetate=10:1, v/v)

$^1$H NMR (500 MHz, CDCl$_3$) δ 8.10 (s, 1H), 3.88-3.92 (m, 1H), 1.35-1.38 (m, 2H), 1.21-1.25 (m, 2H)

Step 2: Preparation of 6-chloro-1-cyclopropyl-1,5-dihydro-4H-pyrazolo[3,4-d]pyrimidin-4-one

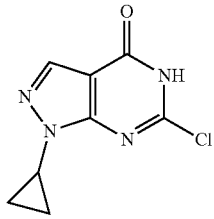 [SMILES: O=c1[nH]c(Cl)nc2c1cnn2C1CC1]

930 mg of 4,6-dichloro-1-cyclopropyl-1H-pyrazolo[3,4-d]pyrimidine (4.06 mmol) prepared in Step 1 was dissolved in 12 ml of THF, and 4 ml of 2N sodium hydroxide (8.12 mmol) was added and stirred under reflux for 15 hours. After completion of the reaction, the mixture was acidified with 6N hydrochloric acid, and the precipitated solid compound was filtered to give 680 mg of the title compound (3.23 mmol) in 80% yield.

Rf=0.28 (dichloromethane:methanol=20:1, v/v)

$^1$H NMR (500 MHz, DMSO-$d_6$) δ 13.20 (br s, 1H), 8.02 (s, 1H), 3.78-3.82 (m, 1H), 1.05-1.15 (m, 4H)

Step 3: Preparation of ethyl 2-((1-cyclopropyl-4-oxo-4,5-dihydro-1H-pyrazolo[3,4-d]pyrimidin-6-yl)thio)acetate

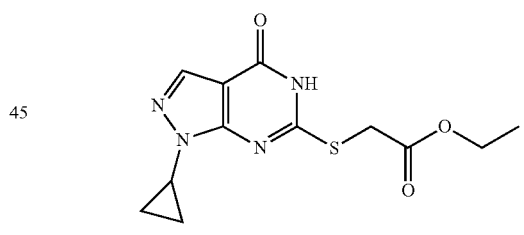

300 mg of 6-chloro-1-cyclopropyl-1,5-dihydro-4H-pyrazolo[3,4-d]pyridin-4-one (1.424 mmol) obtained in Step 2, 578 mg of potassium carbonate (4.273 mmol), and 327 μl of ethyl thioglycolate (2.990 mmol) were dissolved in 5 ml of DMF and stirred at 90° C. for 3 hours. After completion of the reaction, the resultant was extracted with ethyl acetate and tetrahydrofuran, followed by washing with water, 1N hydrochloric acid, and saturated brine. The filtrate concentrated under reduced pressure was purified by column chromatography (hexane:ethyl acetate=1:1->methanol/dichloromethane=5%, v/v) to give 345 mg of the solid title compound (1.172 mmol) in 82% yield.

Rf=0.28 (normal hexane:ethyl acetate=1:1, v/v)

$^1$H NMR (300 MHz, CDCl$_3$) δ 10.91 (brs, 1H), 7.97 (s, 1H), 4.26 (q, J=7.1 Hz, 2H), 4.03 (s, 2H), 3.69-3.79 (m, 1H), 1.22-1.35 (m, 5H), 1.05-1.13 (m, 2H)

Step 4: Preparation of 2-((1-cyclopropyl-4-oxo-4,5-dihydro-1H-pyrazolo[3,4-d]pyrimidin-6-yl)thio) acetic acid

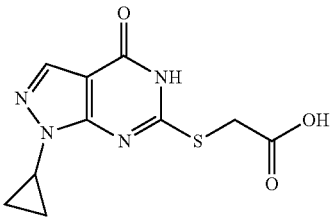 [SMILES: O=C(O)CSc1nc2c(cnn2C2CC2)c(=O)[nH]1]

336 mg of ethyl 2-((1-cyclopropyl-4-oxo-4,5-dihydro-1H-pyrazolo[3,4-d]pyrimidin-6-yl)thio)acetate (1.142 mmol) prepared in Step 3 above was dissolved in 5 ml of tetrahydrofuran, and 2N sodium hydroxide was added, followed by stirring at room temperature for 16 hours. After completion of the reaction, it was neutralized with 1N hydrochloric acid, extracted with ethyl acetate and tetrahydrofuran, and washed with water and saturated brine. The resultant was concentrated under reduced pressure to give 262 mg of the solid title compound (0.991 mmol) in 87% yield.

$^1$H MMR (300 MHz, DMSO-$d_6$) δ 12.89 (brs, 1H), 12.55 (brs, 1H), 7.91 (s, 1H), 4.03 (s, 2H), 3.70-3.80 (m, 1H), 0.98-1.18 (m, 4H)

<Example 40> Preparation of N-(5-(ethylthio)-1,3,4-thiadiazol-2-yl)-2-((1-cyclopropyl-4-oxo-4,5-dihydro-1H-pyrazolo[3,4-d]pyrimidin-6-yl)thio)acetamide

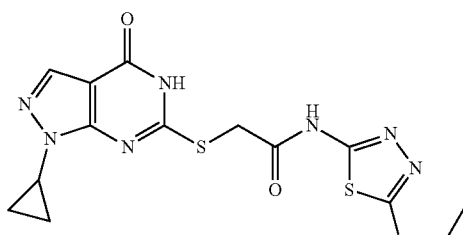

Step 1: Preparation of N-(5-(ethylthio)-1,3,4-thiadiazol-2-yl)-2-((1-cyclopropyl-4-oxo-4,5-dihydro-1H-pyrazolo[3,4-d]pyrimidin-6-yl)thio)acetamide

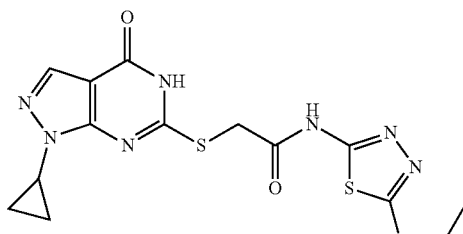

40 mg of 2-((1-cyclopropyl-4-oxo-4,5-dihydro-1H-pyrazolo[3,4-d]pyrimidin-6-yl)thio)acetic acid (0.150 mmol) obtained in Preparation Example 23, 36 mg of 5-(ethylthio)-1,3,4-thiadiazol-2-amine (0.224 mmol) obtained in Preparation Example 4, and 76 mg of CMPI (0.298 mmol) were dissolved in 2 ml DMF, and 52 µl of DIPEA (0.298 mmol) was added, followed by stirring at 50° C. for 18 hours. After completion of the reaction, water was added to precipitate, washed with water and ethyl ether, and filtered to give 8.5 mg of the solid title compound (0.021 mmol) in 14% yield.

$^1$H NMR (300 MHz, DMSO-d6) δ 12.40-13.15 (m, 2H), 7.88 (s, 1H), 4.26 (s, 2H), 3.59-3.70 (m, 1H), 3.21 (q, J=7.1 Hz, 2H), 1.32 (t, J=7.1 Hz, 3H), 0.92-1.00 (m, 2H)

<Example 41> Preparation of N-(5-bromo-1,3,4-thiadiazol-2-yl)-2-((1-cyclopropyl-4-oxo-4,5-dihydro-1H-pyrazolo[3,4-d]pyrimidin-6-yl)thio)acetamide

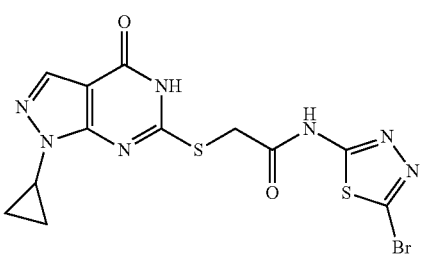 [SMILES: O=C(CSc1nc2c(cnn2C2CC2)c(=O)[nH]1)Nc1nnc(Br)s1]

Step 1: Preparation of N-(5-bromo-1,3,4-thiadiazol-2-yl)-2-((1-cyclopropyl-4-oxo-4,5-dihydro-1H-pyrazolo[3,4-d]pyrimidin-6-yl)thio)acetamide

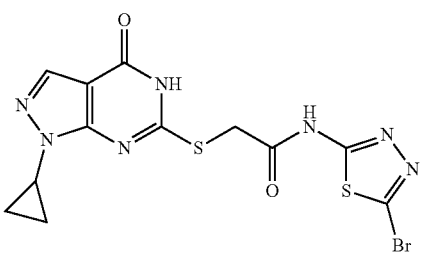 [SMILES: O=C(CSc1nc2c(cnn2C2CC2)c(=O)[nH]1)Nc1nnc(Br)s1]

40 mg of 2-((1-cyclopropyl-4-oxo-4,5-dihydro-1H-pyrazolo[3,4-d]pyrimidin-6-yl)thio)acetic acid (0.150 mmol) obtained in Preparation Example 23, 36 mg of 5-bromo-1,3,4-thiadiazol-2-amine (0.224 mmol), and 76 mg of CMPI (0.298 mmol) were dissolved in 2 ml of DMF, and 52 µl of DIPEA (0.298 mmol) was added, followed by stirring at 50° C. for 18 hours. After completion of the reaction, water was added to precipitate, washed with water and ethyl ether, and filtered to give 27.4 mg of the solid title compound (0.064 mmol) in 43% yield.

$^1$H NMR (300 MHz, DMSO-$d_6$) δ 13.36 (brs, 1H), 12.62 (brs, 1H), 7.88 (s, 1H), 4.29 (s, 2H), 3.58-3.67 (m, 1H), 0.93-1.00 (m, 2H), 0.73-0.81 (m, 2H)

<Example 42> Preparation of N-(5-chloro-1,3,4-thiadiazol-2-yl)-2-((4-oxo-1-cyclohexyl-4,5-dihydro-1H-pyrazolo[3,4-d]pyrimidin-6-yl)thio)acetamide

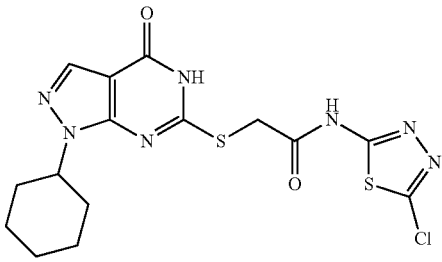 [SMILES: O=C(CSc1nc2c(cnn2C2CCCCC2)c(=O)[nH]1)Nc1nnc(Cl)s1]

Step 1: Preparation of N-(5-chloro-1,3,4-thiadiazol-2-yl)-2-((4-oxo-1-cyclohexyl-4,5-dihydro-1H-pyrazolo[3,4-d]pyrimidin-6-yl)thio)acetamide

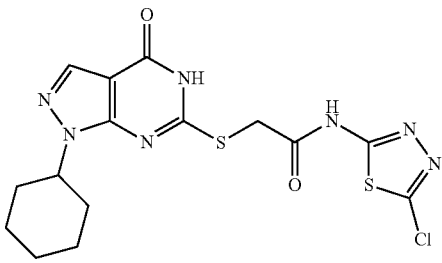 [SMILES: O=C(CSc1nc2c(cnn2C2CCCCC2)c(=O)[nH]1)Nc1nnc(Cl)s1]

40 mg of 2-((1-cyclohexyl-4-oxo-4,5-dihydro-1H-pyrazolo[3,4-d]pyrimidin-6-yl)thio)acetic acid (0.130 mmol) obtained in Preparation Example 21, 52 mg of 5-chloro-1,3,4-thiadiazol-2-amine (0.390 mmol), and 66 mg of CMPI (0.260 mmol) were dissolved in 2 ml of DMF, and 45 μl of DIPEA (0.260 mmol) was added and stirred at 50° C. for 18 hours. After completion of the reaction, water was added to precipitate, washed with water and ethyl ether, and filtered to give 19.5 mg of the solid title compound (0.046 mmol) in 35% yield.

$^1$H NMR (300 MHz, DMSO-d$_6$) δ 13.37 (brs, 1H), 12.59 (brs, 1H), 7.92 (s, 1H), 4.19-4.32 (m, 3H), 1.49-1.92 (m, 7H), 1.02-1.17 (m, 3H)

<Example 43> Preparation of N-(5-chloro-1,3,4-thiadiazol-2-yl)-2-((1-isopropyl-4-oxo-4,5-dihydro-1H-pyrazolo[3,4-d]pyrimidin-6-yl)thio)acetamide

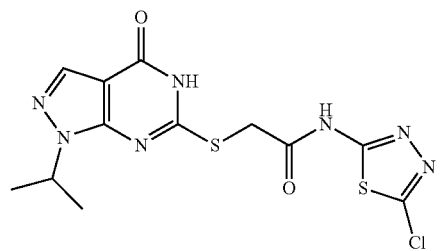 [SMILES: CC(C)n1ncc2c(=O)[nH]c(SCC(=O)Nc3nnc(Cl)s3)nc21]

Step 1: Preparation of N-(5-chloro-1,3,4-thiadiazol-2-yl)-2-((1-isopropyl-4-oxo-4,5-dihydro-1H-pyrazolo[3,4-d]pyrimidin-6-yl)thio)acetamide

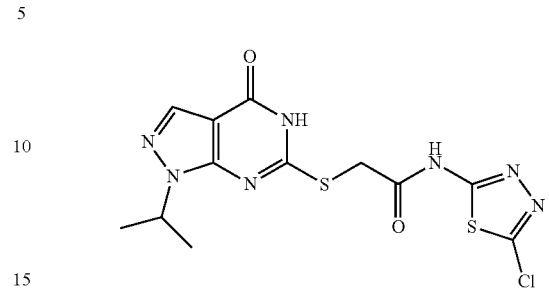

40 mg of 2-((1-isopropyl-4-oxo-4,5-dihydro-1H-pyrazolo[3,4-d]pyrimidin-6-yl)thio)acetic acid (0.149 mmol) obtained in Preparation Example 22, 34 mg of 5-chloro-1,3,4-thiadiazol-2-amine (0.224 mmol), and 76 mg of CMPI (0.298 mmol) were dissolved in 2 ml of DMF, and 52 μl of DIPEA (0.298 mmol) was added and stirred at 50° C. for 18 hours. After completion of the reaction, the resultant was extracted with ethyl acetate and tetrahydrofuran, followed by washing with water and saturated brine. The filtrate concentrated under reduced pressure was purified by column chromatography (hexane:ethyl acetate=1:1->methanol/dichloromethane=5%, v/v) to give 31.4 mg of the solid title compound (0.081 mmol) in 55% yield.

Rf=0.13 (hexane:ethyl acetate=1:1, v/v)

$^1$H NMR (500 MHz, DMSO-d$_6$) δ 13.42 (brs, 1H), 12.59 (brs, 1H), 7.93 (s, 1H), 4.69-4.78 (m, 1H), 4.25 (s, 2H), 1.16 (d, J=6.4 Hz, 6H)

<Example 44> Preparation of N-(5-chloro-1,3,4-thiadiazol-2-yl)-2-((1-cyclopropyl-4-oxo-4,5-dihydro-1H-pyrazolo[3,4-d]pyrimidin-6-yl)thio)acetamide

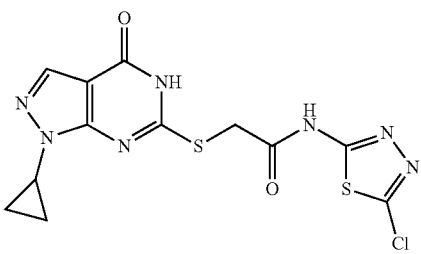 [SMILES: O=C(CSc1nc2c(cnn2C2CC2)c(=O)[nH]1)Nc1nnc(Cl)s1]

Step 1: Preparation of N-(5-chloro-1,3,4-thiadiazol-2-yl)-2-((1-cyclopropyl-4-oxo-4,5-dihydro-1H-pyrazolo[3,4-d]pyrimidin-6-yl)thio)acetamide

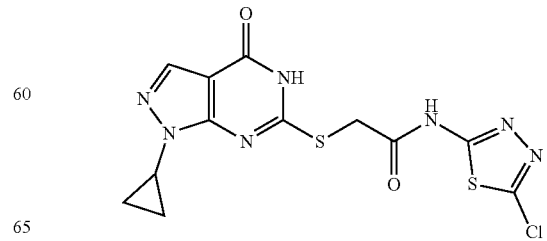

40 mg of 2-((1-cyclopropyl-4-oxo-4,5-dihydro-1H-pyrazolo[3,4-d]pyrimidin-6-yl)thio)acetic acid (0.150 mmol) obtained in Preparation Example 23, 36 mg of 5-chloro-1,3,4-thiadiazol-2-amine (0.224 mmol), and 76 mg of CMPI (0.298 mmol) were dissolved in 2 ml of DMF, and 52 µl of DIPEA (0.298 mmol) was added and stirred at 50° C. for 18 hours. After completion of the reaction, water was added to precipitate, washed with water and ethyl ether, and filtered to give 23.2 mg of the solid title compound (0.060 mmol) in 43% yield.

$^1$H NMR (500 MHz, DMSO-d$_6$) δ 13.37 (brs, 1H), 12.63 (brs, 1H), 7.89 (s, 1H), 4.29 (s, 2H), 3.61-3.66 (m, 1H), 0.94-0.99 (m, 2H), 0.75-0.81 (m, 2H)

Preparation Example 24> Preparation of 2-((1-(tetrahydro-2H-pyran-4-yl)-4-oxo-4,5-dihydro-1H-pyrazolo[3,4-d]pyrimidine-6-yl)thio)propanoic acid

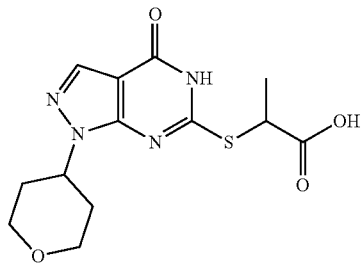 [SMILES: CC(Sc1nc2c(cnn2C2CCOCC2)c(=O)[nH]1)C(=O)O]

Step 1: Preparation of ethyl 2-((4-oxo-1-(tetrahydro-2H-pyran-4-yl)-4,5-dihydro-1H-pyrazolo[3,4-d]pyrimidin-6-yl)thio)acetate

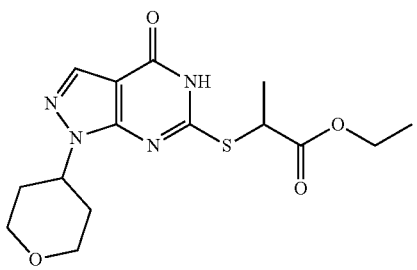 [SMILES: CCOC(=O)C(C)Sc1nc2c(cnn2C2CCOCC2)c(=O)[nH]1]

300 mg of 6-chloro-1-(tetrahydro-2H-pyran-4-yl)-1,5-dihydro-4H-pyrazolo[3,4-d]pyridin-4-one (1.178 mmol) obtained in Preparation Example 17 Step 2, 488 mg of potassium carbonate (3.534 mmol), and 319 µl of ethyl 2-mercaptopropionate (2.474 mmol) were dissolved in 5 ml DMF, followed by stirring at 90° C. for 5 hours and 30 minutes. After completion of the reaction, the resultant was extracted with ethyl acetate and washed with water, 1N hydrochloric acid, and saturated brine. The filtrate concentrated under reduced pressure was purified by column chromatography (hexane:ethyl acetate=2:1->1:1, v/v) to give 240 mg of the solid title compound (0.681 mmol) in 58% yield.

Rf=0.39 (normal hexane:ethyl acetate=1:1, v/v)

$^1$H NMR (300 MHz, CDCl$_3$) δ 10.83 (brs, 1H), 8.05 (s, 1H), 4.69-4.82 (m, 1H), 4.50 (q, J=7.4 Hz, 1H), 4.12-4.31 (m, 4H), 3.55-3.67 (m, 2H), 2.29-2.45 (m, 2H), 1.85-1.98 (m, 2H), 1.70 (d, J=7.4 Hz, 3H), 1.29 (t, J=7.0 Hz, 3H)

Step 2: Preparation of 2-((1-(tetrahydro-2H-pyran-4-yl)-4-oxo-4,5-dihydro-1H-pyrazolo[3,4-d]pyrimidin-6-yl)thio)propanoic acid

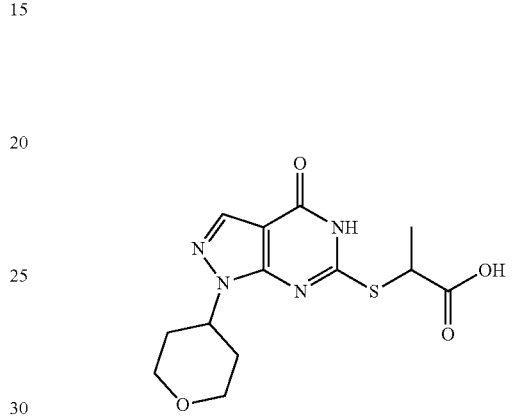

228 mg of ethyl 2-((1-(tetrahydro-2H-pyran-4-yl)-4-oxo-4,5-dihydro-1H-pyrazolo[3,4-d]pyrimidin-6-yl)thio)propanoate (0.647 mmol) prepared in Step 1 above was dissolved in 3 ml of tetrahydrofuran, and 2N sodium hydroxide was added, and mixture was stirred at room temperature for 1 hour 30 minutes. After completion of the reaction, it was neutralized with 1N hydrochloric acid, extracted with ethyl acetate, and washed with water and saturated brine. The resultant was concentrated under reduced pressure to give 178 mg of the solid title compound (0.549 mmol) in 85% yield.

$^1$H NMR (300 MHz, DMSO-d6) δ 12.97 (brs, 1H), 12.58 (brs, 1H), 7.98 (s, 1H), 4.65-4.80 (m, 1H), 4.39 (q, J=7.1 Hz, 1H), 3.93-4.05 (m, 2H), 3.41-3.54 (m, 2H), 1.96-2.16 (m, 2H), 1.77-1.92 (m, 2H), 1.55 (d, J=7.1 Hz, 3H)

<Example 45> Preparation of N-(5-(ethylthio)-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio)propanamide

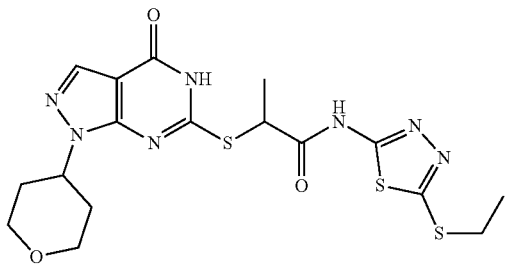 [SMILES: CCSc1nnc(NC(=O)C(C)Sc2nc3c(cnn3C3CCOCC3)c(=O)[nH]2)s1]

Step 1: Preparation of N-(5-(ethylthio)-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio)propanamide

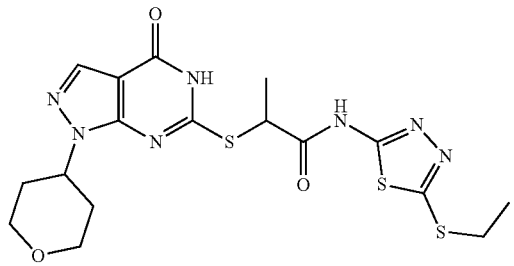 [SMILES: CCSc1nnc(NC(=O)C(C)Sc2nc3c(cnn3C3CCOCC3)c(=O)[nH]2)s1]

40 mg of 2-((1-(4,4-difluorocyclohexyl)-4-oxo-4,5-dihydro-1H-pyrazolo[3,4-d]pyrimidin-6-yl)thio)acetic acid (0.123 mmol) obtained in Preparation Example 24, 30 mg of 5-(ethylthio)-1,3,4-thiadiazole-2-amine (0.185 mmol) obtained in Preparation Example 4, and 54 mg of CIB (0.247 mmol) were dissolved in 2 ml of DMF, and 43 μl of DIPEA (0.247 mmol) was added, followed by stirring at 50° C. for 16 hours. After completion of the reaction, the resultant was extracted with ethyl acetate and washed with water and saturated brine. The filtrate concentrated under reduced pressure was purified by column chromatography (hexane:ethyl acetate=1:1->methanol/dichloromethane=3%, v/v) to give 25.6 mg of the solid title compound (0.055 mmol) in 45% yield.

Rf=0.06 (hexane:ethyl acetate=1:1, v/v)

$^1$H NMR (300 MHz, DMSO-d$_6$) δ 13.14 (brs, 1H), 12.61 (brs, 1H), 7.97 (s, 1H), 4.66 (q, J=7.1 Hz, 1H), 4.46-4.60 (m, 1H), 3.91-4.01 (m, 1H), 3.63-3.72 (m, 1H), 3.42-3.53 (m, 1H), 3.20 (t, J=7.2 Hz, 2H), 2.97-3.03 (m, 1H), 1.74-2.07 (m, 3H), 1.57 (d, J=7.1 Hz, 3H), 1.21-1.36 (m, 4H)

<Example 46> Preparation of N-(5-bromo-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio)propanamide

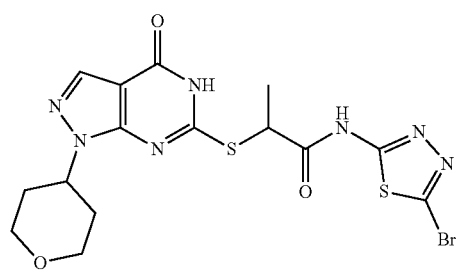 [SMILES: CC(Sc1nc2c(cnn2C2CCOCC2)c(=O)[nH]1)C(=O)Nc1nnc(Br)s1]

Step 1: Preparation of N-(5-bromo-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio)propanamide

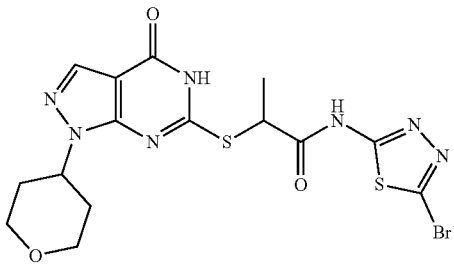 [SMILES: CC(Sc1nc2c(cnn2C2CCOCC2)c(=O)[nH]1)C(=O)Nc1nnc(Br)s1]

40 mg of 2-((1-(4,4-difluorocyclohexyl)-4-oxo-4,5-dihydro-1H-pyrazolo[3,4-d]pyrimidin-6-yl)thio)acetic acid (0.123 mmol) obtained in Preparation Example 24, 33 mg of 5-bromo-1,3,4-thiadiazol-2-amine (0.185 mmol), and 54 mg of CIB (0.247 mmol) were dissolved in 2 ml of DMF, and 43 μl of DIPEA (0.247 mmol) was added, followed by stirring at 50° C. for 16 hours. After completion of the reaction, the resultant was extracted with ethyl acetate and washed with water and saturated brine. The filtrate concentrated under reduced pressure was purified by column chromatography (hexane:ethyl acetate=1:1->methanol/dichloromethane=3%, v/v) to give 6.8 mg of the solid title compound (0.014 mmol) in 11% yield.

Rf=0.12 (hexane:ethyl acetate=1:1, v/v)

$^1$H NMR (300 MHz, DMSO-d$_6$) δ 13.42 (brs, 1H), 12.63 (brs, 1H), 7.97 (s, 1H), 4.68 (q, J=7.3 Hz. 1H), 4.49-4.62 (m, 1H), 3.92-4.02 (m, 1H), 3.68-3.78 (m, 1H), 3.42-3.54 (m, 1H), 3.03-3.15 (m, 1H), 1.75-2.07 (m, 3H), 1.58 (d, J=7.3 Hz, 3H), 1.24-1.37 (m, 1H)

<Example 47> Preparation of N-(5-chloro-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio)propanamide

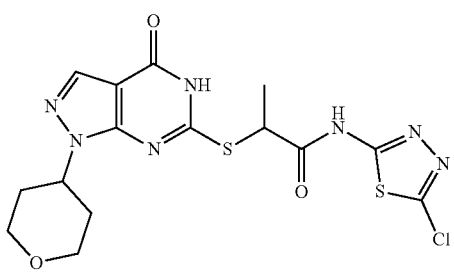 [SMILES: CC(Sc1nc2c(cnn2C2CCOCC2)c(=O)[nH]1)C(=O)Nc1nnc(Cl)s1]

Step 1: Preparation of N-(5-chloro-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio)propanamide

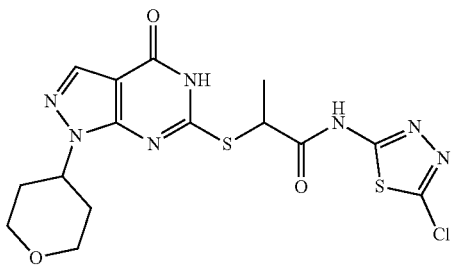 [SMILES: CC(Sc1nc2c(cnn2C2CCOCC2)c(=O)[nH]1)C(=O)Nc1nnc(Cl)s1]

40 mg of 2-((1-(4,4-difluorocyclohexyl)-4-oxo-4,5-dihydro-1H-pyrazolo[3,4-d]pyrimidin-6-yl)thio)acetic acid (0.123 mmol) obtained in Preparation Example 24, 25 mg of 5-chloro-1,3,4-thiadiazol-2-amine (0.185 mmol), and 54 mg of CIB (0.247 mmol) were dissolved in 2 ml of DMF, and 43 μl of DIPEA (0.247 mmol) was added and stirred at 50° C. for 16 hours. After completion of the reaction, the resultant was extracted with ethyl acetate and washed with water and saturated brine. The filtrate concentrated under reduced pressure was purified by column chromatography (hexane:ethyl acetate=1:1->methanol/dichloromethane=3%, v/v) to give 22.1 mg of the solid title compound (0.05 mmol) in 41% yield.

Rf=0.06 (hexane:ethyl acetate=1:1, v/v)

$^1$H NMR (300 MHz, DMSO-d$_6$) δ 13.41 (brs, 1H), 12.62 (brs, 1H), 7.97 (s, 1H), 4.68 (q, J=7.4 Hz, 1H), 4.49-4.62 (m, 1H), 3.92-4.01 (m, 1H), 3.68-3.78 (m, 1H), 3.43-3.55 (m, 1H), 3.03-3.14 (m, 1H), 1.75-2.09 (m, 3H), 1.58 (d, J=7.4 Hz, 3H), 1.25-1.37 (m, 1H)

<Example 48> Preparation of N-(5-chloro-1,3,4-thiadiazol-2-yl)-2-((1-(4,4-difluorocyclohexyl)-4-oxo-4,5-dihydro-1H-pyrazolo[3,4-d]pyrimidin-6-yl)thio)propanamide

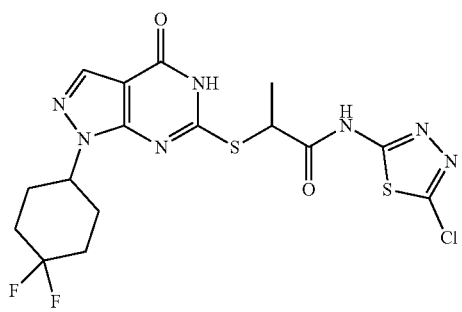 [SMILES: CC(Sc1nc2c(cnn2C2CCC(F)(F)CC2)c(=O)[nH]1)C(=O)Nc1nnc(Cl)s1]

Step 1: Preparation of N-(5-chloro-1,3,4-thiadiazol-2-yl)-2-((1-(4,4-difluorocyclohexyl)-4-oxo-4,5-dihydro-1H-pyrazolo[3,4-d]pyrimidin-6-yl)thio)propanamide

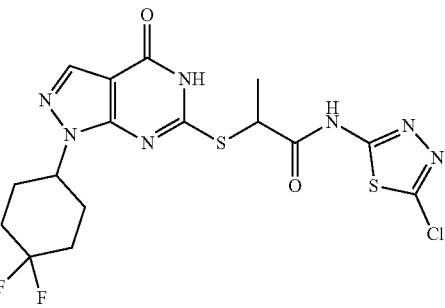

45 mg of 2-((1-(4,4-difluorocyclohexyl)-4-oxo-4,5-dihydro-1H-pyrazolo[3,4-d]pyrimidin-6-yl)thio)propanoic acid (0.126 mmol) obtained in Preparation Example 18.51 mg of 5-amino-2-chlorothiazole (0.378 mmol) and 64 mg of 2-chloro-1-methyl-pyridinium iodine (0.252 mmol) were dissolved in 2 ml of DMF, and 44 μl of DIPEA (0.252 mmol) was added, and stirred at 50° C. for 16 hours. After completion of the reaction, the resultant was extracted with ethyl acetate and washed with water and saturated brine. The filtrate concentrated under reduced pressure was purified by column chromatography (normal hexane:ethyl acetate=1:1->methanol/dichloromethane=3%, v/v) to give 44 mg of the solid title compound (0.092 mmol) in 73% yield.

Rf=0.26 (methanol/dichloromethane=5%, v/v)

$^1$H NMR (300 MHz, CDCl$_3$) δ 8.09 (s, 1H), 4.78-4.91 (m, 1H), 4.69 (q, J=7.4 Hz, 1H), 1.99-2.46 (m, 6H), 1.75 (d, J=7.4 Hz, 3H), 1.24-1.30 (m, 2H)

The chemical structural formulas of the compounds prepared in Example 1-48 are summarized and shown in the following table 1.

TABLE 1

| Example | Chemical Structure |
|---|---|
| 1 | 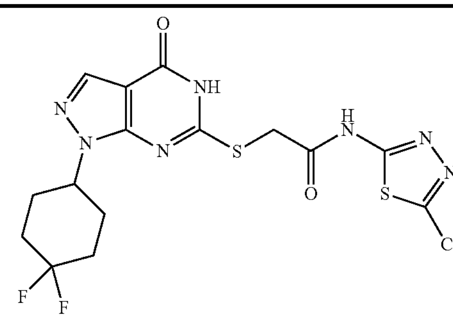 |
| 2 | 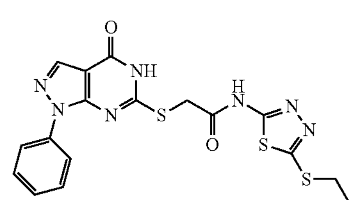 |

TABLE 1-continued
| Example | Chemical Structure |
|---|---|
| 3 | 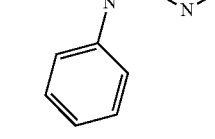 |
| 4 | 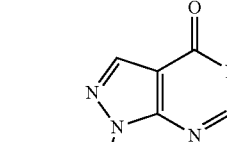 |
| 5 | 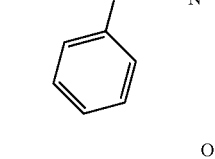 |
| 6 | 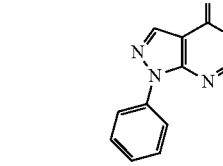 |
| 7 | 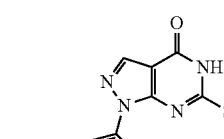 |
| 8 | 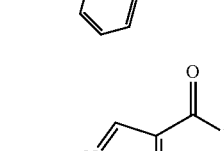 |
| 9 | 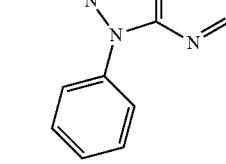 |
TABLE 1-continued
| Example | Chemical Structure |
|---|---|
| 10 | 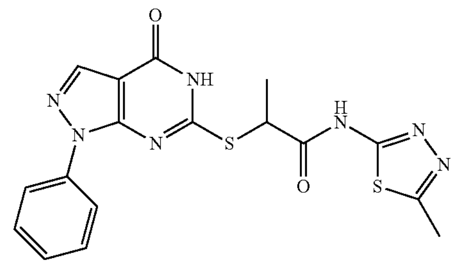 [SMILES: Cc1nnc(NC(=O)C(C)Sc2nc3c(cnn3-c3ccccc3)c(=O)[nH]2)s1] |
| 11 | 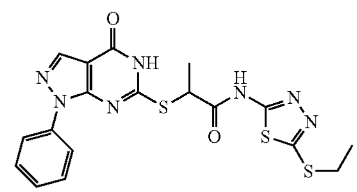 [SMILES: CCSc1nnc(NC(=O)C(C)Sc2nc3c(cnn3-c3ccccc3)c(=O)[nH]2)s1] |
| 12 | 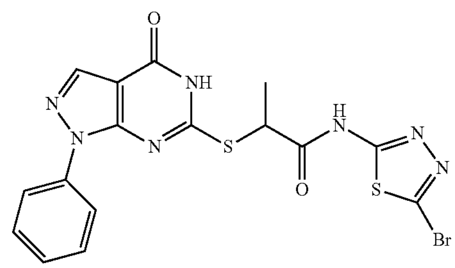 [SMILES: CC(Sc1nc2c(cnn2-c2ccccc2)c(=O)[nH]1)C(=O)Nc1nnc(Br)s1] |
| 13 | 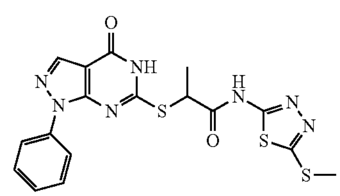 [SMILES: CSc1nnc(NC(=O)C(C)Sc2nc3c(cnn3-c3ccccc3)c(=O)[nH]2)s1] |
| 14 | 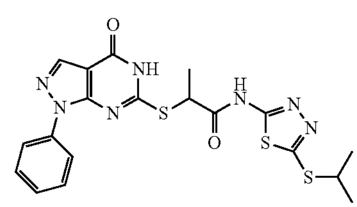 [SMILES: CC(C)Sc1nnc(NC(=O)C(C)Sc2nc3c(cnn3-c3ccccc3)c(=O)[nH]2)s1] |
| 15 | 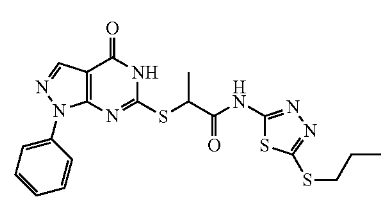 [SMILES: CCCSc1nnc(NC(=O)C(C)Sc2nc3c(cnn3-c3ccccc3)c(=O)[nH]2)s1] |
| 16 | 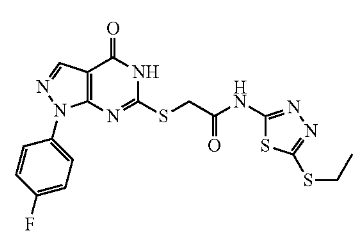 [SMILES: CCSc1nnc(NC(=O)CSc2nc3c(cnn3-c3ccc(F)cc3)c(=O)[nH]2)s1] |

TABLE 1-continued
| Example | Chemical Structure |
|---|---|
| 17 | 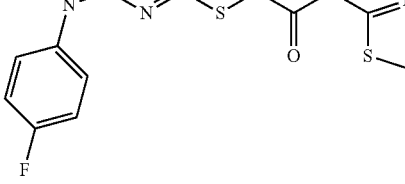 |
| 18 | 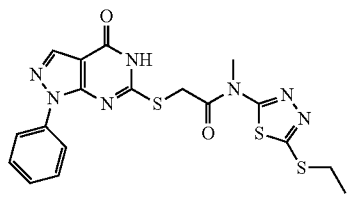 [SMILES: CCSc1nnc(N(C)C(=O)CSc2nc3c(cnn3-c3ccccc3)c(=O)[nH]2)s1] |
| 19 | 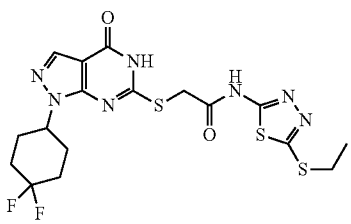 [SMILES: CCSc1nnc(NC(=O)CSc2nc3c(cnn3C3CCC(F)(F)CC3)c(=O)[nH]2)s1] |
| 20 | 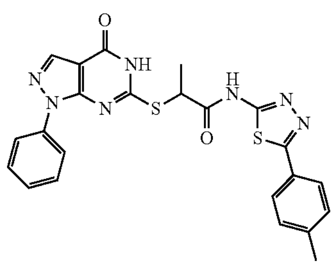 [SMILES: Cc1ccc(-c2nnc(NC(=O)C(C)Sc3nc4c(cnn4-c4ccccc4)c(=O)[nH]3)s2)cc1] |
| 21 | 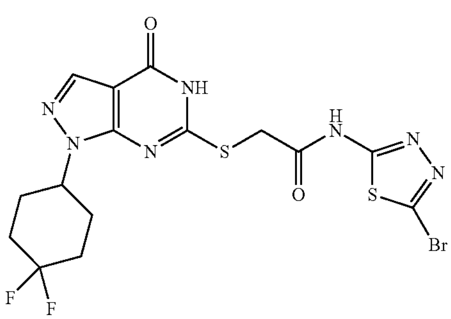 [SMILES: O=C(CSc1nc2c(cnn2C2CCC(F)(F)CC2)c(=O)[nH]1)Nc1nnc(Br)s1] |
| 22 | 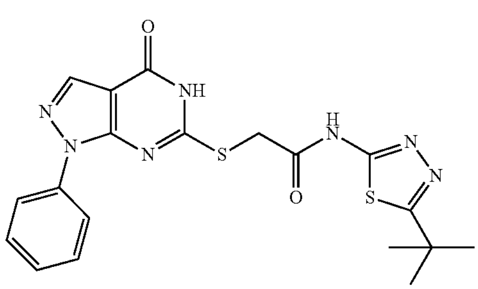 [SMILES: CC(C)(C)c1nnc(NC(=O)CSc2nc3c(cnn3-c3ccccc3)c(=O)[nH]2)s1] |
TABLE 1-continued
| Example | Chemical Structure |
|---|---|
| 23 | 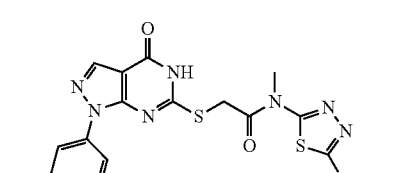 |
| 24 | 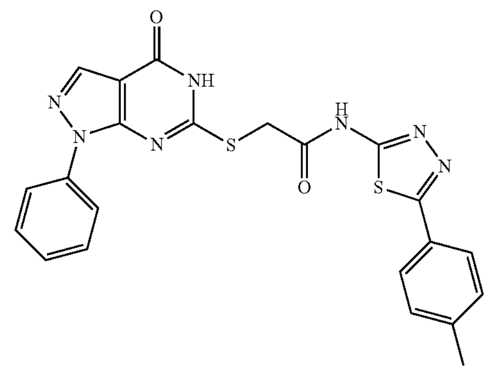 [SMILES: Cc1ccc(-c2nnc(NC(=O)CSc3nc4c(cnn4-c4ccccc4)c(=O)[nH]3)s2)cc1] |
| 25 | 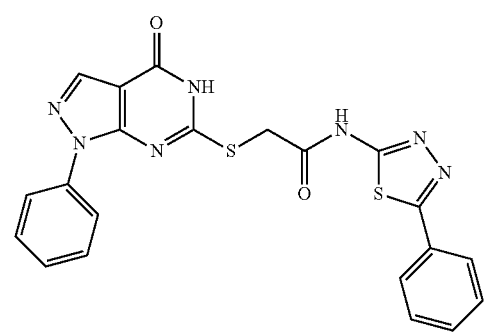 [SMILES: O=C(CSc1nc2c(cnn2-c2ccccc2)c(=O)[nH]1)Nc1nnc(-c2ccccc2)s1] |
| 26 | 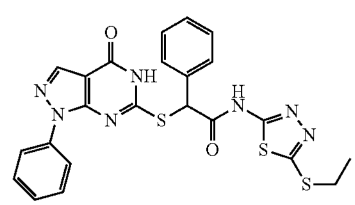 [SMILES: CCSc1nnc(NC(=O)C(Sc2nc3c(cnn3-c3ccccc3)c(=O)[nH]2)c2ccccc2)s1] |
| 27 | 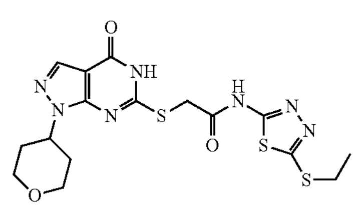 [SMILES: CCSc1nnc(NC(=O)CSc2nc3c(cnn3C3CCOCC3)c(=O)[nH]2)s1] |

TABLE 1-continued
| Example | Chemical Structure |
|---|---|
| 28 | 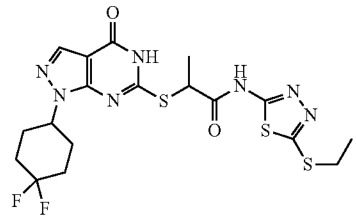 [SMILES: CCSc1nnc(NC(=O)C(C)Sc2nc3c(cnn3C3CCC(F)(F)CC3)c(=O)[nH]2)s1] |
| 29 | 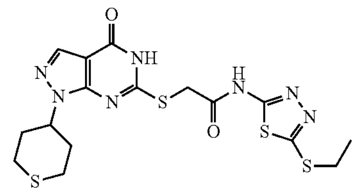 |
| 30 | 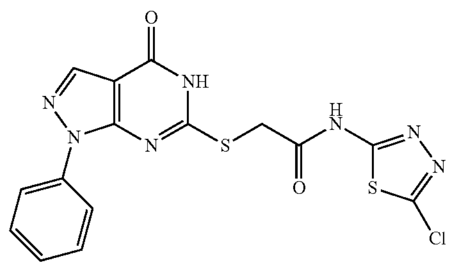 [SMILES: O=C(CSc1nc2c(cnn2-c2ccccc2)c(=O)[nH]1)Nc1nnc(Cl)s1] |
| 31 | 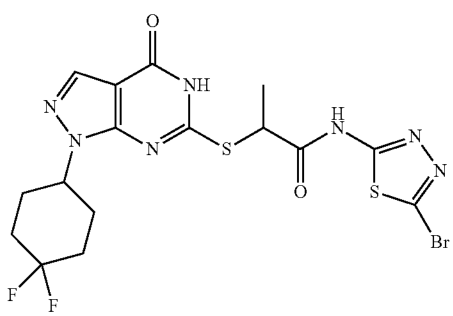 [SMILES: CC(Sc1nc2c(cnn2C2CCC(F)(F)CC2)c(=O)[nH]1)C(=O)Nc1nnc(Br)s1] |
| 32 | 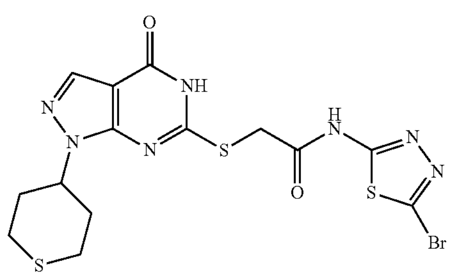 [SMILES: O=C(CSc1nc2c(cnn2C2CCSCC2)c(=O)[nH]1)Nc1nnc(Br)s1] |
| 33 | 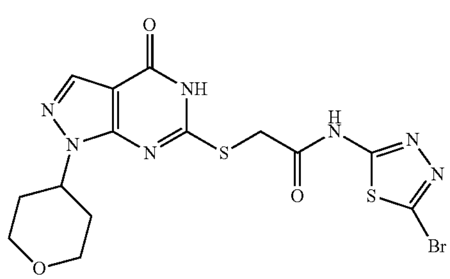 [SMILES: O=C(CSc1nc2c(cnn2C2CCOCC2)c(=O)[nH]1)Nc1nnc(Br)s1] |
TABLE 1-continued
| Example | Chemical Structure |
|---|---|
| 34 | 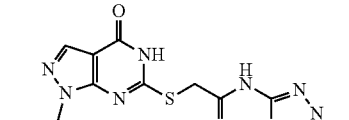 |
| 35 | 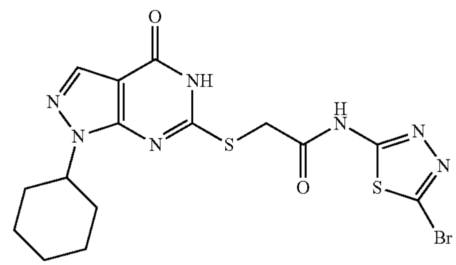 [SMILES: O=C(CSc1nc2c(cnn2C2CCCCC2)c(=O)[nH]1)Nc1nnc(Br)s1] |
| 36 | 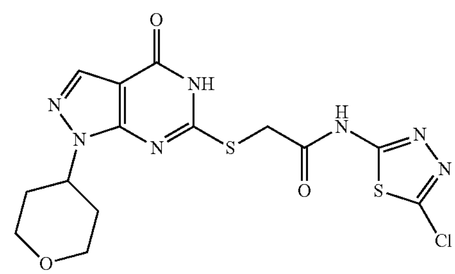 [SMILES: O=C(CSc1nc2c(cnn2C2CCOCC2)c(=O)[nH]1)Nc1nnc(Cl)s1] |
| 37 | 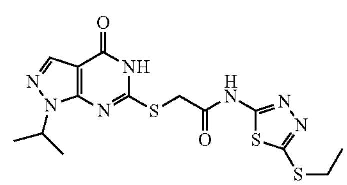 [SMILES: CCSc1nnc(NC(=O)CSc2nc3c(cnn3C(C)C)c(=O)[nH]2)s1] |
| 38 | 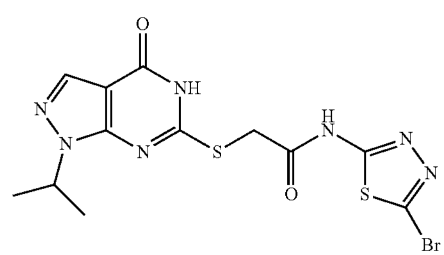 [SMILES: CC(C)n1ncc2c(=O)[nH]c(SCC(=O)Nc3nnc(Br)s3)nc21] |
| 39 | 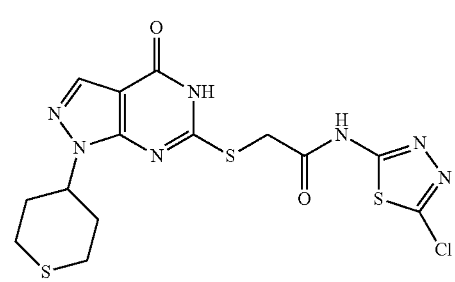 |

TABLE 1-continued

| Example | Chemical Structure |
|---|---|
| 40 | 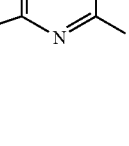 |
| 41 | 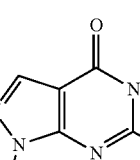 |
| 42 | 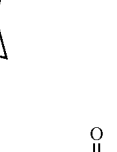 |
| 43 | 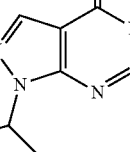 |
| 44 | 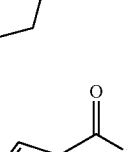 |
| 45 | 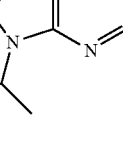 |
| 46 | 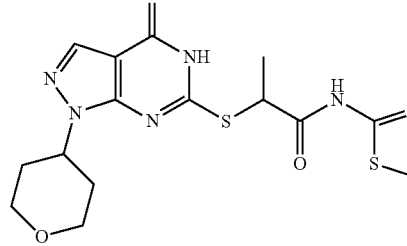 |
| 47 | 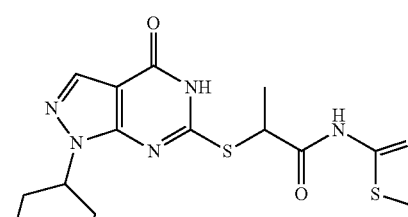 |
| 48 | 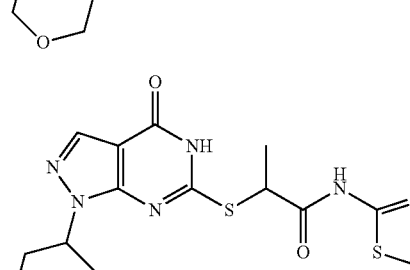 |

The inhibitory activity of the representative compounds according to the present invention against phosphodiesterase 9A was tested based on the polarization assay (IMAP-FP screening express kit) provided by MDS (MDS Analytical Technologies, Sunyvale, CA, USA). As a buffer solution, a reaction solution (a reaction solution containing 0.01% Tween 20 provided by MDS was diluted 5 times, then 5 mM DTT is added) and a polarization detection solution (binding solution A and B provided by MDS were mixed at a ratio of 3:1 and IMAP binding reagent 1/600 was added) were prepared. 100 μM of the substrate (Fl-cGMP substrate; MDS) and 3.6 μg/ml of the enzyme PDE9A (ab54113; abeam) were prepared. 3.6 μg/ml PDE9A and 100 μM substrate were diluted to 20 ng/ml (final reaction concentration: 5 ng/ml) and 400 nM (final reaction concentration: 100 nM), respectively. The buffer solution used for all dilution and preparation processes was 1× reaction solution with 1 mM DTT added, and the polarization detection solution was used to induce polarization at the end.

The prepared samples were dispensed on black microplates (Multiwell 384 well plates, #3573, Corning Life Sciences, Lowell, MA, USA) using a 16-channel pipette (multi 16-channel, Finnpipette, Thermo Scientific, Essex, UK). The total reaction volume per well is 20 μl. At this time, 10 μl of 2% DMSO, 5 μl of substrate solution, and 5 μl of reaction solution were used as a negative control, and 10 μl of 2% DMSO, 5 μl of substrate solution, and 5 μl of PDE9A solution were used as a positive control. As the experimental group, 10 μl of the compound prepared in Example, 5 µl of the substrate solution, and 5 µl of the PDE9A solution were used. After pretreatment between the compound and the enzyme was performed for about f 0 minutes before the enzyme-substrate reaction, 5 µl of cGMP was added to induce the enzyme reaction. During the reaction, each compound, enzyme, and substrate occupied 50%, 25%, and 25% of the total volume, respectively, and they were prepared at high concentrations of 2, 4, and 4 times, respectively, immediately before addition. After the enzymatic reaction, it was shaken lightly for 1 minute and the enzyme reaction was induced at room temperature for 1 hour. Then, 60 µl of a polarization detection solution prepared in advance was added to induce polarization.

Nanoparticles composed of trivalent metal ions are mixed in the fluorescence detection solution, which combines with phosphoric acid expose by enzymatic reaction to increase the molecular weight and induce polarization. After leaving for 2 hours at room temperature, the polarization (Fluorescence Polarization, FP) value was measured using a multi-label counter (Envision, PerkinElmer, Turku, Finland) (emission wavelength: P-535 nm, S-535 nm, excitation wavelength: 480 nm), and the result was expressed as an $IC_{50}$ value, which is the concentration of the compound that inhibited PDE9A by 50% in vitro (Table 2).

TABLE 2

| Example No. | PDE9A ($IC_{50}$, µM) |
|---|---|
| 1 | 0.0004 |
| 2 | 0.010 |
| 3 | 0.34 |
| 4 | 0.23 |
| 5 | 0.18 |
| 6 | 0.014 |
| 7 | 0.012 |
| 8 | 0.019 |
| 9 | 0.015 |
| 10 | 0.15 |
| 11 | 0.010 |
| 12 | 0.007 |
| 13 | 0.029 |
| 14 | 0.009 |
| 15 | 0.011 |
| 16 | 0.027 |
| 17 | 0.027 |
| 18 | 0.47 |
| 19 | 0.0006 |
| 20 | 0.019 |
| 21 | 0.0004 |
| 22 | 0.10 |
| 23 | 0.010 |
| 24 | 0.041 |
| 25 | 0.012 |
| 26 | 0.009 |
| 27 | 0.0005 |
| 28 | 0.0001 |
| 29 | 0.0003 |
| 30 | 0.018 |
| 31 | 0.0001 |
| 32 | 0.0006 |
| 33 | 0.0004 |
| 34 | 0.001 |
| 35 | 0.001 |
| 36 | 0.0007 |
| 37 | 0.001 |
| 38 | 0.003 |
| 39 | 0.001 |
| 40 | 0.039 |
| 41 | 0.028 |
| 42 | 0.001 |
| 43 | 0.003 |
| 44 | 0.036 |
| 45 | 0.0001 |
| 46 | 0.0002 |
| 47 | 0.0001 |
| 48 | 0.0003 |

The invention claimed is:

1. A method for or preventing a disease related to Phosphodiesterase 9A, comprising administering a therapeutically effective amount of a compound represented by the following Chemical formula 1 or a pharmaceutically acceptable salt thereof:

[Chemical Formula 1]

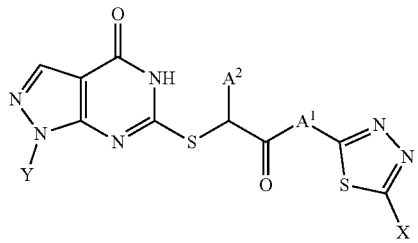

in Chemical Formula 1,
$A^1$ is NH or N-$C_{1-2}$alkyl,
$A^2$ is H, linear or branched $C_{1-5}$alkyl, or phenyl,
X is a substituent selected from the group consisting of —H, halogen, —$NO_2$, —CN, -$SR^1$, linear or branched $C_{1-10}$alkyl unsubstituted or substituted with one or more halogens, linear or branched $C_{1-10}$alkoxy unsubstituted or substituted with one or more halogens, $C_{6-10}$aryl unsubstituted or substituted with one or more halogen or $C_{1-10}$ linear or branched alkyl, and $C_{6-10}$aryloxy unsubstituted or substituted with one or more halogen or $C_{1-10}$ linear or branched alkyl,
Y is a substituent selected from the group consisting of $C_{1-10}$ linear or branched alkyl unsubstituted or substituted with one or more halogens, $C_{3-10}$cycloalkyl unsubstituted or substituted with one or more halogens, 6-10 membered heterocycloalkyl comprising O or S heteroatom unsubstituted or substituted with one or more halogens, $C_{1-10}$ linear or branched alkoxy unsubstituted or substituted with one or more halogens, $C_{6-10}$aryl unsubstituted or substituted with one or more halogen or $C_{1-10}$ linear or branched alkyl, and $C_{6-10}$aryloxy unsubstituted or substituted with one or more halogen or $C_{1-10}$ linear or branched alkyl, and
$R_1$ is a substituent selected from the group consisting of $C_{1-10}$ linear or branched alkyl unsubstituted or substituted with one or more halogens, $C_{1-10}$ linear or branched alkoxy unsubstituted or substituted with one or more halogens, $C_{6-10}$aryl unsubstituted or substituted with one or more halogen or $C_{1-10}$ linear or branched alkyl, $C_{1-2}$alkyl-$C_{6-10}$aryl unsubstituted or substituted with one or more halogen or $C_{1-10}$ linear or branched alkyl, and $C_{6-10}$aryloxy unsubstituted or substituted with one or more halogen or $C_{1-10}$ linear or branched alkyl.

2. The method according to claim 1, wherein
A1 is NH or N-$C_{1-2}$alkyl,
A2 is H, linear or branched $C_{1-5}$alkyl, or phenyl,
X is a substituent selected from the group consisting of —H, halogen, —$NO_2$, —CN, -$SR^1$, linear or branched $C_{1-5}$alkyl unsubstituted or substituted with one or more halogens, linear or branched $C_{1-5}$alkoxy unsubstituted or substituted with one or more halogens, and phenyl unsubstituted or substituted with one or more halogen or $C_{1-10}$ linear or branched alkyl, Y is a substituent selected from the group consisting of $C_{1-6}$ linear or branched alkyl unsubstituted or substituted with one or more halogens, $C_{3-6}$cycloalkyl unsubstituted or substituted with one or more halogens, 6-8 membered heterocycloalkyl comprising O or S heteroatom unsubstituted or substituted with one or more halogens, $C_{1-6}$ linear or branched alkoxy unsubstituted or substituted with one or more halogens, $C_{6-10}$aryl unsubstituted or substituted with one or more halogen or $C_{1-10}$ linear or branched alkyl, and $C_{6-10}$aryloxy unsubstituted or substituted with one or more halogen or $C_{1-10}$ linear or branched alkyl, and $R_1$ is a substituent selected from the group consisting of $C_{1-6}$ linear or branched alkyl unsubstituted or substituted with one or more halogens, $C_{1-6}$ linear or branched alkoxy unsubstituted or substituted with one or more halogens, $C_{6-10}$aryl unsubstituted or substituted with one or more halogen or $C_{1-10}$ linear or branched alkyl, and $C_{6-10}$aryloxy unsubstituted or substituted with one or more halogen or $C_{1-10}$ linear or branched alkyl.

3. The method according to claim 2, wherein
$A^1$ is NH or NCH$_3$,
$A^2$ is H, CH$_3$, or phenyl,
X is a substituent selected from the group consisting of —H, -Cl, —Br, -SR$^1$, methyl, ethyl, t-butyl, trifluoromethyl, methoxy, ethoxy, isopropoxy, phenyl, 4-fluorophenyl, and 4-methylphenyl,
Y is phenyl, 4-fluorophenyl, 4,4-difluorocyclohexyl, pyran, thiopyran, isopropyl or cyclopropyl, and
$R^1$ is methyl, ethyl, isopropyl, propyl, benzyl, 4-methylbenzyl or 4-chlorobenzyl.

4. The method according to claim 1, wherein the compound is (1) 2-((1-(4,4-difluorocyclohexyl)-4-oxo-4,5-dihydro-1H-pyrazolo[3,4-d]pyrimidin-6-yl)thio)-N-(5-chloro-1,3,4-thiadiazol-2-yl) acetamide;
(2) N-(5-(ethylthio)-1,3,4-thiadiazol-2-yl)-2-((4-oxo-1-phenyl-4,5-dihydro-1H-pyrazolo[3,4-d]pyrimidin-6-yl)thio) acetamide;
(3) N-(5-methyl-1,3,4-thiadiazol-2-yl)-2-((4-oxo-1-phenyl-4,5-dihydro-1H-pyrazolo[3,4-d]pyrimidin-6-yl) thio) acetamide;
(4) 2-((4-oxo-1-phenyl-4,5-dihydro-1H-pyrazolo[3,4-d] pyrimidin-6-yl)thio)-N-(1,3,4-thiadiazol-2-yl) acetamide;
(5) N-(5-ethyl-1,3,4-thiadiazol-2-yl)-2-((4-oxo-1-phenyl-4,5-dihydro-1H-pyrazolo[3,4-d]pyrimidin-6-yl)thio) acetamide;
(6) N-(5-(benzylthio)-1,3,4-thiadiazol-2-yl)-2-(4-oxo-1-phenyl-4,5-dihydro-1H-pyrazolo[3,4-d]pyrimidin-6-yl)thio) acetamide;
(7) N-(5-bromo-1,3,4-thiadiazol-2-yl)-2-((4-oxo-1-phenyl-4,5-dihydro-1H-pyrazolo[3,4-d]pyrimidin-6-yl) thio) acetamide;
(8) N-(5-((4-chlorobenzyl)thio)-1,3,4-thiadiazol-2-yl)-2-(4-oxo-1-phenyl-4,5-dihydro-1H-pyrazolo[3,4-d]pyrimidin-6-yl) acetamide;
(9) N-(5-((4-methylbenzyl)thio)-1,3,4-thiadiazol-2-yl)-2-(4-oxo-1-phenyl-4,5-dihydro-1H-pyrazolo[3,4-d]pyrimidin-6-yl) acetamide;
(10) N-(5-methyl-1,3,4-thiadiazol-2-yl)-2-((4-oxo-1-phenyl-4,5-dihydro-1H-pyrazolo[3,4-d]pyrimidin-6-yl) thio) propanamide;
(11) N-(5-(ethylthio)-1,3,4-thiadiazol-2-yl)-2-((4-oxo-1-phenyl-4,5-dihydro-1H-pyrazolo[3,4-d]pyrimidin-6-yl)thio) propanamide;
(12) N-(5-bromo-1,3,4-thiadiazol-2-yl)-2-((4-oxo-1-phenyl-4,5-dihydro-1H-pyrazolo[3,4-d]pyrimidin-6-yl) thio) propanamide;
(13) N-(5-(methylthio)-1,3,4-thiadiazol-2-yl)-2-((4-oxo-1-phenyl-4,5-dihydro-1H-pyrazolo[3,4-d]pyrimidin-6-yl)thio) acetamide;
(14) N-(5-(isopropylthio)-1,3,4-thiadiazol-2-yl)-2-((4-oxo-1-phenyl-4,5-dihydro-1H-pyrazolo[3,4-d]pyrimidin-6-yl)thio) acetamide;
(15) N-(5-(propylthio)-1,3,4-thiadiazol-2-yl)-2-((4-oxo-1-phenyl-4,5-dihydro-1H-pyrazolo[3,4-d]pyrimidin-6-yl)thio) acetamide;
(16) N-(5-(ethylthio)-1,3,4-thiadiazol-2-yl)-2-((1-(4-fluorophenyl)-4-oxo-4,5-dihydro-1H-pyrazolo[3,4-d]pyrimidin-6-yl)thio) acetamide;
(17) N-(5-bromo-1,3,4-thiadiazol-2-yl)-2-((1-(4-fluorophenyl)-4-oxo-4,5-dihydro-1H-pyrazolo[3,4-d]pyrimidin-6-yl)thio) acetamide;
(18) N-(5-(ethylthio)-1,3,4-thiadiazol-2-yl)-N-methyl-2-((4-oxo-1-phenyl-4,5-dihydro-1H-pyrazolo[3,4-d]pyrimidin-6-yl)thio) acetamide;
(19) 2-((1-(4,4-difluorocyclohexyl)-4-oxo-4,5-dihydro-1H-pyrazolo[3,4-d]pyrimidin-6-y1)thio)-N-(5-(ethylthio)-1,3,4-thiadiazol-2-yl) acetamide;
(20) 2-((4-oxo-1-phenyl-4,5-dihydro-1H-pyrazolo[3,4-d] pyrimidin-6-yl)thio)-N-(5-(p-tolyl)-1,3,4-thiadiazol-2-yl) propanamide;
(21) 2-((1-(4,4-difluorocyclohexyl)-4-oxo-4,5-dihydro-1H-pyrazolo[3,4-d]pyrimidin-6-yl)thio)-N-(5-bromo-1,3,4-thiadiazol-2-yl) acetamide;
(22) N-(5-(tertiary-butyl)-1,3,4-thiadiazol-2-yl)-2-((4-oxo-1-phenyl-4,5-dihydro-1H-pyrazolo[3,4-d]pyrimidin-6-yl)thio) acetamide;
(23) N-(5-(4-fluorophenyl)-1,3,4-thiadiazol-2-yl)-2-((4-oxo-1-phenyl-4,5-dihydro-1H-pyrazolo[3,4-d]pyrimidin-6-yl)thio) acetamide;
(24) N-(5-phenyl-1,3,4-thiadiazol-2-yl)-2-((4-oxo-1-phenyl-4,5-dihydro-1H-pyrazolo[3,4-d]pyrimidin-6-yl) thio) acetamide;
(25) 2-((4-oxo-1-phenyl-4,5-dihydro-1H-pyrazolo[3,4-d] pyrimidin-6-yl)thio)-N-(5-(p-tolyl)-1,3,4-thiadiazol-2-yl) acetamide;
(26) N-(5-(ethylthio)-1,3,4-thiadiazol-2-yl)-2-((4-oxo-1-phenyl-4,5-dihydro-1H-pyrazolo[3,4-d]pyrimidin-6-yl)thio)-2-phenylacetamide;
(27) N-(5-(ethylthio)-1,3,4-thiadiazol-2-yl)-2-((4-oxo-1-(tetrahydro-2H-pyran-4-yl)-4,5-dihydro-1H-pyrazolo [3,4-d]pyrimidin-6-yl)thio) acetamide;
(28) 2-((1-(4,4-difluorocyclohexyl)-4-oxo-4,5-dihydro-1H-pyrazolo[3,4-d]pyrimidin-6-yl)thio)-N-(5-(ethylthio)-1,3,4-thiadiazol-2-yl) propanamide;
(29) N-(5-(ethylthio)-1,3,4-thiadiazol-2-yl)-2-((4-oxo-1-(tetrahydro-2H-thiopyran-4-yl)-4,5-dihydro-1H-pyrazolo[3,4-d]pyrimidin-6-yl)thio) acetamide;
(30) N-(5-chloro-1,3,4-thiadiazol-2-yl)-2-((4-oxo-1-phenyl-4,5-dihydro-1H-pyrazolo[3,4-d]pyrimidin-6-yl) thio) acetamide;
(31) 2-((1-(4,4-difluorocyclohexyl)-4-oxo-4,5-dihydro-1H-pyrazolo[3,4-d]pyrimidin-6-yl)thio)-N-(5-bromo-1,3,4-thiadiazol-2-yl) propanamide;

(32) N-(5-bromo-1,3,4-thiadiazol-2-yl)-2-((4-oxo-1-(tetrahydro-2H-thiopyran-4-yl)-4,5-dihydro-1H-pyrazolo[3,4-d]pyrimidin-6-yl)thio) acetamide;
(33) N-(5-bromo-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio) acetamide;
(34) N-(5-(ethylthio)-1,3,4-thiadiazol-2-yl)-2-((1-cyclohexyl-4-oxo-4,5-dihydro-1H-pyrazolo[3,4-d]pyrimidin-6-yl)thio) acetamide;
(35) N-(5-bromo-1,3,4-thiadiazol-2-yl)-2-((1-cyclohexyl-4-oxo-4,5-dihydro-1H-pyrazolo[3,4-d]pyrimidin-6-yl)thio) acetamide;
(36) N-(5-chloro-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio) acetamide;
(37) N-(5-(ethylthio)-1,3,4-thiadiazol-2-yl)-2-((1-isopropyl-4-oxo-4,5-dihydro-1H-pyrazolo[3,4-d]pyrimidin-6-yl)thio) acetamide;
(38) N-(5-bromo-1,3,4-thiadiazol-2-yl)-2-((1-isopropyl-4-oxo-4,5-dihydro-1H-pyrazolo[3,4-d]pyrimidin-6-yl)thio) acetamide;
(39) N-(5-chloro-1,3,4-thiadiazol-2-yl)-2-((4-oxo-1-(tetrahydro-2H-thiopyran-4-yl)-4,5-dihydro-1H-pyrazolo[3,4-d]pyrimidin-6-yl)thio) acetamide;
(40) N-(5-(ethylthio)-1,3,4-thiadiazol-2-yl)-2-((1-cyclopropyl-4-oxo-4,5-dihydro-1H-pyrazolo[3,4-d]pyrimidin-6-yl)thio) acetamide;
(41) N-(5-bromo-1,3,4-thiadiazol-2-yl)-2-((1-cyclopropyl-4-oxo-4,5-dihydro-1H-pyrazolo[3,4-d]pyrimidin-6-yl)thio) acetamide;
(42) N-(5-chloro-1,3,4-thiadiazol-2-yl)-2-((1-cyclohexyl-4-oxo-4,5-dihydro-1H-pyrazolo[3,4-d]pyrimidin-6-yl)thio) acetamide;
(43) N-(5-chloro-1,3,4-thiadiazol-2-yl)-2-((1-isopropyl-4-oxo-4,5-dihydro-1H-pyrazolo[3,4-d]pyrimidin-6-yl)thio) acetamide;
(44) N-(5-chloro-1,3,4-thiadiazol-2-yl)-2-((1-cyclopropyl-4-oxo-4,5-dihydro-1H-pyrazolo[3,4-d]pyrimidin-6-yl)thio) acetamide;
(45) N-(5-(ethylthio)-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio) propanamide;
(46) N-(5-bromo-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio) propanamide;
(47) N-(5-chloro-1,3,4-thiadiazol-2-yl)-2-((4-oxo-1-(tetrahydro-2H-pyran-4-yl)-4,5-dihydro-1H-pyrazolo[3,4-d]pyrimidin-6-yl)thio) propanamide; or
(48) N-(5-chloro-1,3,4-thiadiazol-2-yl)-2-((1-(4,4-difluorocyclohexanyl)-4-oxo-4,5-dihydro-1H-pyrazolo[3,4-d]pyrimidin-6-yl)thio) propanamide.

5. The method according to claim 1, wherein the disease is a neurological disease or a mental disease.

6. The method according to claim 5, wherein the neurological or mental disorder is Alzheimer's disease, Huntington's disease, Lewy body demntia, or Pick's syndrome.

7. The method according to claim 1, wherein the disease is heart failure.

8. The method according to claim 7, wherein the disease is cardiac output-preserving heart failure or sickle cell disease.

* * * * *